US011643648B2

(12) United States Patent
Tsuge et al.

(10) Patent No.: US 11,643,648 B2
(45) Date of Patent: May 9, 2023

(54) METHOD FOR CONSTRUCTING CHIMERIC PLASMID LIBRARY

(71) Applicant: NATIONAL UNIVERSITY CORPORATION KOBE UNIVERSITY, Kobe (JP)

(72) Inventors: Kenji Tsuge, Kobe (JP); Jun Ishii, Kobe (JP); Akihiko Kondo, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 5 days.

(21) Appl. No.: 17/600,836

(22) PCT Filed: Mar. 24, 2020

(86) PCT No.: PCT/JP2020/013133
§ 371 (c)(1),
(2) Date: Oct. 1, 2021

(87) PCT Pub. No.: WO2020/203496
PCT Pub. Date: Oct. 8, 2020

(65) Prior Publication Data
US 2022/0177871 A1    Jun. 9, 2022

(30) Foreign Application Priority Data
Apr. 1, 2019   (JP) .............................. JP2019-069798

(51) Int. Cl.
*C40B 50/06* (2006.01)
*C12N 15/10* (2006.01)
(Continued)

(52) U.S. Cl.
CPC ......... *C12N 15/1037* (2013.01); *C12N 15/63* (2013.01); *C12P 19/34* (2013.01); *C40B 50/06* (2013.01)

(58) Field of Classification Search
None
See application file for complete search history.

(56) References Cited

U.S. PATENT DOCUMENTS

2017/0009243 A1    1/2017   Tsuge et al.

FOREIGN PATENT DOCUMENTS

| JP | 2004129654 A | 4/2004 |
| WO | 0077181 A2 | 12/2000 |
| WO | 2015111248 A1 | 7/2015 |

OTHER PUBLICATIONS

Engler et al., "A One Pot, One Step, Precision Cloning Method with High Throughput Capability", PloS ONE, vol. 3, No. 11; Dated Nov. 2008; pp. 1-7.
(Continued)

*Primary Examiner* — Christian C Boesen
(74) *Attorney, Agent, or Firm* — Cantor Colburn LLP

(57) ABSTRACT

The present invention addresses the problem of providing a novel method which is for preparing a DNA fragment for microbial cell transformation, and by which the combinatorial library of a long-chain DNA can be efficiently constructed and confirmation of the genotype of the obtained clone is facilitated. The present invention is a method for preparing a DNA fragment, which is for microbial cell transformation and has at least one insert DNA unit that includes a DNA containing an effective replication origin in a host microorganism and an insert DNA in which unit DNAs are linked, the method being characterized by including: (A) a step for preparing, through an OGAB method, a plurality of types of plasmids having an insert DNA unit in which a plurality of types of unit DNAs capable of being linked in a specific linking order are linked; (B) a step for decomposing a plasmid into unit DNAs by treating the plurality of types of plasmids prepared in the step (A) with a restriction enzyme suitable for each plasmid and preparing (Continued)

a mixed liquid of a plurality of types of unit DNAs; and (C) a step for preparing a long-chain DNA fragment by re-assembling the unit DNAs through the OGAB method by using the mixed liquid of a plurality of types of unit DNAs obtained in the step (B).

20 Claims, 7 Drawing Sheets

Specification includes a Sequence Listing.

(51) Int. Cl.
  *C12N 15/63*   (2006.01)
  *C12P 19/34*   (2006.01)

(56) References Cited

OTHER PUBLICATIONS

Gibson et al., "Enzymatic assembly of DNA molecules up to several hundred kilobases", Brief Communications, Nature Methods, vol. 6, No. 5; Dated May 2009; pp. 343-346.

Gibson et al., "One-step assembly in yeast of 25 overlapping DNA fragments to form a complete synthetic Mycoplasma genitalium genome", The J. Craig Venter Institute, Synthetic Biology Group, vol. 105, No. 51; Dated Dec. 23, 2008; pp. 20404-20409.

Li et al., "Harnessing homologous recombination in vitro to generate recombinant DNA via SLIC", Nature Publishing Group, vol. 4, No. 3; Dated Mar. 2007; pp. 251-256.

Tsuge et al., "One step assembly of multiple DNA fragments with a designed order and orientation in Bacillus subtilis plasmid", Nucleic Acids Research, vol. 31, No. 21, Dated: 2003; pp. 1-8.

De Kok et al., "Rapid and Reliable DNA Assembly via Ligase Cycling Reaction", ACS Synthetic Biology, vol. 3; Dated: 2014; pp. 97-106.

Tsuge et al., "Method of preparing an equimolar DNA mixture for one-step DNA assembly of over 50 fragments", Scientific Reports, vol. 5, Dated 2015; pp. 1-11.

International Search Report for corresponding International Application No. PCT/JP2020/013133; dated Jun. 16, 2020.

Engler et al., "Golden Gate Shuffling: A One-Pot DNA Shuffling Method Based on Type IIs Restriction Enzymes" PLoS one, vol. 4, Issue 5, May 2009; 8 pages.

JPO Notice of Reasons for Refusal for corresponding JP Application No. 2021-511512; dated Feb. 14, 2022.

EPO Extended European Search Report for corresponding EP Application No. 20781743.8; dated Dec. 15, 2022.

Itaya et al., "Efficient delivery of large DNA from *Escherichia coli* to Synechococcus elongatus PCC7942 by broad-host-range conjugal plasmid pUB307", Journal of Biochemistry, vol. 164, No. 1, Feb. 6, 2018, pp. 15-20.

Juhas et al., "High molecular weight DNA assembly in vivo for synthetic biology applications", Critical Reviews In Biotechnology, vol. 37, No. 3, Feb. 10, 2016, pp. 277-286.

Liu et al., "Synthetic Biology Toolbox and Chassis Development in *Bacillus subtilis*", Trends in Biotechnology, vol. 37, No. 5, May 1, 2019, pp. 548-562.

FIG.2
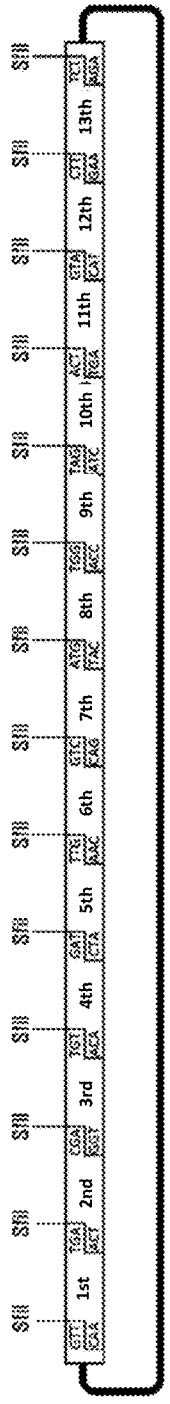
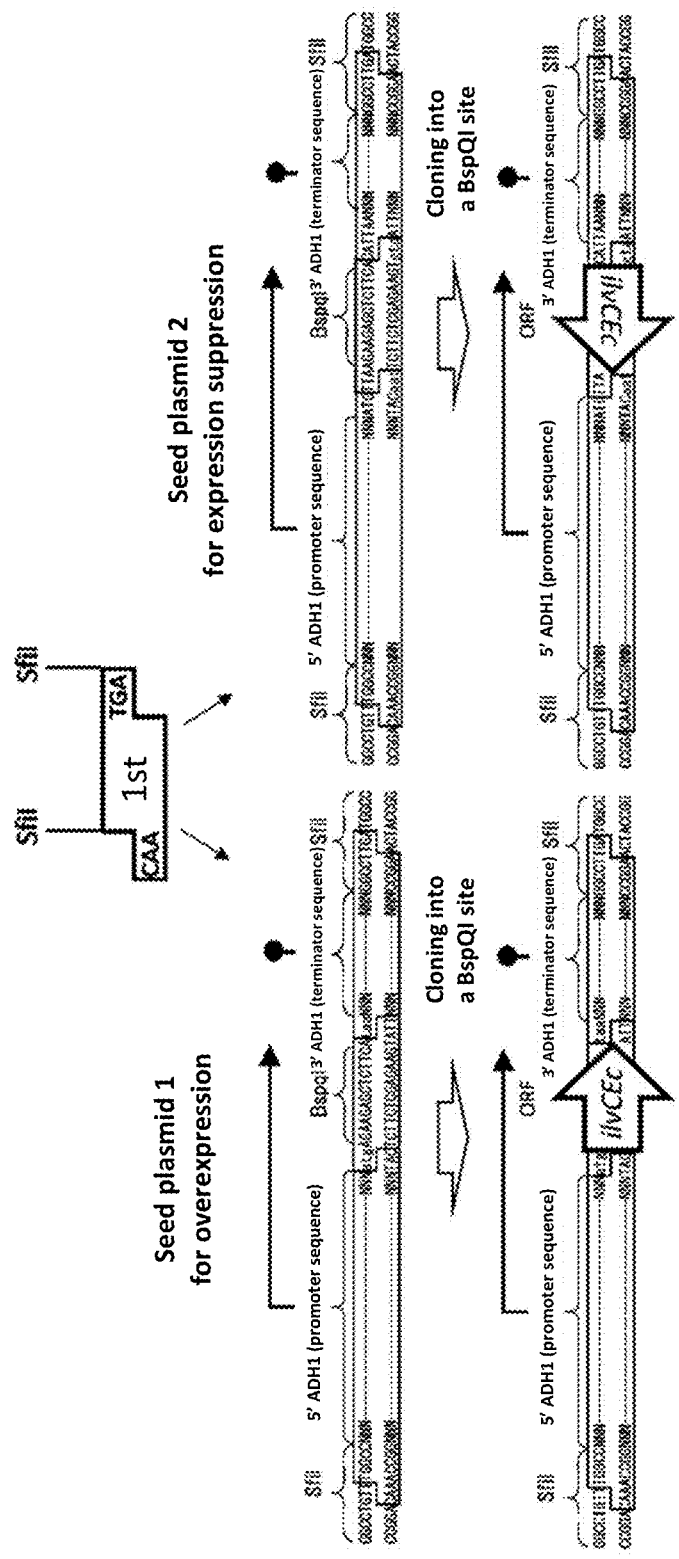

FIG.5

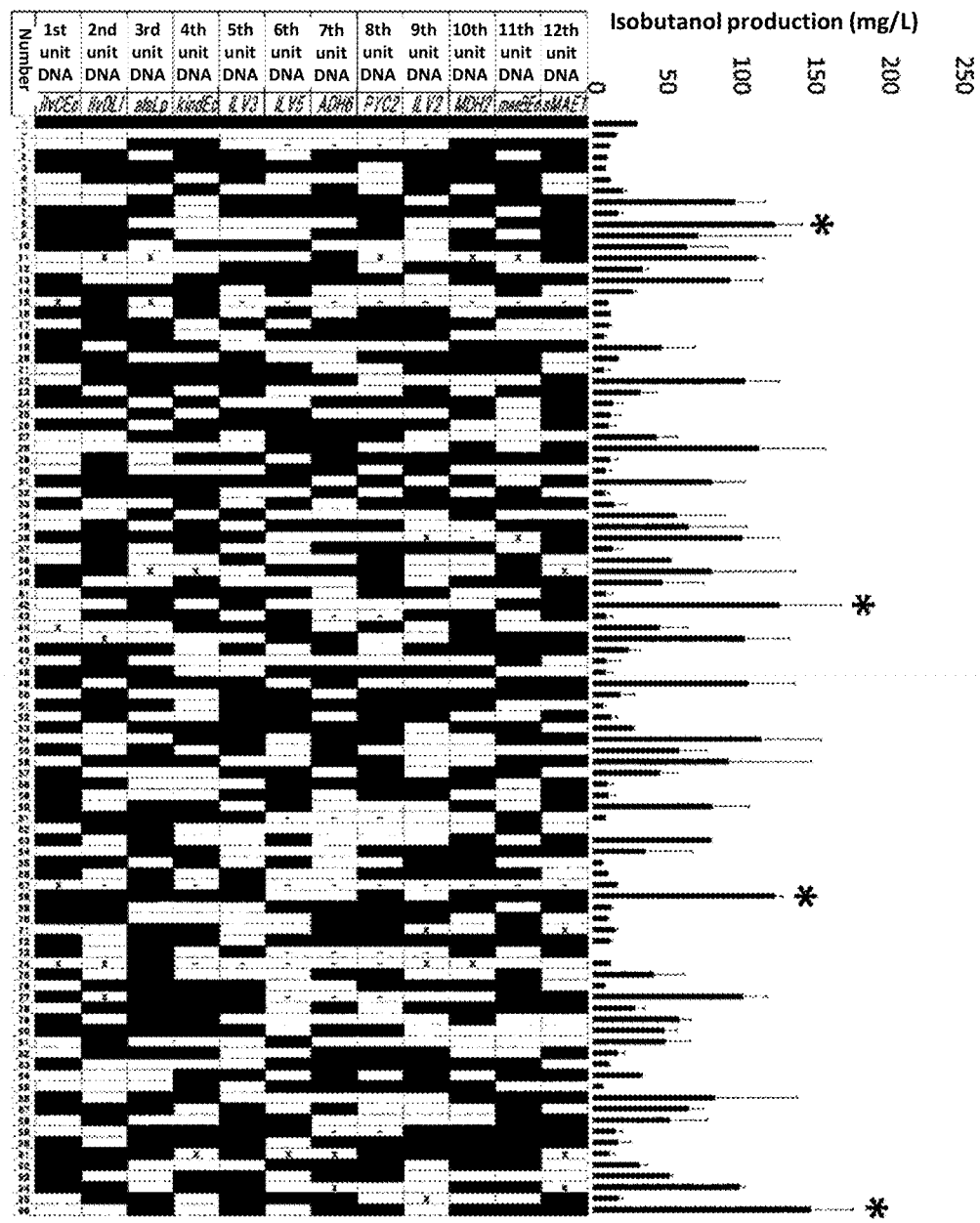

White indicates the forward (F) direction, black indicates the reverse (R) direction, × indicates a gene that could not be determined whether it is F or R, - indicates a loss of the unit DNA, and * indicates a gene used for the seed plasmid for the second library. The isobutanol production is shown with the mean value and the standard deviation for the production in the medium in two or more times of independent culture.

White indicates the forward (F) direction, black indicates the reverse (R) direction, and - indicates a loss of the unit DNA. The isobutanol production is shown with the mean value and the standard deviation for the production in the medium in three times of independent culture.

METHOD FOR CONSTRUCTING CHIMERIC PLASMID LIBRARY

CROSS REFERENCE TO RELATED APPLICATIONS

This is the U.S. national stage of application No. PCT/JP2020/013133, filed on Mar. 24, 2020. Priority under 35 U.S.C. § 119(a) and 35 U.S.C. § 365(b) is claimed from Japanese Application No. 2019-069798, filed Apr. 1, 2019, the disclosure of which is also incorporated herein by reference.

TECHNICAL FIELD

The present invention relates to a novel method for constructing a chimeric plasmid library.

BACKGROUND ART

In association with the progress in synthetic biology, there is an increasing demand for a long-chain DNA in which a plurality of genes are linked. In sequence designing for a long-chain DNA, it is unlikely that a result of interest can be achieved with sequence designing at once because it is necessarily required to learn many expression parameters such as choices of the type of gene to be used or choices of the expression intensity of the gene. Thus, in many cases, the sequence designing is on the premise of performing a DBTL cycle (Design-Build-Test-Learn cycle), in which a long-chain DNA is Designed first, the long-chain DNA is Built, the long-chain DNA is then Tested, the content thereof is Learned, and a new DNA based on the finding is constructed. In order to learn many expression parameters at the same time in this DBTL cycle, a combinatorial library technique for selecting one choice from a plurality of choices for each expression parameter and linking each of them to construct various types of long-chain DNAs is desirable from the efficiency viewpoint. In other words, it is easier to derive the direction of DNA design for each expression parameter in a shorter cycle by simultaneously constructing and comparing a plurality of types of long-chain DNAs with a variety for each expression parameter rather than by constructing and testing only a single long-chain DNA.

However, synthesis of a long-chain DNA generally incurs costs and takes time, and it is often difficult to construct a plurality of long-chain DNAs. A multiple gene fragment assembling technique for preparing many short DNA fragments with the functional unit of a gene or the like as an index and linking (assembling) them for construction is used for long-chain DNA construction because, for example, the length of a DNA that can be supplied by chemical synthesis is as short as about 200 bases. For this kind of method for assembling DNA fragments, various methods including OGAB method (Patent Literature 1: Japanese Laid-Open Publication No. 2004-129654, Non Patent Literature 1: Tsuge, K., et al., Nucleic Acids Res. 31, e133 (2003)), SLIC method (Non Patent Literature 2: Li M Z, Elledge S J (2007) Nature Methods 4:251-256), Golden Gate method (Non Patent Literature 3: Engler, C. et al. PLoS ONE (2008)), Gibson Assembly method (Non Patent Literature 4: Gibson, D. G., et al. Nat. Methods, 6, 343-345. (2009)), LCR method (Non Patent Literature 5: de Kok, S. et al. ACS Synth. Biol. (2014)), gene assembling method of budding yeast (Non Patent Literature 6: Gibson, D. G., et al. Proc. Nat. Acad. Sci. USA 6, 105, 20404-20409, 2008), and the like have been developed.

In order to easily supply a plurality of types of long-chain DNAs at low cost, it is possible to simultaneously prepare a plurality of short DNA fragments each having a different expression parameter for use in this gene assembling and link them in a combination-manner to create a combinatorial library. A method for constructing a combinatorial library has been developed in the above-described gene assembling method.

In addition, it is necessary to make the genotype of a long-chain DNA correspond to the phenotype thereof in Testing the long-chain DNA combinatorial library supplied by these methods and Learning the direction of the design of expression parameters. There are mainly two methods in conventional construction of a combinatorial library. The first method is constructing one type of long-chain DNA in one gene assembling. In this case, gene assembling with a different material is individually performed as many times as matching to the scale of the combinatorial library. This method has an advantage in that it is possible to quickly grasp the corresponding phenotype even without separately confirming a genotype in Test because it can be grasped beforehand which gene assembling results in which genotype. However, this method has a disadvantage in that it is difficult to enlarge the scale. The second method is mixing all materials to be used in the combinatorial library and constructing a library with one gene assembling. This method has an advantage in that a large-scale combinatorial library can be easily obtained. However, it is necessary to individually confirm the base sequence by sequencing in order to know the genotype of a clone selected from this library, and the longer the chain length of DNA is, the more time it takes to confirm the base sequence. Thus, this method has a problem in that Test is a rate-determining step.

CITATION LIST

Patent Literature

[PL1] Japanese Laid-Open Publication No. 2004-129654 (Japanese Patent No. 4479199)

Non Patent Literature

[NPL 1] Tsuge, K., et al., Nucleic Acids Res. 31, e133, 2003
[NPL 2] Li M Z, Elledge S J, Nature Methods 4:251-256, 2007
[NPL 3] Engler, C. et al. PLoS ONE, 2008
[NPL 4] Gibson, D. G., et al. Nat. Methods, 6, 343-345., 2009
[NPL 5] de Kok, S. et al. ACS Synth. Biol., 2014
[NPL 6] Gibson, D. G., et al. Proc. Nat. Acad. Sci. USA 6, 105, 20404-20409, 2008

SUMMARY OF INVENTION

Technical Problem

Under this circumstance, the problem to be solved by the present invention is to provide a novel preparation method of a DNA fragment for microbial cell transformation by which a long-chain DNA combinatorial library can be efficiently constructed and by which a long-chain DNA combinatorial library for the next DBTL cycle can be quickly prepared even without confirmation of the base sequence, which is a rate-determining step.

Solution to Problem

It is preferable to use a multiple gene fragment assembling technique as described above in order to efficiently construct a long-chain DNA combinatorial library. However, regardless of the type of gene assembling technique, it is important that gene fragments to be assembled are even in amount, in other words, it is important that the molar concentration of each gene fragment is equal. However, it has been difficult to efficiently construct a combinatorial library comprised of many choices by utilizing a gene assembling technique because it has been difficult to adjust the molar concentration of many gene fragments, particularly over 10, to an equal molar concentration.

Gene fragments that are materials for performing gene assembling generally need to be prepared one by one for each fragment. In addition, in integrating these fragments to be at an equal molar concentration, the weight concentration of a DNA is measured and the amount to be added is determined by calculation based on the length of a DNA fragment. However, it was extremely difficult to precisely integrate the fragments to be equimolar due to an error in measurement of a DNA concentration, an error in DNA pipetting, or the like. Meanwhile, when an assembly that is in a plasmid state after being assembled once is cleaved by a restriction enzyme to be reduced to the original material, the resultant material is in an ideal equimolar state. The present inventors found that if this is actually used to perform assembling again, the assembling efficiency is improved by 100-times or greater as compared to the above-described case wherein DNA fragments are manually integrated and assembled (Tsuge, N A R, 2003). Moreover, in the case of an assembly which is cleaved into choice fragments when cleaved by a restriction enzyme, even when the base sequence of the choice fragments is not identified, the presence of actual DNA enables construction of a combinatorial library by mixing the choice fragments with a choice fragment derived from another assembly prepared in the same manner. The present inventors obtained a concept from this result to complete the highly efficient method for constructing a long-chain DNA combinatorial library of the present invention.

Specifically, as a result of diligent research to solve the above-described problem to be solved, the present inventors adopted the above-described method so that all the ratios between the molar concentrations of DNA fragments that are used for assembling for a combinatorial library are as close to 1 as possible in a gene assembling method utilizing the plasmid transformation system of *Bacillus subtilis* (OGAB method). Specifically, choice gene fragments to be combinatorialized are linked to be a string to construct a seed plasmid. In addition, other seed plasmids are constructed for other choice gene fragments to prepare seed plasmids, whose number of types is the same as the maximum number of choices. Cleaving each seed plasmid by a restriction enzyme gives a solution in which the gene fragments are mixed in an equimolar state. Equimolarity of this solution is maintained even when it is mixed with another seed plasmid. Various gene fragments contained in such solution are then linearly linked to give a polymeric DNA in a pseudo-tandem repeat state in which a plasmid vector portion periodically appears, and this DNA is used to transform *Bacillus subtilis*. A combinatorial library is efficiently constructed by circularization in the body of *Bacillus subtilis* utilizing homology to the plasmid vector portion.

This method has a feature in that gene fragments at an equal molar concentration necessary for construction of a combinatorial library can be very easily and certainly prepared and the scale of the library construction can be enlarged more than ever before. In addition, with this method, a long-chain DNA combinatorial library of the next cycle can be constructed even without confirming the genotype of the obtained plasmid. Specifically, the present invention is summarized as follows.

[1] A preparation method of a DNA fragment for microbial cell transformation, the DNA fragment having at least one insert DNA unit comprising: a DNA comprising a replication origin effective in a host microorganism; and an insert DNA in which unit DNAs are linked, characterized in that the method comprises:

(A) preparing a plurality of types of plasmids by OGAB method, wherein the plasmids comprise an insert DNA unit in which a plurality of types of unit DNAs capable of being linked in a specific linking order are linked;

(B) processing the plurality of types of plasmids prepared in step (A) with a restriction enzyme suitable for each plasmid to cleave the plasmids into unit DNAs and preparing a plurality of types of unit DNA mixture solutions; and (C) re-assembling the unit DNAs by OGAB method using the plurality of types of unit DNA mixture solutions obtained in step (B) to prepare a long-chain DNA fragment.

[2] The preparation method of a DNA fragment for microbial cell transformation of [1], characterized in that all the ratios between molar concentrations for DNA fragments in the unit DNA mixture solutions obtained in step (B) are 0.8 to 1.2.

[3] The preparation method of a DNA fragment for microbial cell transformation of [1] or [2], characterized in that in step (A), the number of types of unit DNAs comprised in one type of insert DNA unit is 3 to 60.

[4] The preparation method of a DNA fragment for microbial cell transformation of any of [1] to [3], wherein the number of types of the restriction enzymes used in step (B) is three or less.

[5] The preparation method of a DNA fragment for microbial cell transformation of any of [1] to [4], wherein the restriction enzyme is a restriction enzyme that produces an overhang end.

[6] A plasmid comprising a DNA fragment for microbial cell transformation obtained by the preparation method of any of [1] to [5].

[7] A preparation method of a DNA fragment for microbial cell transformation, the DNA fragment having at least one insert DNA unit comprising: a DNA comprising a replication origin effective in a host microorganism; and an insert DNA in which unit DNAs are linked, characterized in that the method comprises:

(B') processing the plurality of types of plasmids of [6] with a restriction enzyme suitable for each plasmid to cleave the plasmids into unit DNAs and preparing a plurality of types of unit DNA mixture solutions; and (C) re-assembling the unit DNAs by OGAB method using the unit DNA mixture solutions obtained in step (B') to prepare a long-chain DNA fragment.

[8] The preparation method of a DNA fragment for microbial cell transformation of [7], characterized by selecting a plurality of types of plasmids comprising the obtained long-chain DNA fragment and reusing the plasmids as the plasmids in step (B').

[9] A method for constructing a chimeric plasmid library, using the preparation method of a DNA fragment for microbial cell transformation of any of [1] to [5], [7], and [8].

Advantageous Effects of Invention

According to the present invention, it is possible to quickly and efficiently construct a long-chain DNA combinatorial library. It is also possible to reuse a plurality of plasmids which are selected from the same library and whose base sequences have not been confirmed for construction of a new chimeric library.

BRIEF DESCRIPTION OF DRAWINGS

FIG. 2 shows the detailed structure of a unit DNA constituting an insert unit.

FIG. 5 shows the direction of a unitary gene in each plasmid in the first chimeric plasmid library obtained by the method of the present invention and the isobutanol production.

DESCRIPTION OF EMBODIMENTS

Figure 1:
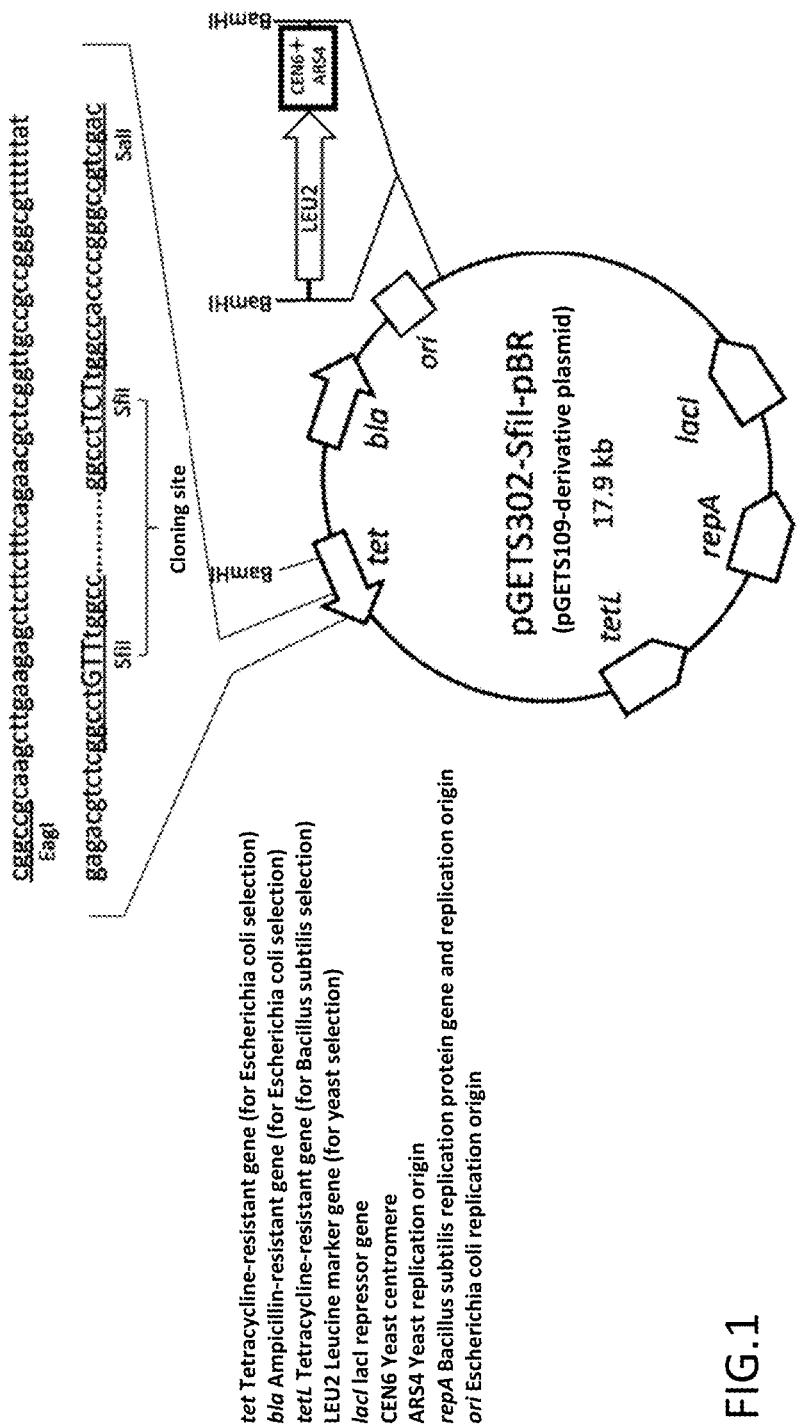
FIG. 1 shows the structure of pGETS302—SfiI-pBR, which is a plasmid vector for assembling.

The present invention is hereinafter described in detail. As used herein, a molecular biological approach can be performed by a method described in general experiment manuals known to those skilled in the art or a method equivalent thereto, unless specifically and explicitly noted otherwise. Further, the terms used herein are understood in the meaning that is commonly used in the art, unless specifically noted otherwise.

<Preparation Method of a DNA Fragment for Microbial Cell Transformation>

The present invention relates to a novel preparation method of a DNA fragment for microbial cell transformation by which a long-chain DNA combinatorial library can be efficiently constructed and by which a new combinatorial library can be easily constructed even without confirmation of the genotype of the resulting clone. Specifically, said preparation method is a preparation method of a DNA fragment for microbial cell transformation having at least one insert DNA unit comprising: a DNA comprising a replication origin effective in a host microorganism; and an insert DNA in which unit DNAs are linked, characterized in that the method comprises:

(A) preparing a plurality of types of plasmids by OGAB method, wherein the plasmids comprise an insert DNA unit in which a plurality of types of unit DNAs capable of being linked in a specific linking order are linked;

(B) processing the plurality of types of plasmids prepared in step (A) with a restriction enzyme suitable for each plasmid to cleave the plasmids into unit DNAs and preparing a plurality of types of unit DNA mixture solutions; and (C) re-assembling the unit DNAs by OGAB method using the plurality of types of unit DNA mixture solutions obtained in step (B) to prepare a long-chain DNA fragment.

The present invention is a method wherein a DNA (plasmid vector) comprising a replication origin effective in a host microorganism and an insert DNA unit comprising an insert DNA are prepared as a plurality of unit DNAs having a structure in which they can be alternately linked, the unit DNAs are linked to create a DNA fragment that has at least one insert DNA unit and has at least two unit DNAs that are identical, co-culture with the DNA fragment and a competent cell of the host microorganism is then performed, a plasmid DNA is collected from the microorganism to prepare a combinatorial library, and a plasmid DNA selected from the combinatorial library can be utilized as a seed plasmid of a new library.

In the present invention, an insert DNA unit refers to a unit that comprises: a DNA comprising a replication origin effective in a host microorganism; and an insert DNA. A DNA fragment for microbial cell transformation comprises one or more insert DNA units. Furthermore, the insert DNA unit can comprise an appropriate base sequence as required in addition to a DNA comprising a replication origin effective in a host microorganism and an insert DNA. For example, when a plasmid for expressing a gene comprised in an insert DNA is created by the method of the present invention, the insert DNA unit may comprise a base sequence that controls transcription and translation such as promoters, operators, activators, or terminators. Specifically, a promoter used when yeast is a host includes a promoter for a primary metabolite of a glycolysis system and the like.

In the present invention, a DNA comprising a replication origin effective in a host microorganism can be any DNA as long as the DNA is replicated in a microorganism that can be transformed with a created DNA fragment. Bacteria that belong to the genus *Bacillus* are used as the host microorganism of the present invention. Examples of a specific microorganism and a DNA comprising a replication origin effective in the microorganism include *B. subtilis* (*Bacillus subtilis*) and a DNA having a θ-type replication mechanism, which specifically includes a sequence of a replication origin or the like comprised in a plasmid such as pTB19 (Imanaka, T., et al. J. Gen. Microbioi. 130, 1399-1408. (1984)) or pLS32 (Tanaka, T and Ogra, M. FEBS Lett. 422, 243-246. (1998), pAMβ1 (Swinfield, T. J., et al. Gene 87, 79-90. (1990)).

In the present invention, an insert DNA refers to a DNA to be cloned, and the type and the size thereof are not particularly limited. The DNA may be any type of DNA which is not only a natural sequence of a prokaryote, a eukaryote, a virus or the like but also an artificially designed sequence. The type of the DNA is not particularly limited. Preferably, the DNA includes a gene group constituting a series of metabolic pathways, an antisense RNA gene group intended to deactivate gene expression present in a host genome, a mixture of both a metabolic pathway gene group and an antisense RNA group, and the like. The insert DNA of the present invention has a structure in which unit DNAs are linked.

In the present invention, unit DNAs have a structure in which they can be repeatedly linked to each other while keeping the order. Unit DNAs that are linked in order constitute a DNA fragment that is one insert DNA. The DNA chain length of a unit DNA fragment is not particularly limited. Being linked to each other while keeping the order means that unit DNAs having sequences adjacent to each other on an insert DNA are bound while keeping the order and direction. Further, being repeatedly linked means that the 5' terminal of a unit DNA having the base sequence of the 5' terminal of an insert DNA and the 3' terminal of a unit DNA having the base sequence of the 3' terminal of the insert DNA are bound. Specific examples of such unit DNAs include DNA fragments having terminals that can be repeatedly linked to each other while keeping the order by utilizing complementarity between base sequences in overhang ends of the fragments. The structure of this overhang, including a difference in the shape of overhang between the 5' terminal overhang and the 3' terminal overhang, is not particularly limited as long as it is not a palindromic structure (palindrome). In this regard, it is preferable that an overhang end can be created by digestion with a restriction enzyme in creating a unit DNA. If an enzyme capable of recognizing a specific sequence and creating an overhang end of any sequence near the recognized sequence is used as a restriction enzyme, overhang ends of unit DNA fragments can be different at each linking site, so that the linking order is maintained. Examples of such a restriction enzyme include TALEN and ZNF that are artificial restriction enzymes or CRISPR technique-related enzymes capable of creating an overhang end such as CRISPR-Cpf1 and the like in addition to general restriction enzymes used for molecular biology. It is preferable to use a Type II restriction enzyme such as AarI, AlwNI, BbsI, BbvI, BcoDI, BfuAI, BglI, BsaI, BsaXI, BsmAI, BsmBI, BsmFI, BspMI, BspQI, BtgZI, DraIII, FokI, PflMI, SfaNI, or SfiI.

Regarding the number of types of restriction enzyme used for creating an overhang end, cleavage by one type of restriction enzyme is preferred for cutting out one unit DNA. Not all unit DNAs necessarily need to be obtained by digestion with the same type of restriction enzyme. However, it is better that the total number of types of restriction enzyme used is smaller, wherein three or less types are preferable, two or less types are more preferable, and one type is even more preferable.

One or more unit DNAs among unit DNAs constituting an insert DNA unit need to comprise a replication origin effective in a host cell. The rest of the unit DNAs are elements constituting a contiguous base sequence such as a metabolic pathway cluster, a part or the whole of a contiguous genome sequence of an organism, an artificial gene, or an artificial gene circuit, and there is no limitation that a single unit DNA must match a biologically functional unit.

A method for creating a unit DNA may be any method as long as it can create the unit DNA of the present invention. For example, a DNA fragment amplified by a polymerase chain reaction (PCR) using a primer added with a restriction enzyme recognition sequence that produces each overhang end in a base sequence on a template DNA, or a chemically synthesized DNA fragment incorporating a restriction enzyme recognition sequence to produce any overhang sequence at the end beforehand or the like is cloned into a plasmid vector, and used after the base sequence is confirmed. Each unit DNA is designed to be linked in a specific order to eventually provide a desired DNA fragment for microbial cell transformation. The number (type) of unit DNAs that are linked to constitute an insert DNA of interest is 3 to 60 (types), preferably 5 to 50 (types), more preferably 8 to 25 (types), and even more preferably 10 to 20 (types).

Each step of the preparation method of a DNA fragment for microbial cell transformation of the present invention is hereinafter described in detail.

[Step (A)]

In step (A) in the preparation method of a DNA fragment for microbial cell transformation of the present invention, a so-called seed plasmid is prepared. The seed plasmid needs to have a structure wherein an appropriate restriction enzyme recognition sequence is introduced at or near a border between unit DNAs in accordance with each design so that the plasmid after construction of an assembly can be divided into unit DNA fragments in consideration of step (B) and step (C). It is preferable to use an enzyme capable of creating an overhang end of any sequence such as AarI, AlwNI, BbsI, BbvI, BcoDI, BfuAI, BglI, BsaI, BsaXI, BsmAI, BsmBI, BsmFI, BspMI, BspQI, BtgZI, DraIII, FokI, PflMI, SfaNI, or SfiI as a restriction enzyme. A plurality of overhang sequences obtained by processing with these restriction enzymes need to be unique sequence in a single seed plasmid. Further, a seed plasmid group needs to share the same overhang sequence in the same chain and in the same order in a recombination unit in a combinatorial library (although a unit DNA often matches said unit, the recombination unit may be comprised of a plurality of unit DNAs in some seed plasmids).

In constructing an OGAB seed plasmid, specifically, it is also possible to create a DNA fragment for microbial cell transformation by linking (ligation) using a DNA ligase or the like in unit DNA mixture solutions in which each of the above-described unit DNAs is adjusted to be almost equimolar. In this regard, the starting material for gene assembling is not limited to only each of the above-described unit DNAs. An assembly prepared by any assembling method can be utilized as long as it eventually has a structure capable of being divided into each unit DNA as described above. In this case, being almost equimolar means that all the ratios between molar concentrations for DNA fragments in the unit DNA mixture solutions are within the range from 0.8 to 1.2, preferably within the range from 0.9 to 1.1, more preferably within the range from 0.95 to 1.05, even more preferably 1.0. All the ratios between molar concentrations for DNA fragments in the unit DNA mixture solutions being within the above-described numerical value range can be also rephrased as the value obtained by dividing the highest value of the concentration of the unit DNAs comprised in the unit DNA mixture solutions by the lowest value being within the range from 1.0 to 1.5, being within the range from 1.0 to 1.2, being 1.0 to 1.1, or being 1.0.

The unit DNA of the seed plasmid prepared in this step may be any form such as a gene cluster, a gene, or a gene fragment.

Although a method for linking unit DNAs is not particularly limited, it is preferable to perform linking in the presence of a polyethylene glycol and a salt. A salt of a monovalent alkali metal is preferred as the salt. Specifically, it is more preferable to perform linking in a ligation reaction solution comprising 10% polyethylene glycol 6000 and 250 mM sodium chloride. In addition, although the concentration of each unit DNA in a reaction solution is not particularly limited, it is preferable that each unit DNA has a concentration of 1 fmol/µL or greater and is equimolar. Although the enzyme, the reaction temperature, and the time of ligation are not particularly limited, ligation with T4DNA polymerase at 37° C. for 30 minutes or more is preferred.

A host microorganism for the DNA fragment for microbial cell transformation of the present invention is not particularly limited as long as it has natural transformation ability. Such a microorganism includes a microorganism that has natural transformation ability to process a DNA to a single-stranded DNA to take up the DNA and the like. Specifically, bacteria that belong to the genus *Bacillus*, bacteria that belong to the genus *Streptococcus*, bacteria that belong to the genus *Haemophilus*, bacteria that belong to the genus *Neisseria*, and the like are included. Furthermore, bacteria that belong to the genus *Bacillus* include *B. subtilis* (*Bacillus subtilis*), *B. megaterium* (*Bacillus megaterium*), *B. stearothermophilus* (*Bacillus stearothermophilus*), and the like. The most preferred microorganism among them includes *Bacillus subtilis* having excellent natural transformation ability and recombination ability.

A known method suitable for each microorganism can be selected as a method for making a microbial cell competent. Specifically, for example, it is preferable to use a method described in Anagnostopoulou, C. and Spizizen, J. J. Bacteriol., 81, 741-746 (1961) for *Bacillus subtilis*. Further, a known method suitable for each microorganism can be used as a method for transformation. The liquid quantity of a ligation product given to a competent cell is also not particularly limited. The quantity is preferably from 1/20 to an equal quantity, and more preferably a half quantity relative to a competent cell culture. A known method also can be used as a method for purifying a plasmid from a transformant.

It can be confirmed that a plasmid obtained by the above-described method has an insert DNA of interest by a size pattern of a fragment generated by restriction enzyme cleavage, PCR method, or a sequencing method. Further, when the insert DNA has a function such as substance production, confirmation can be made by detecting the function.

For adjustment of a seed plasmid used in construction of a combinatorial library, any method can be used as long as it is a common method for purifying a circular plasmid. A method with reduced risk of contamination of a DNA other than a plasmid DNA is desirable. Specifically, a cesium chloride-ethidium bromide density-gradient ultracentrifugation method is preferred.

[Step (B)]

This step is processing the plurality of types of plasmids (seed plasmids) prepared in step (A) with a restriction enzyme suitable for each plasmid to cleave the plasmids into unit DNAs and preparing a plurality of types of unit DNA mixture solutions. The plurality of types of plasmids (seed plasmids) prepared in step (A) are purified to high purity and then cleaved into unit DNAs. For cleavage into unit DNAs, an appropriate restriction enzyme can be selected depending on the design in step (A).

Regarding the number of types of restriction enzyme used for creating an overhang end, cleavage by one type of restriction enzyme is preferred for cutting out one unit DNA. Not all unit DNAs necessarily need to be obtained by digestion with the same type of restriction enzyme. However, it is better that the total number of types of restriction enzyme used is smaller, wherein three or less types are preferable, two or less types are more preferable, and one type is even more preferable.

The unit DNA mixture solutions obtained in this step are free of DNA fragment other than the plasmid because the seed plasmids are purified to extremely high purity. A prepared long-chain DNA is cleaved with a restriction enzyme and the restriction enzyme is removed, whereby DNA fragment solutions (unit DNA mixture solutions) in which all the ratios between the molar concentrations for DNA fragments are extremely close to 1 can be obtained.

[Step (C)]

This step is re-assembling the unit DNAs by OGAB method using the plurality of types of unit DNA mixture solutions obtained in step (B) to prepare a long-chain DNA fragment. It is possible to more efficiently perform gene assembling by performing a gene assembling method (OGAB method) using the DNA fragment solutions (unit DNA mixture solutions) obtained in step (B) in which all the ratios between the molar concentrations for DNA fragments are extremely close to 1 as a starting material. The explanation in step (A) can be applied to a method for re-assembling the unit DNAs by OGAB method using the unit DNA mixture solutions in this step.

Furthermore, the present invention also includes a preparation method of a DNA fragment for microbial cell transformation, the DNA fragment having at least one insert DNA unit comprising: a DNA comprising a replication origin effective in a host microorganism; and an insert DNA in which unit DNAs are linked, characterized in that the method comprises:

(B') processing the plurality of types of plasmids prepared by the above-described method of the present invention with a restriction enzyme suitable for each plasmid to cleave the plasmids into unit DNAs and preparing a plurality of types of unit DNA mixture solutions; and (C) re-assembling the unit DNAs by OGAB method using the unit DNA mixture solutions obtained in step (B') to prepare a long-chain DNA fragment.

A plurality of types of plasmids comprising the long-chain DNA fragment obtained by the above-described method of the present invention can be selected and reused as the plasmids in step (B').

The present invention also includes a plasmid comprising the DNA fragment for microbial cell transformation obtained by the above-described preparation method of the present invention. The present invention also includes a method for constructing a chimeric plasmid library using the preparation method of the present invention.

EXAMPLES

The present invention is specifically described in the following Examples. However, the present invention is not limited by these Examples.

The common test method or the like such as reagents used in the Examples is as follows.

RM125 strain (Uozumi, T., et al. Moi. Gen. Genet., 152, 65-69 (1977)) and its derivative strain, BUSY9797 strain, were used as a host of *Bacillus subtilis*. As a plasmid vector capable of being replicated in *Bacillus subtilis*, pGET118 (Kaneko, S., et al. Nucleic Acids Res. 31, e112 (2003)) was used. Carbenicillin, which is an antibiotic, was purchased from Wako Pure Chemical Industries. Tetracycline, which is an antibiotic, was purchased from Sigma. SfiI and BspQI, which are restriction enzymes, were purchased from NEB. T4 DNA Ligase was purchased from Takara Bio. Takara Ligation Kit (Mighty) (Takara Bio) was used for common ligation for constructing a plasmid of *Escherichia coli*. KOD plus polymerase of TOYOBO was used for a PCR reaction for preparation of a unit DNA. Meanwhile, Ex-Taq HS manufactured by Takara Bio was used for colony PCR for sequencing a DNA cloned into a plasmid. pMD-19 (simple) was purchased from Takara Bio. For Plasmid Safe, which is an enzyme for purifying a circular plasmid, a product manufactured by EPICENTER was used. 2-Hydroxyethyl agarose, which is a low melting point agarose gel for DNA electrophoresis, was purchased from Sigma. UltraPure Agarose of Invitrogen was used for other common agarose gels for electrophoresis. Phenol:chloroform:isoamyl alcohol 25:24:1 and TE saturated phenol (containing 8-quinolinol) manufactured by Nacalai Tesque were used. Lysozyme was purchased from Wako Pure Chemical Industries. A medium component of an LB medium and agar manufactured by Becton Dickinson were used. IPTG (isopropyl s-D-thiogalactopyranoside) manufactured by Wako Pure Chemical Industries was used. For all other medium components and biochemical reagents, products manufactured by Wako Pure Chemical Industries were used.

Either of *Escherichia coli* DH5α strain, JM109 strain, or TOP10 strain was used for constructing a plasmid which is not specifically noted. QIAprep Spin Miniprep Kit of Qiagen was used for purification of a small amount of a constructed plasmid from *Escherichia coli* while QIAfilter Midi Kit of Qiagen was used for purification of a large amount. MinElute Reaction Cleanup Kit of Qiagen or QIAquick PCR purification Kit of Qiagen was used for DNA cleanup from an enzyme reaction solution. MinElute Gel Extraction Kit of Qiagen was used for purification from a gel block obtained after separation on ordinary agarose gel electrophoresis. As an ultratrace spectrophotometer, nanodrop 2000 of Thermo was used. 3130xl genetic analyzer, which is a fluorescent automatic sequencer manufactured by Applied Biosystems, was used for sequencing.

Other common DNA manipulations were performed according to a standard protocol (Sambrook, J., et al., Molecular Cloning: A Laboratory Manual. Cold Spring Harbor Laboratory Press, Cold Spring Harbor, N.Y. (1989)). *Bacillus subtilis* transformation and plasmid extraction by OGAB method or the like were performed according to a known method (Tsuge, K., et al., Nucleic Acids Res. 31, e133. (2003)).

1. Preparation of an Insert DNA Unit
(1) Construction of a Plasmid Vector for Assembling pGETS302—SfiI-pBR, a plasmid vector for assembling, is an *Escherichia coli*-*Bacillus subtilis*-yeast shuttle plasmid vector that has a replication origin of pBR322 of *Escherichia coli*, repA, which is a replication origin functional in *Bacillus subtilis*, and ARS4 and CEN6 capable of being replicated in budding yeast. This is a plasmid constructed through multi-stage processes based on pGETS109 (Tsuge, et. al., Nucleic Acids Res., 31, e133. (2003)). FIG. 1 shows the structure thereof, and SEQ ID NO: 1 shows the base sequence thereof. The cloning site for the gene to be assembled is between two SfiI cleavage sites, and the largest 15 kb SfiI fragment is used in assembling. Ampicillin was used for selection in *Escherichia coli*. Sterile water was added to 5 μg of this plasmid so that the total volume was 40 μl, followed by adding 5 μl of 10×NEB2.1 Buffer attached to the restriction enzyme and 5 μl of SfiI (NEB), restriction enzyme, and causing the mixture thereof to react at 50° C. for 2 hours. The resultant liquid was subjected to separation by low melting point agarose gel electrophoresis, an about 15 kb fragment of the vector body was then cut out from the gel, a DNA fragment of interest was purified, the DNA fragment was then dissolved into 20 μl TE, 1 μl of the solution was collected and the concentration thereof was measured by an ultratrace spectrophotometer.

(2) Method for Designing a Unit DNA Overhang Sequence

As unit DNAs constituting one insert unit, there are 14 fragments in total including pGETS302, which is a vector for assembling, as shown in FIG. 2. There are 12 genes in total constituting a group involved in an isobutanol metabolic pathway in budding yeast. These genes are defined as the 1st to the 12th unit DNA in order. kanMX4, which acts as a selection marker for transformation in budding yeast, is defined as the 13th unit DNA, and an assembling vector is defined as the 14th unit DNA. The 1st to 14th unit DNAs are contiguous in the same order as the number and form a structure in which the 14th unit DNA and the 1st unit DNA are linked, thereby forming one insert unit. The terminal of each unit DNA has a unique 3-base 3' terminal overhang bases which are designated for each number of unit DNA on each of the left and right of the fragment. With this complementarity, a linking partner is designated. The specific configuration is as follows. (14th unit DNA)-GTT-(1st unit DNA)-TGA-(2nd unit DNA)-CGA-(3rd unit DNA)-TGT-(4th unit DNA)-GAT-(5th unit DNA)-TTG-(6th unit DNA)-GTC-(7th unit DNA)-ATG-(8th unit DNA)-TGG-(9th unit DNA)-TAG-(10th unit DNA)-ACT-(11th unit DNA)-GTA-(12th unit DNA)-CTT-(13th unit DNA)-TCT-(14th unit DNA).

2. Regulation of a Gene Expression Level of Budding Yeast Isobutanol-Producing Gene Group
(1) Budding Yeast Budding yeast (*Saccharomyces cerevisiae*) is a eukaryotic microorganism. Research on budding yeast has been advanced as a eukaryotic model microorganism, its genome sequence has been completely revealed, and various information has been accumulated. Budding yeast performs alcohol fermentation as anaerobic respiration. Budding yeast has been utilized for fermentation of beer, wine, Japanese sake or the like for a long time, and has been widely used as a host for bioethanol production because of its high ethanol production ability. Currently, budding yeast is also widely used for industrial purposes as a host for production of a useful substance other than ethanol, and is also utilized for production of an added value product such as dyes, perfumes, or supplements in addition to higher alcohols having three or more carbons chain or various organic acids. Unlike a bacterium, which is a prokaryote, budding yeast, which is a eukaryote, has an organelle such as a mitochondrion or a nucleus. Further, since budding yeast is generally in a monocistronic expression format instead of a polycistronic expression format, one promoter is required for one gene. For example, 12 promoters are required to express 12 genes.

(2) Isobutanol Metabolic Pathway Design

Figure 3:
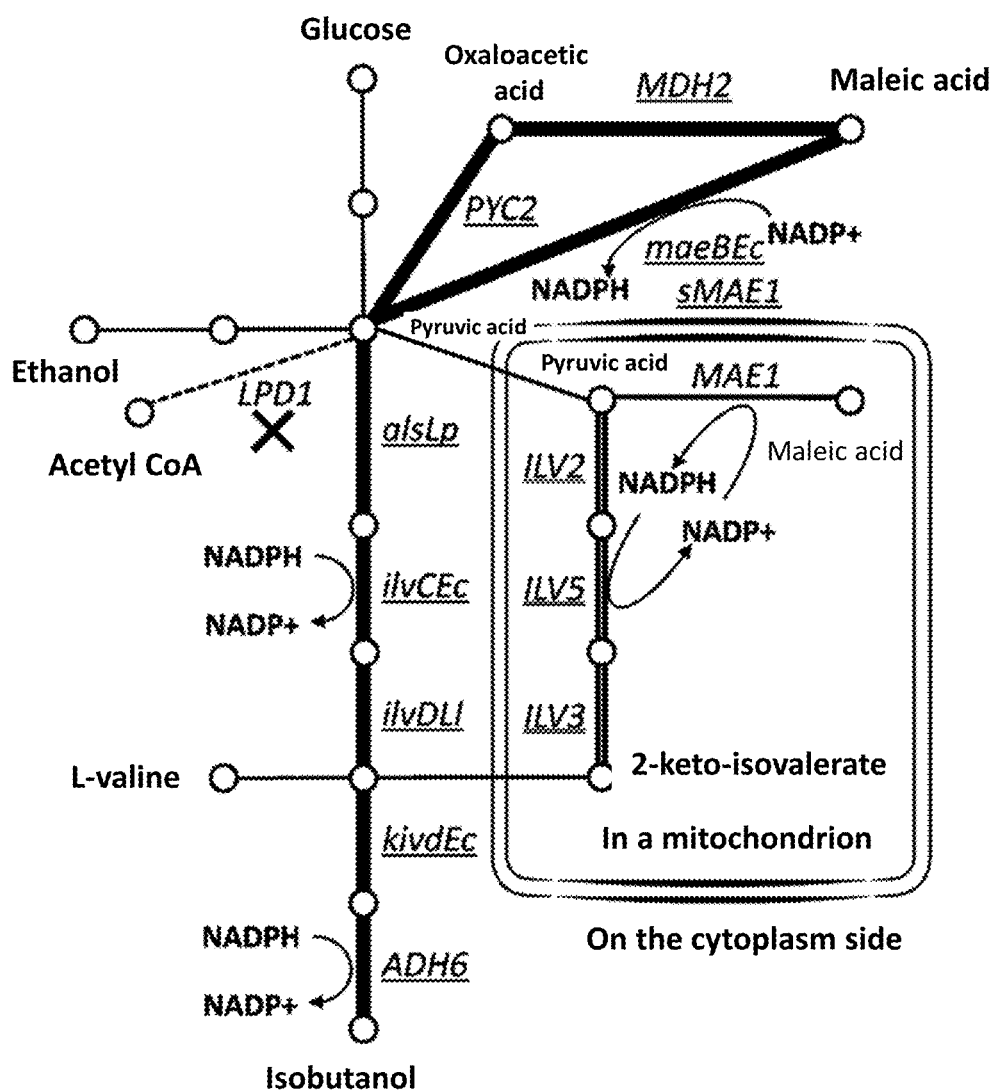
FIG. 3 shows an artificial metabolic pathway of budding yeast which is designed to highly produce isobutanol.

The main application of isobutanol is as an organic synthesis solvent, a paint remover, and a raw material of i-butyl methacrylate. In addition, isobutanol can be converted to isobutylene by dehydration, can be utilized as a raw material of a fuel mixture agent or a bio jet fuel such as ethyl tert-butyl ether (ETBE), and can be further utilized as a raw material of various polymers by conversion of isobutylene to isooctene (diisobutylene). Although budding yeast originally produces ethanol as a main product, budding yeast slightly produces isobutanol as fusel alcohol. FIG. 3 shows an artificial metabolic pathway of budding yeast which is designed to highly produce isobutanol. If two genes (e.g., kivd derived from *Lactococcus lactis* and ADH6 derived from budding yeast) encoding a keto-acid decarboxylase (KDC) and an alcohol dehydrogenase (ADH) are introduced to 2-keto-isovalerate in the L-valine metabolic pathway in budding yeast, isobutanol production is increased. Thus, these genes were added to the subject of assembling. However, isobutanol cannot be efficiently produced due to a plurality of causes such as 2-keto-isovalerate that is a substrate being originally produced in the mitochondrion or NADPH required by a ketol-acid reductoisomerase (ILV5) and ADH6 being deficient. Thus, three genes encoding an acetolactate synthase (ILV2), a ketol-acid reductoisomerase (ILV5), and a dihydroxy acid dehydratase (ILV3) constituting the pathway from pyruvic acid to 2-ketoisovalerate (the metabolic pathway indicated by a double line in FIG. 3) which is performed in the mitochondrion, and a malic enzyme (MAE1) for adjusting NADPH in the mitochondrion, i.e., four genes in total (the genes indicated by a double underline in FIG. 3), were added to the subject of assembling for the purpose of enhancing the expression of those genes. Furthermore, three genes of ilv2CEc, ilvDL1 and alsLp were added to the subject of assembling so that the metabolic pathway of the above genes is also constructed on the cytoplasm side, and three genes of a carbonic acid fixing enzyme (PYC2), a malic dehydrogenase (MDH2), and sMAE1 from which a mitochondrial localization signal of the N terminal of a malic enzyme (MAE1) is removed were added to the subject of assembling in order to solve the deficiency in NADPH in the cytoplasm, in other words, six genes in total (the genes indicated by a single underline in FIG. 3) were added to the subject of assembling. The above-described 12 genes were each introduced with a promoter and a terminator of a primary metabolic pathway capable of being strongly expressed in yeast.

(3) Seed Plasmid 1: Design of an Overexpressing Gene Group Set

Expression cassettes using 12 types of promoters and terminators were designed so that 12 genes can be expressed in budding yeast. Specifically, promoters and terminators of ADH1, FBA1, HXT7, PDC1, PGK1, SED1, TDH1, TDH2, TDH3, TEF1, TEF2, and TPI1 were used to design 12 types of expression cassettes (the arrows on the gene ORF in FIG. 4 indicate the promoter sequence while the pins indicate the terminator sequence). A sequence ( . . . atgAGAAGAGCTCTTCAtaa . . . ) in which two BspQI sites are reversely placed was added between the promoter and the terminator of each expression cassette so that the portion from the start codon (ATG) to the stop codon (TAA) of a gene to be inserted can be subcloned. For PDC1 promoter and TDH2 promoter, a sequence in which G in position −492 was mutated to C and a sequence in which C in position −462 was mutated to G were used for PDC1 promoter and TDH2 promoter, respectively, in order to delete the BspQI sites contained in the sequence. A restriction enzyme site (SfiI site) designed such that a unique 3-base 3' terminal overhang designated for each number of a unit DNA appears after cleavage with SfiI was added to the left and right terminal sequences of the 12 types of expression cassettes comprising a promoter and a terminator, and the sequence was designed such that a linking partner is designated by complementarity. These expression cassettes comprising 12 types of promoters and terminators were designed to be cloned into a pMA or pMK vector. Next, ilvEc, ilvDL1, alsLp, kivd, ILV3, ILV5, ADH6, PYC2, ILV2, MDH2, maeBEc, and sMAE1 were selected as 12 genes constituting a group involved in an isobutanol metabolic pathway in budding yeast, and the sequence was modified so that the start codon and the stop codon of each gene were unified to ATG and TAA, respectively. These genes were also designed to be added with a sequence (TAGGCTCTTCAatg . . . taaAGAAGAGCCTA) in which a BspQI site is placed at both terminals so that these genes can be subcloned to any of the 12 types of expression cassettes (FIG. 2). These genes having a BspQI site at both terminals were designed so as to be cloned into a pCR-BluntII-TOPO vector. Finally, 12 types of overexpression cassettes in total (ilvCEc-1st, ilvDL1-2nd, alsLp-3rd, kindEc-4th, ILV3-5th, ILV5-6th, ADH6-7th, PYC2-8th, ILV2-9th, MDH2-10th, maeBEc-11th, and sMAE1-12th) were designed (SEQ ID NOs: 2 to 13) so that ilvEc, ilvDL1, alsLp, kivd, ILV3, ILV5, ADH6, PYC2, ILV2, MDH2, maeBEc, or sMAE1 would be inserted to each of the BspQI sites of the 12 types of expression cassettes having the promoters and terminators of ADH1, FBA1, HXT7, PDC1, PGK1, SED1, TDH1, TDH2, TDH3, TEF1, TEF2, and TPI1 cloned into pMA or pMK. In addition, a KanMX fragment (kanMX4-13th) was introduced as the 13th fragment (SEQ ID NO: 14) to enable selection with an agent in budding yeast.

(4) Seed Plasmid 2: Design of an Expression Suppressing Gene Group Set

Although the same promoter and terminator sequence was used while following (3) Seed plasmid 1: design of an overexpressing gene group set, an ORF fragment of each gene to be inserted was designed to be in an opposite direction relative to the overexpression gene group set. Specifically, the plasmid configured to be able to subclone the portion from the start codon (ATG) to the stop codon (TAA) of a gene to be inserted between the promoter and the terminator of each expression cassette which was designed in (3) was cleaved by BspQI and a sequence in which two BspQI sites are reversely placed is newly linked thereto, whereby a plasmid with a changed overhang sequence (the underlined sequence of . . . atgttaAGAAGAGCTCTTCA cattaa . . . ) was prepared. The base sequences of the expression suppressing cassettes (ilvCEc-as-1st, ilvDL1-as-2nd, alsLp-as-3rd, kindEc-as-4th, ILV3-as-5th, ILV5-as-6th, ADH6-as-7th, PYC2-as-8th, ILV2-as-9th, MDH2-as-10th, maeBEc-as-11th, and sMAE1-as-12th) created through these processes are shown in SEQ ID NOs: 15 to 26. Regarding a unit DNA, the unit DNAs of seed plasmid 2 are consequently longer than the unit DNAs of seed plasmid 1 by six bases of the overhang sequence that were newly introduced. The same marker as seed plasmid 1 was used for KanMX, which is an agent selection marker.

(5) Construction of a Seed Plasmid

A gene (ORF region) was amplified from budding yeast (YPH499 strain) using the PCR method. First, primers in which the restriction enzyme recognition site determined above was added to the 5' terminal of primers for amplifying a DNA sequence between the overhang combinations determined above in a position to cut out a desired overhang and in which the sequence of TAG was further added to the 5' terminal were used. A DNA fragment of a designated region was amplified from the budding yeast genome by using a pair of these primers. The reaction condition of PCR was set by adding, for each reaction (50 µl), 5 µl of KOD Plus 10×buffer Ver. 2, 3 µl of 25 mM $MgSO_4$, 5 µl of dNTP (2 mM each), 1 µl of KOD Plus (1 unit/µl), 48 pg of lambda phage DNA (TOYOBO), 15 pmol of primers (F primer and R primer, respectively), and sterile water, and the reaction was performed with GeneAmp PCR System 9700, Applied Biosystems) according to the following program. After incubation at 94° C. for 2 minutes, 30 cycles each comprised of 98° C. for 10 seconds, 55° C. for 30 seconds, and 68° C. for 1 minute were performed, and final incubation was performed at 68° C. for 7 minutes.

The amplified DNA fragment was applied with a voltage of 100 V (about 8 V/cm) by a general-purpose agarose gel electrophoresis device (i-MyRun.N, electrophoresis system for nucleic acids, Cosmo Bio) and subjected to electrophoresis for 1 hour in the presence of 1×TAE (Tris-Acetate-EDTA Buffer) buffer in 0.7% low melting point agarose gel (2-Hydroxyethyl Agarose TypeVII, Sigma), whereby the plasmid vector and the unit DNAs were separated. This electrophoresis gel was stained with 100 ml of 1×TAE buffer comprising 1 µg/ml of ethidium bromide (Sigma) for 30 minutes and illuminated with an ultraviolet ray with a long wavelength (366 mn) to be visualized, whereby a PCR product having a size of interest was cut out with a razor and collected in a 1.5 ml tube. 1×TAE buffer was added to the collected low melting point agarose gel (about 300 mg) so that the total volume was about 700 µl, which was then kept at a constant temperature of 65° C. for 10 minutes to thereby dissolve the gel. An equal quantity of TE saturated phenol (Nacalai Tesque) was then added and mixed well to deactivate the restriction enzyme. The mixture was separated into a phenol phase and an aqueous phase by centrifugation (20,000×g, 10 minutes), and the aqueous phase (about 900 µl) was collected in a new 1.5 ml tube. 500 µl of 1-butanol (Wako Pure Chemical Industries) was added thereto and mixed well, followed by separation by centrifugation (20,000×g, 1 minute) and removal of water-saturated 1-butanol. This operation was repeated until the volume of the aqueous phase was 450 µl or less, thereby decreasing the volume of the aqueous phase. 50 µl of 3M potassium acetate-acetic acid buffer (pH 5.2) and 900 µl of ethanol were added thereto and centrifugation (20,000×g, 10 minutes) was performed to precipitate the DNA, which was then rinsed with 70% ethanol and dissolved into 20 µl of TE (10 mM Tris-HCl, 1 mM EDTA, pH 8.0). This collected DNA was preserved at −20° C. until it was used.

The obtained DNA fragment was cloned into an *Escherichia coli* plasmid vector by the TA cloning method by the method shown below. 1 µl of 10×Ex-Taq Buffer attached to Ex-Taq, which is an enzyme for PCR reaction of TAKARA, 0.5 µl of 100 mM dATP, and 0.5 µl of Ex-Taq were added to 8 µl of the DNA fragment, and the mixture thereof was kept at a constant temperature of 65° C. for 10 minutes to thereby add an overhang of A to the 3' terminal of the DNA fragment. 1 µl of pMD19-Simple of TAKARA and 3 µl of sterile water were mixed to 1 µl of this DNA fragment solution, 5 µl of TAKATA Ligation (Mighty) Mix was then added thereto, and the mixture thereof was kept at a constant temperature of 16° C. for 30 minutes. 5 µl of this ligation solution was added to 50 µl of chemical competent cells of *Escherichia coli* DH5α, and the mixture thereof was kept at a constant temperature on ice for 15 minutes, was then given a heat shock at 42° C. for 30 seconds, was left on ice for 2 minutes, and was then added with 200 µl of LB medium. The mixture thereof was kept at a constant temperature of 37° C. for 1 hour, was then spread on an LB plate comprising 1.5% agar and comprising carbenicillin at a concentration of 100 µg/ml, and was cultured overnight at 37° C., whereby a transformant of the plasmid was obtained.

The obtained colony was prepared using a reagent for preparing a template DNA for PCR (Cica Geneus® DNA preparation reagent, Kanto Kagaku), Specifically, 2.5 µl of a solution in which reagent a and reagent b in the reagent kit were mixed at a ratio of 1:10 was prepared, and a small quantity of the colony on the plate collected by a toothpick was suspended in the solution, followed by processing the suspension at 72° C. for 6 minutes and then processing it at 94° C. for 3 minutes. 2.5 µl of 10×enzyme for TAKARA Ex-Taq, 2 µl of 2.5 mM dNTP solution, 0.25 µl of 10 pmol/µl of M13F primer, 0.25 µl of 10 pmol/µl of M13R primer, 17 µl of sterile water, and 0.5 µl of Ex-TaqHS were added to the obtained liquid, and the mixture thereof was incubated at 94° C. for 5 minutes, followed by performing 30 cycles each consisting of 98° C. for 20 seconds, 55° C. for 30 seconds, and 72° C. for 1 minute to amplify the DNA. The base sequence of this PCR product was analyzed to study whether it completely matches a desired sequence. Finally, a correct sequence was obtained from all clones.

*Escherichia coli* transformants having a plasmid into which a DNA fragment having a desired sequence was cloned were each cultured in 2 ml of LB medium containing 100 µg/ml of carbenicillin at 37° C. and 120 spm overnight. The obtained microbial body was purified by using QIAfilter Plasmid miniKit (Qiagen) according to the manual. The obtained plasmid was cleaved by BspQI and an ORF region was collected by size fractionation by electrophoresis.

Thermo Fisher was asked to synthesize a DNA (for overexpression of FIG. 2) designed such that DNA fragments in which a promoter and a terminator of yeast are linked at a BspQI site can be cut out at a SfiI site. These DNA fragments were delivered while being cloned into a plasmid vector pAM or pMK. This plasmid was cleaved by BspQI and a BspQI fragment of the above-described ORF was linked thereto to make a construct, which was prepared as a plasmid having the unit DNAs of seed plasmid 1. The sequences of these unit DNA fragments are as shown in SEQ ID NOs: 2 to 13. For seed plasmid 2, the above-described DNA fragments cloned into pMA or pMK in which a promoter and a terminator are linked at a BspQI site were cleaved by BspQI and introduced with a linker DNA, thereby making a new construct as in the construct for expression suppression of FIG. 2. This plasmid was cleaved by BspQI and a BspQI fragment of the above-described ORF was introduced to make a construct. *Escherichia coli* transformants each having these plasmids into which a DNA fragment having a desired sequence was cloned were each cultured in 2 ml of LB medium containing 100 µg/ml of carbenicillin at 37° C. and 120 spm overnight. The obtained microbial body was purified by using QIAfilter Plasmid miniKit (Qiagen) according to the manual. 10 µl of the obtained plasmid was fractionated, 30 µl of sterile water, 5 µl of 10×NEB buffer#2, and 5 µl of SfiI restriction enzyme (NEB) were added thereto, and the mixture thereof was caused to react at 50° C. for 2 hours thereby separating the unit DNA fragments from the plasmid vector. The resulting product was applied with voltage of 50 V (about 4 V/cm) by a general-purpose agarose gel electrophoresis device and subjected to electrophoresis for 1 hour in the presence of 1×TAE buffer in 0.7% low melting point agarose gel, whereby the plasmid vector and the unit DNAs were separated. This electrophoresis gel was stained with 100 ml of 1×TAE buffer comprising 1 µg/ml of ethidium bromide (Sigma) for 30 minutes and illuminated with an ultraviolet ray with a long wavelength (366 mn) to be visualized, whereby a portion around 3 kb was cut out with a razor and collected in a 1.5 ml tube. The collected low melting point agarose gel (about 300 mg) was purified in the above-described manner and dissolved into 20 µl TE. The unit DNA plasmid prepared in this manner was quantified by a fluorescence plate reader for SYBR GreenII, which is a nucleic acid fluorescent dye, using a calibration curve created based on a dilution series of commercially available Lambda phage genome DNA (TOYOBO).

(6) Gene Assembling

11 µl of 2×ligation buffer was added to 10 µl of mixture solution comprising 0.1 fmol or greater of the unit DNAs of SEQ ID NOs: 2 to 14 for assembling of seed plasmid 1 or the unit DNAs of SEQ ID NOs: 14 to 26 for assembling of seed plasmid 2 and pGETS302-SfiI (SEQ ID NO: 1) that is a vector for gene assembling in equimolar amounts. The whole mixture was kept at a constant temperature of 37° C. for 5 minutes, followed by adding 1 µl of T4 DNA ligase (Takara) and keeping the mixture at a constant temperature of 37° C. for 4 hours. 10 µl thereof was collected and subjected to electrophoresis to confirm ligation. Subsequently, 10 µl thereof was collected in a new tube, 100 µl of *Bacillus subtilis* competent cells were added thereto, and the mixture thereof was rotary-cultured by a duck rotor at 37° C. for 30 minutes. Subsequently, 300 µl of LB medium was added, and the mixture thereof was rotary-cultured by a duck rotor at 37° C. for 1 hour, followed by spreading the culture solution on an LB plate containing 10 μg/ml of tetracycline and culturing overnight at 37° C. From the colonies. 100 transformants were obtained for both the overexpression construct and the gene expression suppressing construct. The plasmid was extracted and the pattern of restriction enzyme cleavage was analyzed to select one transformant having a structure of interest (the seed plasmids of step (A) of FIG. 4) fir each of the constructs.

(7) High Purity-Purification of a Seed Plasmid

A plasmid DNA with high purity was supplied by a cesium chloride-ethidium bromide density-gradient ultracentrifugation method. Specifically, 200 ml of an LB medium supplemented with an antibiotic (tetracycline) was prepared, 100 ml of each thereof was placed in a 500 ml conical flask and cultured overnight at 37° C. After sufficient proliferation, 100 μl of 1M IPTG was added to each flask to increase the copy number of the plasmid and the mixture thereof was further cultured for about 3 to 12 hours. After culture was complete, 50 ml of each resulting product was dispensed into four 50 ml tubes (Falcon 2070) and centrifuged at 5,000 rpm for 10 minutes. The supernatant was disposed of, and the bacterial pellet was completely loosened by vortexing. 10 mg/ml of Sol.I solution containing lysozyme (composition: 50 mM glucose, 25 mM Tris-Cl (pH 8.0), and 10 mM EDTA) was prepared, and 2.5 ml of each solution was added to the four tubes containing bacteria and mixed well. The resulting mixture was incubated at 37° C. for 30 minutes. Centrifugation was performed at 5,000 rpm for 10 minutes, the supernatant was removed by decanting, 2.5 ml of Sol.I free of lysozyme was newly added to each of the four tubes, and the pellet was uniformly suspended. Fresh Sol.II (composition: 0.2 N NaOH and 1% (w/v) sodium dodecyl sulfate) was prepared, 5 ml of each solution was added to the four tubes, and the mixture thereof was slowly mixed to make it transparent. 3.75 ml of Sol.III (composition: 60 ml 5M potassium acetate, 11.5 ml glacial acetic acid, and 28.5 ml water) was added to each tube and mixed with strong force to a certain extent so that the White turbid substance could be uniformly dispersed. Centrifugation was performed at 5,000 rpm for 10 minutes, and the supernatant was aspirated with a pipette and transferred to four new 50 ml tubes (Falcon 2070) with a screw cap. 5 ml of phenol/chloroform was added to each tube and mixed hard. Centrifugation was performed at 5,000 rpm for 10 lutes, and the supernatant was aspirated with a pipette and transferred to four new 50 ml tubes (Falcon 2070) with a screw cap. 25 ml of 100% ethanol was added to each of the tubes and mixed, followed by centrifugation at 5,000 rpm for 10 minutes. The supernatant was removed. 2.5 ml of each solution (final concentration of 10 μg/ml) in which 10 μl of 10 mg/ml of RNaseA solution was added to 10 ml of TE was added to each tube and the precipitate was dissolved. The liquid in the four tubes was collected in one tube and incubated for 30 minutes with an incubator with a gas phase at 37° C. After incubation was complete, 5 ml of phenol/chloroform was added and mixed well, followed by centrifugation at 5,000 rpm for 10 minutes. The supernatant was transferred to a new 50 ml tube, 1 ml of Sol.III was added thereto, and 25 ml of 100% ethanol was then added to the mixture and mixed. Subsequently, centrifugation was performed at 5,000 rpm for 10 minutes to remove the supernatant. 5.4 ml of TE was added to the precipitate and completely dissolved. Next, precisely weighed 6.40 g of cesium chloride was placed therein and completely dissolved. Furthermore, 2.6 ml of 1.3 g/ml of cesium chloride solution (solution made by mixing 1.3 g cesium chloride and 1 ml water, in which volumetric adjustment was not performed) was added. Finally, 600 μl of 10 mg/ml of ethidium bromide solution was added and mixed well. One ultracentrifugation tube (Beckman 362181) was prepared and the above mixture was transferred to the ultracentrifugation tube. Water or 1.3 g/ml of cesium chloride solution (with a specific gravity of about 1.5 g/ml) was added to finely adjust the weight so that a difference in weight from the balance would be 20 mg or less. Centrifugation was performed with an ultracentrifugation instrument (Beckman Coulter) under the following condition. Centrifugation was performed at a temperature of 18° C., a rate of 50,000 rpm, an acceleration of Max, and a deceleration of Max for 15 hours or more. After centrifugation was complete, a 1 ml syringe set with a needle (21G×⅝") was prepared and inserted into the ccc-form plasmid band to collect the plasmid solution and transfer it to a 15 ml tube under observation with a ultraviolet ray (365 nm), 500 μl of Sol.III was added thereto, followed by adding water so that the total volume was 3 ml. Furthermore, 9 ml of 100% ethanol was added. Centrifugation was performed at 5,000 rpm for 10 minutes to remove the supernatant. 700 μl of TE was added to the obtained precipitate in the 15 ml tube and the DNA was dissolved. The resulting product was transferred to a 1.5 ml tube, 600 μl of 1-butanol was added thereto and mixed, the mixture thereof was centrifuged at 15,000 rpm for about 10 seconds to separate the mixture into two layers, and the upper butanol layer was disposed of 600 μl of 1-butanol was newly added and mixed, the mixture thereof was centrifuged at 15,000 rpm for about 10 seconds to separate the mixture into two layers, and the upper butanol layer was disposed of. This operation was continued until the water layer was 450 μl or less. 50 μl of Sol.III was added and 900 μl of 100% ethanol was further added. Centrifugation was performed at 15,000 rpm for 10 minutes. The supernatant was disposed of and the precipitate was rinsed with 70% ethanol. The precipitate was dissolved into 22 μl of TE.

(8) Production of a Unit DNA from a Seed Plasmid

Figure 4:
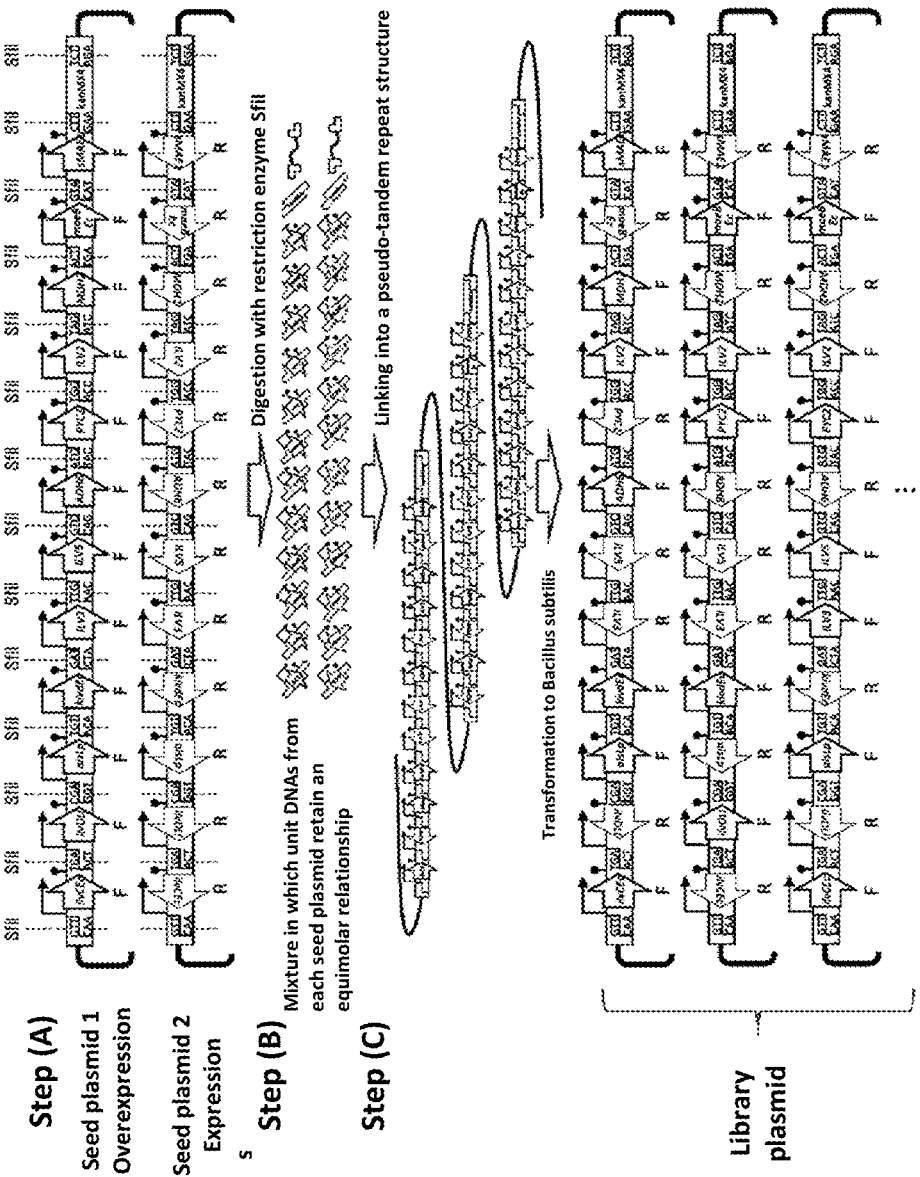
FIG. 4 schematically shows the method for constructing a chimeric plasmid library of the present invention.

Preparation of a unit DNA of step (B) in FIG. 4 was performed in the following manner. 300 ng of the seed plasmid purified to high purity by an ultracentrifugation method was fractionated and diluted to 40 μl with sterile water, 5 μl of 10×NEBbuffer#2 and 5 μl of restriction enzyme SfiI (NEB) were then added, and the mixture thereof was caused to react at 37° C. for 2 hours. 1 μl of the reaction solution was subjected to electrophoresis to confirm cleavage. Subsequently, the reaction solutions of two seed plasmids were integrated, and 450 μl of phenol/chloroform/isoamyl alcohol (25:24:1) (Nacalai Tesque) was added thereto and mixed, followed by separating the mixture thereof into a phenol phase and an aqueous phase by centrifugation (20,000×g, 10 minutes) and collecting the aqueous phase (about 900 μl) in a new 1.5 ml tube. 500 μl of 1-butanol (Wako Pure Chemical Industries) was added thereto and mixed well, followed by separation by centrifugation (20,000×g, 1 minute) and removal of water-saturated 1-butanol. This operation was repeated until the volume of the aqueous phase was 450 μl or less, thereby decreasing the volume of the aqueous phase. 50 μl of 3M potassium acetate-acetic acid buffer (pH 5.2) and 900 μl of ethanol were added thereto and centrifugation (20,000×g, 10 minutes) was performed to precipitate the DNA, which was then rinsed with 70% ethanol and dissolved into 20 μl of TE.

(9) Construction of a Combinatorial Library

Construction of a combinatorial library in step (C) of FIG. 4 was performed in the following manner. The DNA mixture solution obtained in (8) was assembled by the gene assembling method shown in (6) to obtain about 400 transformants. Colonies of 96 strains were randomly selected from the obtained transformants and cultured overnight in an LB medium containing 2 ml of 10 μg/ml of tetracycline. IPTG was added to amplify the copy number of the inside plasmid so that the final concentration was 1 mM, and the mixture thereof was further cultured at 37° C. for 3 hours. Plasmids were extracted from the obtained microbial body. The direction of the gene of each of these extracted plasmids was determined by the PCR method using a primer set shown in SEQ ID NOs: 27 to 62 (FIG. 5). As a result, there were 75 clones having all elements of 12 genes, and a partial loss or an overlap of a unit DNA was found in 21 clones. There were 71 types of different combinations in 75 clones, and an overlap in types was found in 4 clones.

(10) Introduction of a Combinatorial Library to Yeast 96 combinatorial libraries obtained in (9) were introduced to yeast by using a lithium acetate (LiAc) method. Specifically, S. cerevisiae YPH499 strain that is a parent strain was inoculated onto 5 mL of YPDA medium (10 g/L of dried yeast extract [manufactured by Nacalai Tesque], 20 g/L of peptone [manufactured by Becton Dickinson (BD Difco)], 20 g/L of glucose, and 40 mg/L of adenine sulfate) and cultured at 30° C. and at 150 opm overnight. The culture was centrifuged at 3,000 rpm for 5 minutes and the medium was disposed of, followed by suspending the microbial body pellet with 5 mL of sterile distilled water. Furthermore, centrifugation was performed at 3,000 rpm for 5 minutes, the supernatant was then disposed of, and the microbial body pellet was suspended in 1.5 mL of TE/LiAc solution (150 μL of 10×TE, 150 μL of 10×LiAc, and 1,200 μl, of sterile distilled water). 100 μL of the microbial body suspension was transferred to a 1.5 mL Eppendorf tube, 1 to 5 X μL of plasmid DNA (combinatorial library) and 2 μL of Carrier DNA [manufactured by Takara Bio (Clontech)] were added, 600 μL of TE/LiAc/PEG solution (60 μL of 10×TE, 60 μL of 10×LiAc, and 480 μL of 50% PEG3350 solution) was then added, and the mixture thereof was mixed by vortexing for 10 seconds. After the mixture solution was incubated at 30° C. for 30 minutes, 70 μL of dimethyl sulfoxide (DMSO) was added and inverted and mixed, followed by further incubation at 42° C. for 15 minutes. After centrifugation was performed at 14,000 rpm for 5 seconds, the supernatant was completely removed, 250 μL of 100×amino acid stock solution free of L-leucine (4 g/L of adenine sulfate. 2 g/L of L-histidine, 4 g/L of L-tryptophan, 2 g/L of uracil, and 3 g/L, of L-lysine) was added, the microbial body pellet was suspended, and 550 μL of sterile distilled water was added, followed by spreading the entire amount of the suspension on an agar plate of an SD medium (6.7 g/L of yeast nitrogen base without amino acids (YNB) [manufactured by Becton Dickinson (BD Difco)] and 20 g/L of glucose) (20 g/L of agar powder was added to the medium) and dried, which was then incubated at 30° C. for 3 days to obtain a transformant.

(11) Evaluation of Isobutanol Productivity in Budding Yeast

The colony of the obtained yeast transformant was inoculated onto 5 mL of SD selective medium (SD medium added with 100×amino acid stock solution free of L-leucine) and cultured at 30° C. and at 150 opm for 3 days. After centrifugation was performed at 3,000 rpm for 5 minutes and the medium was disposed of, the microbial body pellet was suspended in 5 mL of sterile distilled water. After further centrifugation as performed at 3,000 rpm for 5 minutes and the supernatant was disposed of, the microbial body pellet was suspended in 5 mL of a new SD selective medium and cultured at 30° C. and at 150 opm for 48 hours. After the culture was centrifuged at 3,000 rpm for 5 minutes, the supernatant was collected. 5100 μL of the collected medium supernatant was added to 45900 μL of acetone, the mixture thereof was mixed by vortexing and centrifuged at 12,000 rpm for 5 minutes, and the supernatant was then collected. The collected supernatant was transferred to a glass vial, and the concentration of isobutanol contained in the medium was quantified by using a DB-FFAP column [manufactured by Agilent Technologies] with a gas chromatography mass spectrometer (GCMS QP2010 Ultra [manufactured by Shimadzu]). As a result, strains showing various isobutanol productions represented by 146 mg/L of clone 96 were obtained as shown in FIG. 5. Among them, strains with higher isobutanol production (29 mg/L and 15 mg/L, respectively) than the production of the yeast strains into which a seed plasmid for overexpression and a seed plasmid for gene expression suppression were introduced were obtained.

Figure 6:
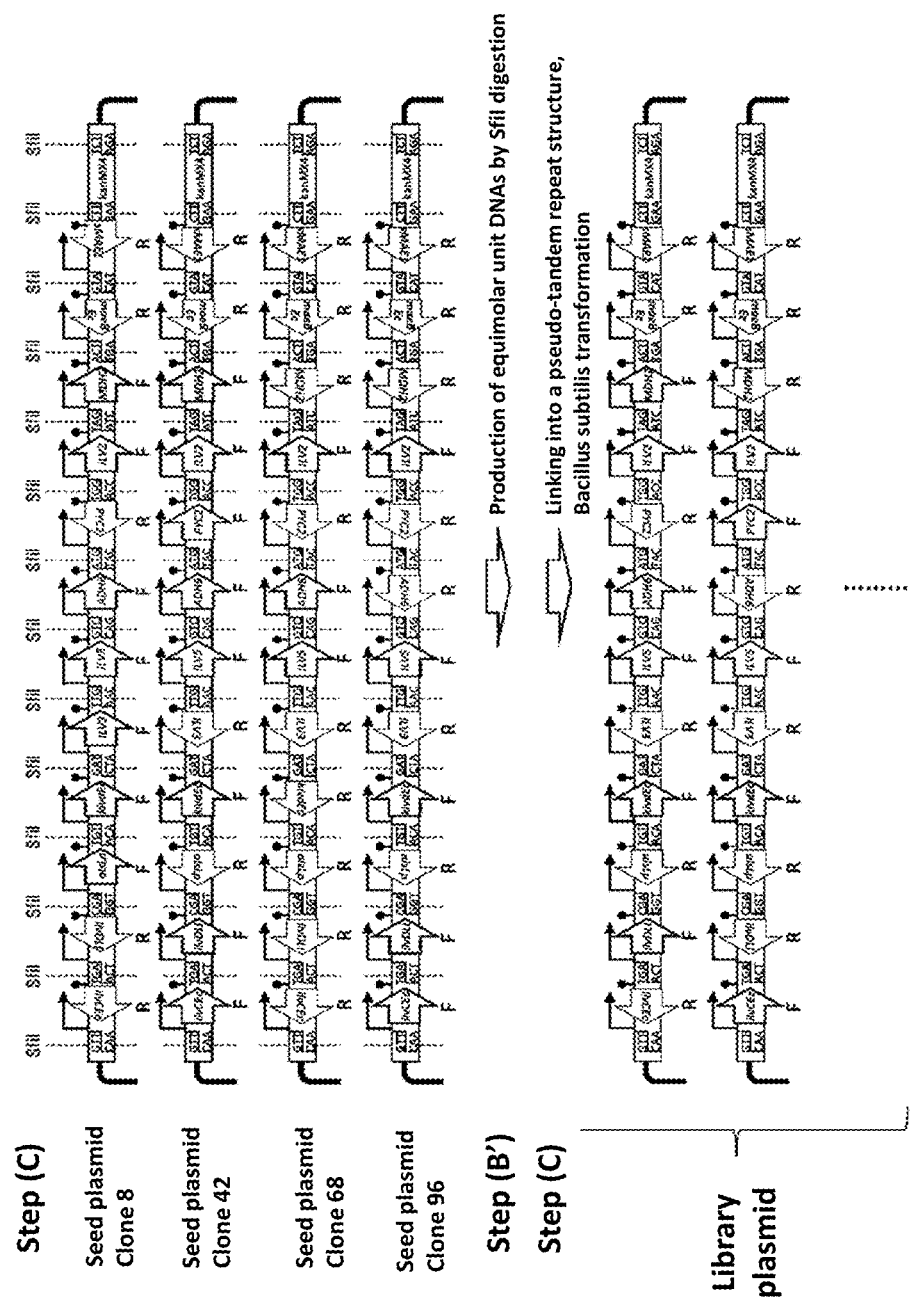
FIG. 6 shows the steps for constructing a new combinatorial library, with the plasmid used for transformation as a seed plasmid.
Figure 7:
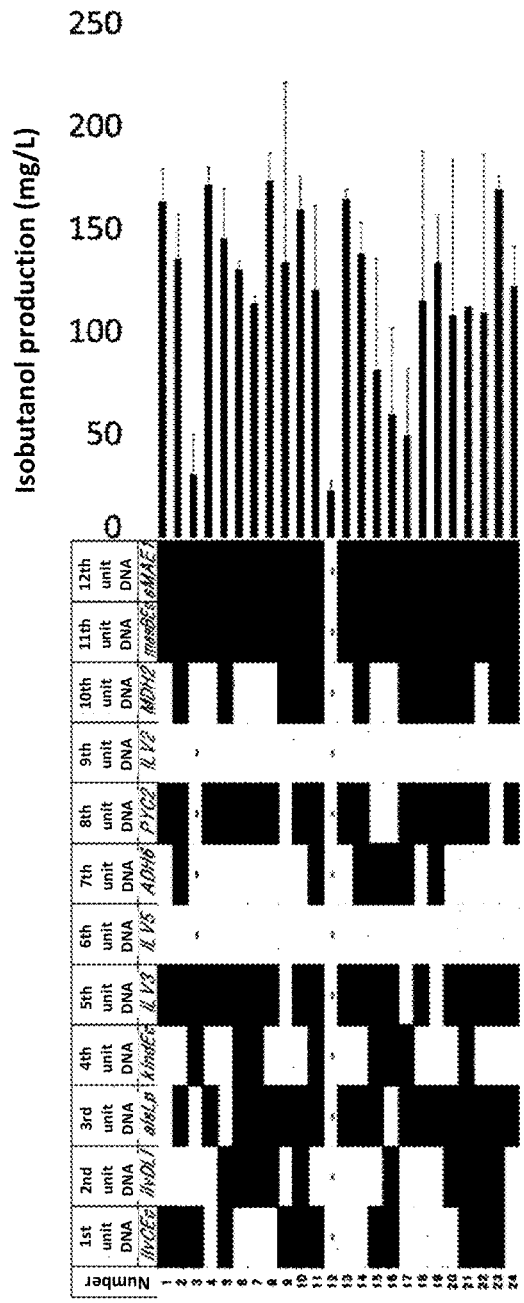
FIG. 7 shows the direction of a unitary gene in each plasmid in the second chimeric plasmid library obtained by the method of the present invention and the isobutanol production.

(12) Selection of an Excellent Plasmid from a Library and Re-Construction of a Library A new combinatorial library was constructed, with a plasmid used in transformation for clone 8, 42, 68, or 96 whose isobutanol production was 120 mg/ml or greater as a seed plasmid (FIG. 6). First, a large quantity of *Bacillus subtilis* having the above-described plasmid was cultured, the plasmid was extracted by the ultracentrifugation method shown in (7), and unit DNAs mixed in an equimolar state were prepared by the method shown in (8). Subsequently, the gene assembling shown in (6) was performed to construct a combinatorial library of the 2nd cycle consisting of about 200 transformants. 24 colonies randomly selected from this library were subjected to extraction of the plasmid from *Bacillus subtilis*, the obtained plasmid was individually introduced to yeast by the method shown in (10), and the isobutanol production was measured by the method shown in (11). The direction of the gene in each unit DNA was separately identified by the method described in (9) for the plasmid extracted from *Bacillus subtilis*. FIG. 7 shows these results. Regarding the library, the 6th, 9th, 11th, and 12th unit DNAs, which are common in the four seed plasmids, were common in 22 clones excluding two clones, i.e., clones 3 and 12 in which assembling was incomplete, and the rest of the unit DNAs generally reflected the composition ratio of the seed plasmids as expected. There were 19 types of different combinations among 22 clones, and 2 types among them were identical to clones 68 and 96 of the first library that were seed plasmids. Clones 8, 4, 23, and 13 had isobutanol production of 173, 171, 169, 164 mg/l, respectively, wherein many clones showing higher productivity than the highest value of 146 mg/L of the first library were obtained.

INDUSTRIAL APPLICABILITY

According to the present invention, it is possible to quickly and efficiently construct a long-chain DNA combinatorial library. In particular, since the present invention is able to reuse a plurality of plasmids selected from the same library for construction of a new chimeric library even without confirming the genotype of the obtained plasmid, the present invention has a feature in that it is possible to quickly construct the second and subsequent libraries.

The invention claimed is:

1. A preparation method of a DNA fragment, the DNA fragment having at least one insert DNA unit comprising: a DNA comprising a replication origin effective in a host; and an insert DNA in which unit DNAs are linked, characterized in that the method comprises:
   (A) processing a plurality of types of plasmids, wherein the plasmids comprise an insert DNA unit in which a plurality of types of unit DNAs capable of being linked in a specific linking order are linked, with a restriction enzyme suitable for each plasmid to prepare a plurality of types of unit DNA mixture solutions each of which comprises the plurality of types of unit DNAs linked on each of the plasmid; and
   (B) re-assembling the plurality of types of unit DNAs by OGAB method using the plurality of types of unit DNA mixture solutions obtained in step (A) to prepare a long-chain DNA fragment.

2. The preparation method of a DNA fragment of claim 1, wherein the DNA fragment is a DNA fragment for cell transformation.

3. The preparation method of a DNA fragment of claim 2, wherein the replication origin is effective in a host microorganism, and the DNA fragment for cell transformation is for microbial cell transformation.

4. The preparation method of a DNA fragment of claim 1, further comprising preparing the plurality of types of plasmids prior to step (A).

5. The preparation method of a DNA fragment of claim 1, wherein the plurality of types of plasmids are prepared by OGAB method.

6. The preparation method of a DNA fragment of claim 1, wherein all the ratios between molar concentrations for DNA fragments in the plurality of types of unit DNA mixture solutions obtained in step (A) are 0.8 to 1.2.

7. The preparation method of a DNA fragment of claim 1, wherein that in the plurality of types of plasmids, the number of types of unit DNAs comprised in one type of insert DNA unit is 3 to 60.

8. The preparation method of a DNA fragment of claim 1, wherein the number of types of the restriction enzymes used in step (A) is three or less.

9. The preparation method of a DNA fragment of claim 1, wherein the restriction enzyme is a restriction enzyme that produces an overhang end.

10. A preparation method of a DNA fragment, the DNA fragment having at least one insert DNA unit comprising: a DNA comprising a replication origin effective in a host; and an insert DNA in which unit DNAs are linked, characterized in that the method comprises:
    (A') preparing a plurality of types of plasmids comprising a DNA fragment for cell transformation by the preparation method of a DNA fragment of claim 1;
    (B') processing the plurality of types of plasmids obtained in step (A') with a restriction enzyme suitable for each plasmid to cleave the plasmids into a plurality of types of unit DNAs and preparing a plurality of types of unit DNA mixture solutions; and
    (C) re-assembling the plurality of types of unit DNAs by OGAB method using the plurality of types of unit DNA mixture solutions obtained in step (B') to prepare a long-chain DNA fragment.

11. The preparation method of a DNA fragment of claim 10, comprising selecting a plurality of types of plasmids comprising the obtained long-chain DNA fragment and reusing the plasmids as the plasmids in step (B').

12. A preparation method of a plasmid, the method comprising:
    preparing a DNA fragment by the preparation method of a DNA fragment of claim 1; and
    including the DNA fragment in a plasmid.

13. A method for constructing a chimeric plasmid library, using the preparation method of a DNA fragment of claim 1.

14. A method for constructing a chimeric plasmid library, using the preparation method of a plasmid of claim 12.

15. A cell transformation method comprising:
    preparing a DNA fragment by the preparation method of a DNA fragment of claim 1; and
    transforming a cell with the DNA fragment or the plasmid.

16. A cell transformation method comprising:
    preparing a plasmid by the preparation method of a plasmid of claim 12; and transforming a cell with the DNA fragment or the plasmid.

17. A preparation method of a composition for cell transformation, the method comprising:
preparing a DNA fragment by the preparation method of a DNA fragment of claim 1; and
preparing a composition for cell transformation using the DNA fragment or the plasmid.

18. A preparation method of a composition for cell transformation, the method comprising:
preparing a plasmid by the preparation method of a plasmid of claim 12; and
preparing a composition for cell transformation using the DNA fragment or the plasmid.

19. A method for transforming a cell with a DNA fragment of interest,
wherein the DNA fragment has at least one insert DNA unit comprising: a DNA comprising a replication origin effective in a host that is the cell; and an insert DNA,
wherein the insert DNA is formed by linking a plurality of types of unit DNAs capable of being linked in a specific linking order,
wherein the method comprises:
(A) processing a plurality of types of plasmids comprising the insert DNA unit with a restriction enzyme suitable for each plasmid to prepare a plurality of types of unit DNA mixture solutions each of which comprises the plurality of types of unit DNAs linked on the insert DNA of each of the plasmid;
(B) re-assembling the plurality of types of unit DNAs by OGAB method using the plurality of types of unit DNA mixture solutions obtained in step (A) to prepare a long-chain DNA fragment; and
(C) transforming the cell with the long-chain DNA fragment.

20. A method for producing a cell comprising a DNA fragment of interest,
wherein the DNA fragment has at least one insert DNA unit comprising: a DNA comprising a replication origin effective in a host that is the cell; and an insert DNA,
wherein the insert DNA is formed by linking a plurality of types of unit DNAs capable of being linked in a specific linking order,
wherein the method comprises:
(A) processing a plurality of types of plasmids comprising the insert DNA unit with a restriction enzyme suitable for each plasmid to prepare a plurality of types of unit DNA mixture solutions each of which comprises the plurality of types of unit DNAs linked on the insert DNA of each of the plasmid;
(B) re-assembling the plurality of types of unit DNAs by OGAB method using the plurality of types of unit DNA mixture solutions obtained in step (A) to prepare a long-chain DNA fragment; and
(C) transforming the cell with the long-chain DNA fragment.

* * * * *

SEQUENCE LISTING

<160> NUMBER OF SEQ ID NOS: 62

<210> SEQ ID NO 1
<211> LENGTH: 15333
<212> TYPE: DNA
<213> ORGANISM: Artificial Sequence
<220> FEATURE:
<223> OTHER INFORMATION: Plasmid vector

<400> SEQUENCE: 1

| | | | | | |
|---|---|---|---|---|---|
| ggccttcttg | gccaccccgg | gccgtcgacg | ctctccctta | tgcgactcct | gcattaggaa | 60 |
| gcagcccagt | agtaggttga | ggccgttgag | caccgccgcc | gcaaggaatg | gtgcatgcaa | 120 |
| ggagatggcg | cccaacagtc | ccccggccac | ggggcctgcc | accatacccc | cgccgaaaca | 180 |
| agcgctcatg | agcccgaagt | ggcgagcccg | atcttcccca | tcggtgatgt | cggcgatata | 240 |
| ggcgccagca | accgcacctg | tggcgccggt | gatgccggcc | acgatgcgtc | cggcgtagag | 300 |
| gatccacagg | acgggtgtgg | tcgccatgat | cgcgtagtcg | atagtggctc | caagtagcga | 360 |
| agcgagcagg | actgggcggc | ggccaaagcg | gtcggacagt | gctccgagaa | cgggtgcgca | 420 |
| tagaaattgc | atcaacgcat | atagcgctag | cagcacgcca | tagtgactgg | cgatgctgtc | 480 |
| ggaatggacg | atatcccgca | agaggcccgg | cagtaccggc | ataaccaagc | ctatgcctac | 540 |
| agcatccagg | tgacggtgc | cgaggatgac | gatgagcgca | ttgttagatt | tcatacacgg | 600 |
| tgcctgactg | cgttagcaat | ttaactgtga | taaactaccg | cattaaagct | tatcgatgat | 660 |
| aagctgtcaa | acatgagaat | tcttgaagac | gaaagggcct | cgtgatacgc | ctatttttat | 720 |
| aggttaatgt | catgataata | atggtttctt | agacgtcagg | tggcactttt | cggggaaatg | 780 |
| tgcgcggaac | ccctatttgt | ttatttttct | aaatacattc | aaatatgtat | ccgctcatga | 840 |
| gacaataacc | ctgataaatg | cttcaataat | attgaaaaag | gaagagtatg | agtattcaac | 900 |
| atttccgtgt | cgcccttatt | ccctttttg | cggcattttg | ccttcctgtt | tttgctcacc | 960 |
| cagaaacgct | ggtgaaagta | aaagatgctg | aagatcagtt | gggtgcacga | gtgggttaca | 1020 |
| tcgaactgga | tctcaacagc | ggtaagatcc | ttgagagttt | tcgccccgaa | gaacgttttc | 1080 |
| caatgatgag | cacttttaaa | gttctgctat | gtggcgcggt | attatcccgt | gttgacgccg | 1140 |
| ggcaagagca | actcggtcgc | cgcatacact | attctcagaa | tgacttggtt | gagtactcac | 1200 |
| cagtcacaga | aaagcatctt | acggatggca | tgacagtaag | agaattatgc | agtgctgcca | 1260 |
| taaccatgag | tgataacact | gcggccaact | tacttctgac | aacgatcgga | ggaccgaagg | 1320 |
| agctaaccgc | ttttttgcac | aacatggggg | atcatgtaac | tcgccttgat | cgttgggaac | 1380 |
| cggagctgaa | tgaagccata | ccaaacgacg | agcgtgacac | cacgatgcct | gcagcaatgg | 1440 |
| caacaacgtt | gcgcaaacta | ttaactggcg | aactacttac | tctagcttcc | cggcaacaat | 1500 |
| taatagactg | gatggaggcg | gataaagttg | caggaccact | tctgcgctcg | gcccttccgg | 1560 |
| ctggctggtt | tattgctgat | aaatctggag | ccggtgagcg | tgggtctcgc | ggtatcattg | 1620 |
| cagcactggg | gccagatggt | aagccctccc | gtatcgtagt | tatctacacg | acggggagtc | 1680 |
| aggcaactat | ggatgaacga | aatagacaga | tcgctgagat | aggtgcctca | ctgattaagc | 1740 |
| attggtaact | gtcagaccaa | gtttactcat | atatacttta | gattgattta | aaacttcatt | 1800 |
| tttaatttaa | aaggatctag | gtgaagatcc | tttttgataa | tctcatgacc | aaaatccctt | 1860 |
| aacgtgagtt | ttcgttccac | tgagcgtcag | accccgtaga | aaagatcaaa | ggatcttctt | 1920 |
| gagatccttt | ttttctgcgc | gtaatctgct | gcttgcaaac | aaaaaaacca | ccgctaccag | 1980 |
| cggtggtttg | tttgccggat | caagagctac | caactctttt | tccgaaggta | actggcttca | 2040 |

```
gcagagcgca gataccaaat actgtccttc tagtgtagcc gtagttaggc caccacttca    2100
agaactctgt agcaccgcct acatacctcg ctctgctaat cctgttacca gtggctgctg    2160
ccagtggcga taagtcgtgt cttacccggt tggactcaag acgatagtta ccggataagg    2220
cgcagcggtc gggctgaacg gggggttcgt gcacacagcc cagcttggag cgaacgacct    2280
acaccgaact gagataccta cagcgtgagc tatgagaaag cgccacgctt cccgaaggga    2340
gaaaggcgga caggtatccg gtaagcggca gggtcggaac aggagagcgc acgagggagc    2400
ttccaggggg aaacgcctgg tatctttata gtcctgtcgg gtttcgccac ctctgacttg    2460
agcgtcgatt tttgtgatgc tcgtcagggg ggcggagcct atggaaaaac gccagcaacg    2520 cggcctttt t acggttcctg gccttttgct ggccttttgc tcacatgttc tttcctgcgt    2580
tatcccctga ttctgtggat aaccgtatta ccgcctttga gtgagctgat accgctcgcc    2640
gcagccgaac gaccgagcgc agcgagtcag tgagcgagga agcggaagag cgcctgatgc    2700
ggtattttct ccttacgcat ctgtgcggta tttcacaccg catatggtgc actctcagta    2760
caatctgctc tgatgccgca tagttaagcc agtatacact ccgctatcgc tacgtgactg    2820
ggtcatggct gcgccccgac acccgccaac cccgctgac g cgccctgac gggcttgtct    2880 gctcccggca tccgcttaca gacaagctgt gaccgtctcc gggagctgca tgtgtcagag    2940
gttttcaccg tcatcaccga aacgcgcgag gcaggatccg tatttcacac cgcatatcga    3000
cggtcgagga gaacttctag tatatccaca tacctaatat tattgcctta ttaaaaatgg    3060
aatcccaaca attacatcaa aatccacatt ctcttcaaaa tcaattgtcc tgtacttcct    3120
tgttcatgtg tgttcaaaaa cgttatattt ataggataat tatactctat ttctcaacaa    3180
gtaattggtt gtttggccga gcggtctaag gcgcctgatt caagaaatat cttgaccgca    3240
gttaactgtg ggaatactca ggtatcgtaa gatgcaagag ttcgaatctc ttagcaacca    3300 ttatttttt t cctcaacata acgagaacac acagggg cgc tatcgcacag aatcaaattc    3360
gatgactgga aattttttgt taatttcaga ggtcgcctga cgcatatacc ttttttcaact    3420 gaaaaattgg gagaaaaagg aaaggtgaga ggccggaacc ggcttttcat atagaataga    3480
gaagcgttca tgactaaatg cttgcatcac aatacttgaa gttgacaata ttatttaagg    3540
acctattgtt ttttccaata ggtggttagc aatcgtctta ctttctaact tttcttacct    3600
tttacatttc agcaatatat atatatattt caaggatata ccattctaat gtctgcccct    3660
atgtctgccc ctaagaagat cgtcgttttg ccaggtgacc acgttggtca agaaatcaca    3720
gccgaagcca ttaaggttct taagctatt t ctgatgttc gttccaatgt caagttcgat    3780
ttcgaaaatc atttaattgg tggtgctgct atcgatgcta caggtgtccc acttccagat    3840
gaggcgctgg aagcctccaa gaaggttgat gccgttttgt taggtgctgt gggtggtcct    3900
aaatggggta ccggtagtgt tagacctgaa caaggtttac taaaaatccg taagaacttt    3960
caattgtacg ccaacttaag accatgtaac tttgcatccg actctctttt agacttatct    4020
ccaatcaagc cacaatttgc taaaggtact gacttcgttg ttgtcagaga attagtggga    4080
ggtatttact ttggtaagag aaaggaagac gatggtgatg gtgtcgcttg ggatagtgaa    4140
caatacaccg ttccagaagt gcaaagaatc acaagaatgg ccgctttcat ggccctacaa    4200
catgagccac cattgcctat ttggtccttg gataaagcta atgttttggc ctcttcaaga    4260
ttatggagaa aaactgtgga ggaaaccatc aagaacgaat tccctacatt gaaggttcaa    4320
catcaattga ttgattctgc cgccatgatc ctagttaaga acccaaccca cctaaatggt    4380
```

```
attataatca ccagcaacat gtttggtgat atcatctccg atgaagcctc cgttatccca    4440
ggttccttgg gtttgttgcc atctgcgtcc ttggcctctt tgccagacaa gaacaccgca    4500
tttggtttgt acgaaccatg ccacggttct gctccagatt tgccaaagaa taaggttgac    4560
cctatcgcca ctatcttgtc tgctgcaatg atgttgaaat tgtcattgaa cttgcctgaa    4620
gaaggtaagg ccattgaaga tgcagttaaa aaggttttgg atgcaggtat cagaactggt    4680
gatttaggtg gttccaacag taccaccgaa gtcggtgatg ctgtcgccga agaagttaag    4740
aaaatccttg cttaaaaaga ttctcttttt ttatgatatt tgtacataaa ctttataaat    4800
gaaattcata atagaaacga cacgaaatta caaaatggaa tatgttcata gggtagacga    4860
aactatatac gcaatctaca tacatttatc aagaaggaga aaaaggagga tagtaaagga    4920
atacaggtaa gcaaattgat actaatggct caacgtgata aggaaaaaga attgcacttt    4980
aacattaata ttgacaagga ggagggcacc acacaaaaag ttaggtgtaa cagaaaatca    5040
tgaaactacg attcctaatt tgatattgga ggattttctc taaaaaaaaa aaaatacaac    5100
aaataaaaaa cactcaatga cctgaccatt tgatggagtt taagtcaata ccttcttgaa    5160
ccatttccca taatggtgaa agttccctca agaattttac tctgtcagaa acggccttac    5220
gacgtagtcg atatggtgca ctctcagtac aatctgctct gatgccgcat agttaagcca    5280
gccccgacac ccgccaacac ccgctgacgc gccctgacgg gcttgtctgc tcccggcatc    5340
cgcttacaga caagctgtga ccgtctccgg gagctgcatg tgtcagaggt ttcaccgtc     5400
atcaccgaaa cgcgcgagac gaaagggcct cgtgatacgc ctattttat aggttaatgt      5460
catgataata atggtttctt aggacggatc gcttgcctgt aacttacacg cgcctcgtat    5520
cttttaatga tggaataatt tgggaattta ctctgtgttt atttatttt atgttttgta      5580
tttggatttt agaagtaaa taagaaggt agagagtta cggaatgaag aaaaaaaat         5640
aaacaaggt ttaaaaaatt tcaacaaaaa gcgtacttta catatatatt tattagacaa      5700
gaaaagcaga ttaaatagat atacattcga ttaacgataa gtaaaatgta aaatcacagg    5760
attttcgtgt gtggtcttct acacagacaa gatgaaacaa ttcggcatta atacctgaga    5820
gcaggaagag caagataaaa ggtagtattt gttggcgatc cccctagagt cttttacatc    5880
ttcggaaaac aaaaactatt ttttctttaa tttctttttt tactttctat ttttaattta    5940
tatatttata ttaaaaaatt taaattataa ttattttat agcacgtgat gaaaaggacc      6000
caggatccta actcacatta attgcgttgc gctcactgcc cgctttccag tcgggaaacc    6060
tgtcgtgcca gctgcattaa tgaatcggcc aacgcgcggg gagaggcggt ttgcgtattg    6120
ggcgccaggg tggttttct tttcaccagt gagacgggca acagctgatt gcccttcacc      6180
gcctggccct gagagagttg cagcaagcgg tccacgctgg tttgccccag caggcgaaaa    6240
tcctgtttga tggtggttaa cggcgggata taacatgagc tgtcttcggt atcgtcgtat    6300
cccactaccg agatatccgc accaacgcgc agcccggact cggtaatggc gcgcattgcg    6360
cccagcgcca tctgatcgtt ggcaaccagc atcgcagtgg gaacgatgcc ctcattcagc    6420
atttgcatgg tttgttgaaa accggacatg gcactccagt cgccttcccg ttccgctatc    6480
ggctgaattt gattgcgagt gagatattta tgccagccag ccagacgcag acgcgccgag    6540
acagaactta atgggcccgc taacagcgcg atttgctggt gacccaatgc gaccagatgc    6600
tccacgccca gtcgcgtacc gtcttcatgg gagaaaataa tactgttgat gggtgtctgg    6660
tcagagacat caagaaataa cgccggaaca ttagtgcagg cagcttccac agcaatggca    6720
tcctggtcat ccagcggata gttaatgatc agcccactga cgcgttgcgc gagaagattg    6780
```

```
tgcaccgccg ttttacaggc ttcgacgccg cttcgttcta ccatcgacac caccacgctg   6840
gcacccagtt gatcggcgcg agatttaatc gccgcgacaa tttgcgacgg cgcgtgcagg   6900
gccagactgg aggtggcaac gccaatcagc aacgactgtt tgcccgccag ttgttgtgcc   6960
acgcggttgg gaatgtaatt cagctccgcc atcgccgctt ccacttttc ccgcgttttc    7020 gcagaaacgt ggctggcctg gttcaccacg cgggaaacgg tctgataaga gacaccggca   7080
tactctgcga catcgtataa cgttactggt ttcatcaaaa tcgtctccct ccgtttgaat   7140
atttgattga tcgtaaccag atgaagcact ctttccacta tccctacagt gttatggctt   7200
gaacaatcac gaaacaataa ttggtacgta cgatctttca gccgactcaa acatcaaatc   7260
ttacaaatgt agtctttgaa agtattacat atgtaagatt taaatgcaac cgttttttcg   7320
gaaggaaatg atgacctcgt ttccaccgaa ttagcttgca tgcaaatcga taaagatccg   7380
cgttctgcgg taatctcatg tgcatattct tccatctcaa taaggatgaa acgacgattc   7440
cctccatctt gtttgttaag cgataatact gcatgagcag tagtgccact ccctgcaaat   7500
gagtcaagta caatcgcttc tttgttttca gtcgcaaatt gtattagtct ttttaccaaa   7560
tcaattgatt tagggttatc gaaaaccttc cttccaaata tcttctttaa ttgactagaa   7620
ccgttgggtt ttaagtcaaa ccaggcatta cttaacaact ttttgctagt cggtggaaca   7680
aagtgctcaa tcgtgccatt atcattttgt cgtaacaagt caatatcttc cccattattt   7740
tctacatatt caagatacca tttatcaata tcctcttgag ttggattagt aatgccttt    7800 tgtctaagtt catctaacat catttgatag ttttcaatag cctggagact acgttctttc   7860
ccccatctcc attgaccttc tgtcggagta accccaaata attcatatct catagtttta   7920
cggtctgtac ctctccaatg attattccaa ctaccaggct tttcttctac atcttcataa   7980
accttattaa atcgtcgaga tggctgttta gtgtaaacca aaatagactc ataaccattt   8040
gaaagagaat caattgtgtc aaattgcgct tgaacatttt ttactcctct acgaatgata   8100
atagcgtcac gaaaattctc ctcaccgaat atttcgttca taaggcacgt aagatggtgt   8160
atttcattgt agtcaatgct tacaaatatc actccgtctt ctgacaacaa ctctttcaac   8220
agttttaacc tcggcatcat catacaaagc cacttatcat gtcgggataa gtcttcttg   8280 tctaccactt ttccaagcca ttccctaatc attggggagt tgacattatc attataaatc   8340 cattttttcag ttccagtatt gtatggtggg tcaatataga tgcaatctat cttaccagca   8400
tatgtaggta gtagagctttt caacgccttt aaattgtccc catgaatgat aagattgtca   8460
tgaagactaa ctttatcggt cagacttttt tctggttctg ggatcaattc atgatatttt   8520
acagtcaagt gatgattttg tacaaaagac ttccccttaa acgaaatagt aggcatgtat   8580
tgaacctcct tatgtagata aaaatcctaa tgtgtttta ttcttagtct ctgctaactc    8640
aaggagagat tatattagag ataaagtgt taaaaatcac gtacacgaac aaggcgtgta    8700
cgacagcccc ctcctttctc ggagtgttct tcctcttccc ccatgttgga agggcttgtg   8760
atgttgacag caccgtccct acccatcagg acttttaacc atcaacgaca gtggctacga   8820
actagaggag catttgtagg tgtcatgacc tttccaacgt agtcctcgaa agacttgggg   8880
tagtcaacta gggcttttta caagccccac ttcaaaagcc gttaggcttt aagtggtggg   8940
tagttgacct tcggtttgtt cttctctttc ctccaaccaa ttatagaacg gtactcttga   9000
tctttgttgc tcctgttgtt gttttttcctg ttccttctgt tttttatatt ggtttagttt   9060
ataagtagca tgttcacttt gggaagaagc tctattcatt acaagaccat ttaccatata   9120
```

-continued

```
taaggctcgg tcacgtattg ggtttaatct acctttttta gattttcat agtctgctat    9180 ttttttatc attttactga tttcgtgcgt gtaaaaagta gaaatccctg ctttccataa    9240
ataacatacc aaccgttctt caaagtgttt atcaaagcta agttttcac gtaactgtat    9300 aactgaaaat ctattaataa attgataggc ctgtttaata tcttcttgtg aaaaaagtaa    9360
tgacctattt attgtacgac cagttggttc attttcgatt tcctcatcat catcaattaa    9420
taaattattt gaaacattag tagaaatatt tgataagtta ttaaagatat ttgataatt     9480 attgggtttt attttgaaa cggtcaccgt ttcattttg aaaccctcca ccgtttcatt      9540
tttgaaaccc tccaccgttt cattttgaa accgttgtgg ataactcttt ttaacttata     9600
tttacgtttc tttttagtta cttcttcggg tttcttttcg ggttcttctt cactatcttt   9660
tttccttggt ctaccacctg ttttacctaa ttctttagaa acggaattat agtctttatc    9720
ccaatctctt aattttctca gtggtttata cttttcttct atttcgtgta aaggatactc    9780
ataaacaatt atatttttag gtttagtaga attacggtta gattcttcgt attctatgat    9840
gtctattaat ccatattccc ataaaggttt tatcaatcta taaaacttac tttttgagat    9900
tcctagtgtc tttttatata tgttctcaaa acttctaggt atgcgatcat aatctcggag    9960
ttcatcttct ctatctaccc aagtatgaa cctcaaccat aaagtaaacg tttcgtgtcc    10020
tagtttatca atccaatcat cagctactac ataagtcatt ataggtaggt ttaattccca   10080
tctgttcttc ttaccacgtt ttactggttc attattcact ttgcattcct ccaatcaatt   10140
tgttattgga gaaatgtacg aaacgtgata caatgtaaat gtatctagtt atttttatt   10200 tatacgttt cgtacatttc tcgaaagagt atccgttgtg agcgggtact cttattttt    10260 tgtcatcacc aaaccaacgc ctaaaacgtt taatttccat attcatatct caattaaaaa   10320
ataacacgat accagcgagt gtggagtcca caaaaagtac acaaaaagtc tacaaaagtc   10380
cataatacct ataaaataac ctcaactctt ccagaaaaac ttttgttgca gaaaggtctt   10440
ttatgacgtt aatttccttt taaatcattg atataacagg gttttaagt tagaacgtcc    10500 gacgtaattt ccaattttct attcaatttt ttcacaacgt cataacttt tgcttgtcga    10560 ttcactgcaa cccttaatac atcaacaatc tattgaagca ataacgtcc gacgttcatc    10620 taccaaaacg tccgacgttg aaatgacaat aacacctatc caattagcaa gcaggctaac    10680
gcccataata taagggcgac gaaccatgag acactaattt ttccagttta tagttgtttc   10740
agcagtctgt ataagtgcga tttatctaca ccaagtattt ttgctaattt aattttttgag 10800 attttgggat tctgttctaa taactcctgc aatttaaata atttatcatc tgttttatcc   10860
tgttgttgct taatatactc ctgtcgggtc atatctcccc gctcacgacg ttttgttct    10920 tgataaatcc tatcccttc ccgctttctt ctccgtttct cattagcgtc tataatcgtc    10980
tgtaaatgct tctgttcttc tggtgtgata tctagccatt caatcaactt tttattgcta   11040
atattgtatc cagcactggg atatcctttt tcgattgcaa tccggttagc ctcttcgtta   11100
tttcgtgctt cccacgcctt ttctgcgctc cgtgtagccc tttcaacctc ttttaagggt   11160
aaaggctcag tgaactgtaa attaagtgtc tgtgtttgat ttaaagcctc tacagggtcg   11220
ttcgtgtaac agcacaacca ataacggtat aaaaagcaaa tgatttccct gtatccagtt   11280
acctcataat ttcgtagttc caccaatttc actatatcca ataggcgagc gtaatggagt   11340
ttgtaggtat tgaataactg aactactttc ttttacgcc ccgtttttt cttttgtgga     11400 gcgggattaa taacctcatt gagttctgga aggtaatcaa attgaatctg ccttaactca   11460
tatctgtaat cgtgccgata ttccgctctt acttccgctc cattcttact attgacgctc   11520
```

```
ccagcaatcc gaaaaacacg tgctgcatcg gttgcttttg gatctccgcc tagttccttg    11580
agttgctcta ataaataatt ttgaacagcc tgccaaagcg gaagagcctt gtaaggcact    11640
ggctcaagca accatatgag aacaaggcct tgtccactaa aaataaggat attgggttca    11700
ggaatgcttt taccatagaa ttagcttaat tgttatccgc tcacaattcc acacattatg    11760
ccacaccttg tagataaagt caacaacttt ttgcaaaatt tttcaggaat tttagcagag    11820
gttgttctgg atgtagaaca aaacatcttt ccgctcttgt gctgttagga tatctttctt    11880
ggaagctagg taggcaaggg ctacctcaaa taaatcttct tcagggtgcg ctattttaa     11940 ggtgcctagt gaggtcttga ccacttcacc cataatttca gtgccgaata gtctggactg    12000
ggctgtgtag aattgtagat atgacgacag gaagagtttg tagaaacgca aaaaggccat    12060
ccgtcaggat ggccttctgc ttaatttgat gcctggcagt ttatggcggg cgtcctgccc    12120
gccaccctcc gggccgttgc ttcgcaacgt tcaaatccgc tcccggcgga tttgtcctac    12180
tcaggagagc gttcaccgac aaacaacaga taaaacgaaa ggcccagtct ttcgactgag    12240
cctttcgttt tatttgatgc ccaattcctg ttataaaaaa aggatcaatt ttgaactctc    12300
tcccaaagtt gatcccttaa cgatttagaa atccctttga gaatgtttat atacattcaa    12360
ggtaaccagc caactaatga caatgattcc tgaaaaagt aataacaaat tactatacag     12420
ataagttgac tgatcaactt ccataggtaa caacctttga tcaagtaagg gtatggataa    12480
taaaccacct acaattgcaa tacctgttcc ctctgataaa aagctggtaa agttaagcaa    12540
actcattcca gcaccagctt cctgctgttt caagctactt gaaacaattg ttgatataac    12600
tgttttggtg aacgaaagcc cacctaaaac aaatacgatt ataattgtca tgaaccatga    12660
tgttgtttct aaaagaaagg aagcagttaa aaagctaaca gaaagaaatg taactccgat    12720
gtttaacacg tataaaggac ctcttctatc aacaagtatc ccaccaatgt agccgaaaat    12780
aatgacactc attgttccag ggaaaataat tacacttccg atttcggcag tacttagctg    12840
gtgaacatct ttcatcatat aaggaaccat agagacaaac cctgctactg ttccaaatat    12900
aattccccca caagaactc caatcataaa aggtatattt ttccctaatc cgggatcaac     12960
aaaaggatct gttactttcc tgatatgttt tacaaatatc aggaatgaca gcacgctaac    13020
gataagaaaa gaaatgctat atgatgttgt aaacaacata aaaaatacaa tgcctacaga    13080
cattagtata attcctttga tatcaaaatg acctttatc cttacttctt tctttaataa     13140
tttcataaga aacggaacag tgataattgt tatcatagga atgagtagaa gataggacca    13200
atgaatataa tgggctatca ttccaccaat cgctggaccg actccttctc ccatggctac    13260
tatcgatcca ataagaccaa atgctttacc cctatttcc tttggaatat agcgcgcaac     13320
tacaaccatt acgagtgctg gaaatgcagc tgcaccagcc ccttgaataa aacgagccat    13380
aataagtaag gaaagaaag aatggccaac aaacccaatt accgacccga aacaatttat     13440
tataattcca ataggagta accttttgat gcctaattga tcagatagct ttccatatac     13500
agctgttcca atggaaaagg ttaacataaa ggctgtgttc acccagtttg tactcgcagg    13560
tggtttatta aaatcatttg caatatcagg taatgagacg ttcaaaacca tttcatttaa    13620
tacgctaaaa aagataaaa tgcaaagcca aattaaaatt tggttgtgtc gtaaattcga     13680
ttgtgaatag gatgtattca catttcaccc tccaataatg agggcagacg tagtttatag    13740
ggttaatgat acgcttccct cttttaattg aaccctgtta cattcattat tcattacact    13800
tcataattaa ttcctcctaa acttgattaa aacattttac cacatataaa ctaagtttta    13860
```

```
aattcagtat tcatcactt atacaacaat atgggggat cttgttgaga aatgttaaat    13920
gttttcatat attcttcttc ctccgatttc tgcaaaaatg aatcattgaa tatttaaata    13980
ttcttaattt tattttacaa aaatagagag aaagatcaag tagaaattca atttcacttc    14040
ataaccgata ttaggaattt catttataac taccaataac gtgaattatg taaataagct    14100
gttcatatcg accgggaagg gcgaattctg cggtaaagct catcagcgtg gtcgtgaagc    14160
gattcacaga tgtctgcctg ttcatccgcg tccagctcgt tgagtttctc cagaagcgtt    14220
aatgtctggc ttctgataaa gcgggccatg ttaagggcgg ttttttcctg tttggtcact    14280
gatgcctccg tgtaagggg atttctgttc atggggtaa tgataccgat gaaacgagag    14340
aggatgctca cgatacgggt tactgatgat gaacatgccc ggttactgga acgttgtgag    14400
ggtaaacaac tggcggtatg gatgcggcgg gaccagagaa aaatcactca gggtcaatgc    14460
cagcgcttcg ttaatacaga tgtaggtgtt ccacagggta gccagcagca tcctgcgatg    14520
cagatccgga acataatggt gcagggcgct gacttccgcg tttccagact ttacgaaaca    14580
cggaaaccga agaccattca tgttgttgct caggtcgcag acgttttgca gcagcagtcg    14640
cttcacgttc gctcgcgtat cggtgattca ttctgctaac cagtaaggca accccgccag    14700
cctagccggg tcctcaacga caggagcacg atcatgcgca cccgtggcca ggacccaacg    14760
ctgcccgaga tgcgccgcgt gcggctgctg gagatggcgg acgcgatgga tatgttctgc    14820
caagggttgg tttgcgcatt cacagttctc cgcaagaatt gattggctcc aattcttgga    14880
gtggtgaatc cgttagcgag gtgccgccgg cttccattca ggtcgaggtg gcccggctcc    14940
atgcaccgcg acgcaacgcg gggaggcaga caaggtatag gcggcgcct acaatccatg    15000 ccaacccgtt ccatgtgctc gccgaggcgg cataaatcgc cgtgacgatc agcggtccaa    15060
tgatcgaagt taggctggta agagccgcga gcgatccttg aagctgtccc tgatggtcgt    15120
catctacctg cctggacagc atggcctgca acgcgggcat cccgatgccg ccggaagcga    15180
gaagaatcat aatggggaag gccatccagc ctcgcgtcgc gaacgccagc aagacgtagc    15240
ccagcgcgtc ggccgcaagc ttgaagagct cttctttcag aacgctcggt tgccgccggg    15300
cgttttttat gagacgtctc ggcctgtttg gcc                                 15333
```

<210> SEQ ID NO 2
<211> LENGTH: 2502
<212> TYPE: DNA
<213> ORGANISM: Artificial Sequence
<220> FEATURE:
<223> OTHER INFORMATION: Expression cassette

<400> SEQUENCE: 2

```
ggcctgtttg gccgggtgta caatatggac ttcctctttt ctggcaacca aacccataca      60
tcgggattcc tataataccct tcgttggtct ccctaacatg taggtggcgg aggggagata     120
tacaatagaa cagataccag acaagacata atgggctaaa caagactaca ccaattacac     180
tgcctcattg atggtggtac ataacgaact aatactgtag ccctagactt gatagccatc     240
atcatatcga agtttcacta ccctttttcc atttgccatc tattgaagta ataataggcg     300
catgcaactt cttttctttt tttttctttt ctctctcccc cgttgttgtc tcaccatatc     360
cgcaatgaca aaaaatgat ggaagacact aaaggaaaaa attaacgaca aagacagcac     420
caacagatgt cgttgttcca gagctgatga ggggtatctc gaagcacacg aaacttttc     480 cttccttcat tcacgcacac tactctctaa tgagcaacgg tatacggcct tccttccagt     540
tacttgaatt tgaaataaaa aaaagtttgc tgtcttgcta tcaagtataa atagacctgc     600
```

```
aattattaat cttttgtttc ctcgtcattg ttctcgttcc ctttcttcct tgtttctttt      660
tctgcacaat atttcaagct ataccaagca tacaatcaac tatctcatat acaatggcta      720
actacttcaa caccttgaat ttgagacaac aattggctca attgggtaaa tgcagattca      780
tgggtagaga tgaatttgct gatggtgctt cttacttgca aggtaaaaag gttgttatcg      840
ttggttgtgg tgcccaaggt ttaaatcaag gtttgaacat gagagactcc ggtttggata      900
tttcttacgc cttgagaaaa gaagccattg ctgaaaaaag agcctcttgg agaaaagcta      960
ctgaaaacgg ttttaaggtc ggtacttacg aagaattgat tccacaagct gatttggtca     1020
ttaacttgac cccagataag caacactctg atgttgttag aactgtccaa ccattgatga     1080
aggatggtgc tgctttgggt tattctcatg gttttaacat cgttgaagtc ggtgaacaaa     1140
tcagaaagga tatcaccgtt gttatggttg ctccaaaatg tccaggtact gaagttagag     1200
aagaatacaa gagaggtttc ggtgttccaa ctttgattgc tgttcatcca gaaaatgatc     1260
caaagggtga aggtatggct attgctaaag cttgggctgc tgctactggt ggtcatagag     1320
ctggtgtttt ggaatcttca tttgttgccg aagttaagtc cgatttgatg ggtgaacaaa     1380
ccattttgtg tggtatgttg caagctggtt cttgttgtg tttcgataag ttggttgaag     1440
aaggtactga tccagcttac gctgaaaagt tgattcaatt tggttgggaa accattaccg     1500
aagctttgaa acaaggtggt attaccttga tgatggacag attgtctaat ccagctaagt     1560
tgagagctta cgcattgtcc gaacaattga agaaattat ggccccttg ttccaaaagc     1620 acatggatga tattatctcc ggtgaattct cttctggtat gatggctgat tgggctaatg     1680
atgataagaa gttgttgact tggagagaag aaactggtaa gactgctttt gaaactgctc     1740
cacaatacga aggtaagatt ggtgaacaag aatacttcga taagggtgtt ttgatgatcg     1800
ctatggttaa ggctggtgtt gaattggcat ttgaaactat ggttgactcc ggtatcattg     1860
aagaatctgc ttactacgaa tccttgcacg aattgccatt gattgctaac actatcgcca     1920
gaaaaagatt atacgaaatg aacgtcgtta tctccgatac tgctgaatac ggtaattact     1980
tgttctctta cgcttgcgtt cctttgttga aacctttat ggctgaattg caaccaggtg     2040
atttgggtaa agctattcct gaaggtgctg ttgataatgg tcaattgaga gatgttaacg     2100
aagccattag atcccatgcc attgaacaag ttggtaagaa attgagaggt tacatgaccg     2160
acatgaagag aatagctgtt gctggttaag cgaatttctt atgatttatg attttttatta     2220 ttaaataagt tataaaaaaa ataagtgtat acaaatttta aagtgactct taggttttaa     2280
aacgaaaatt cttattcttg agtaactctt cctgtaggt caggttgctt tctcaggtat     2340
agcatgaggt cgctcttatt gaccacacct ctaccggcat gccgagcaaa tgcctgcaaa     2400
tcgctcccca tttcacccaa ttgtagatat gctaactcca gcaatgagtt gatgaatctc     2460
ggtgtgtatt ttatgtccct agaggacaag gccttgatgg cc                       2502
```

<210> SEQ ID NO 3
<211> LENGTH: 3039
<212> TYPE: DNA
<213> ORGANISM: Artificial Sequence
<220> FEATURE:
<223> OTHER INFORMATION: Expression cassette

<400> SEQUENCE: 3

```
ggccttgatg gccactggta gagagcgact ttgtatgccc caattgcgaa acccgcgata       60
tccttctcga ttctttagta cccgaccagg acaaggaaaa ggaggtcgaa acgttttga      120
```

```
agaaacaaga ggaactacac ggaagctcta aagatggcaa ccagccagaa actaagaaaa    180
tgaagttgat ggatccaact ggcaccgctg gcttgaacaa caataccagc cttccaactt    240
ctgtaaataa cggcggtacg ccagtgccac cagtaccgtt accttcggt atacctcctt     300 tccccatgtt tccaatgccc ttcatgcctc caacggctac tatcacaaat cctcatcaag    360
ctgacgcaag ccctaagaaa tgaataacaa tactgacagt actaaataat tgcctacttg    420
gcttcacata cgttgcatac gtcgatatag ataataatga taatgacagc aggattatcg    480
taatacgtaa tagttgaaaa tctcaaaaat gtgtgggtca ttacgtaaat aatgatagga    540
atgggattct tctatttttc cttttccat tctagcagcc gtcgggaaaa cgtggcatcc      600
tctctttcgg gctcaattgg agtcacgctg ccgtgagcat cctctctttc catatctaac    660
aactgagcac gtaaccaatg gaaaagcatg agcttagcgt tgctccaaaa aagtattgga    720
tggttaatac catttgtctg ttctcttctg actttgactc ctcaaaaaaa aaaaatctac    780
aatcaacaga tcgcttcaat tacgccctca caaaaacttt tttccttctt cttcgcccac    840
gttaaatttt atccctcatg ttgtctaacg gatttctgca cttgatttat tataaaaaga    900
caaagacata atacttctct atcaatttca gttattgttc ttccttgcgt tattcttctg    960 ttcttcttt tcttttgtca tatataacca taaccaagta atacatattc aaaatggaat      1020
tcaagtacaa cggtaaggtc gaatccgttg aattgaacaa gtactctaag accttgactc    1080
aagatccaac tcaaccagct acacaagcta tgtattacgg tattggttc aaggacgaag      1140 atttcaagaa agcccaagtt ggtatcgttt ctatggattg ggatggtaat ccatgcaata    1200
tgcatttggg tactttgggt tccaagatca agtcctctgt taatcaaact gatggtttga    1260
tcggtttaca attccatacc atcggtgttt ctgatggtat tgctaatggt aaattgggta    1320
tgagatactc cttggtcagt agagaagtta ttgccgattc cattgaaact aatgctggtg    1380
ccgaatatta cgatgctata gttgctattc caggttgcga taagaatatg ccaggttcca    1440
ttattggtat ggccagattg aatagaccat ccattatggt ttacggtggt actattgaac    1500
acggtgaata caaaggtgaa aagttgaaca tcgtttccgc ctttgaatct ttgggtcaaa    1560
agattactgg taacatctcc gatgaagatt accatggtgt tatatgcaat gccattccag    1620
gtcaaggtgc ttgtggtggt atgtatactg ctaatacttt ggctgctgct attgaaacct    1680
tgggtatgtc tttgccatac tcttcatcta atccagccgt ttctcaagaa aagcaagaag    1740
aatgcgacga aattggtttg gccattaaga acttgttgga aaaggatatc aagccatccg    1800
acatcatgac caaagaagct tttgaaaacg ccatcaccat cgttatggtt tgggtggtt     1860 ctacaaatgc cgtcttgcat attattgcaa tggctaacgc tatcggtgtt gaaattactc    1920
aagatgactt ccaaagaatc tccgatatta ctccagtctt gggtgatttt aaaccatccg    1980
gtaagtacat gatggaagac ttgcataaga ttggtggttt gccagctgtt ttgaaatact    2040
tgttgaaaga aggtaaattg cacggtgatt gcttgactgt tacaggtaaa acattggccg    2100
aaaacgttga aactgctttg gatttggatt tcgactccca agatattatg agaccattga    2160
agaatccaat caaggctact ggtcacttgc aaatcttgta tggtaatttg gctcaaggtg    2220
gttccgttgc taaatctct ggtaagaag gtgaattctt caagggtact gctagagttt      2280
ttgatggtga acaacatttc atcgacggta tcgaatctgg tagattgcat gctggtgatg    2340
ttgctgttat tagaaacatt ggtccagttg gtggtccagg tatgccagaa atgttgaaac    2400
ctacttctgc tttgattggt gctggtttgg gtaaatcttg tgccttgatt actgatggta    2460
gattctctgg tggtactcat ggttttgttg ttggtcatat tgtccctgaa gctgttgaag    2520
```

```
gtggtttaat aggtttggtt gaagatgacg acatcatcga aattgatgcc gttaacaact    2580
ccatctcctt gaaggtttca gatgaagaaa ttgctaagag gagagccaac taccaaaaac    2640
ctactccaaa agctacaaga ggtgttttgg ctaagtttgc taaattgact agaccagctt    2700
ctgaaggttg tgttactgat ttgtaagtta attcaaatta attgatatag ttttttaatg    2760
agtattgaat ctgtttagaa ataatggaat attattttta tttatttatt tatattattg    2820
gtcggctctt ttcttctgaa ggtcaatgac aaaatgatat gaaggaaata atgatttcta    2880 aaatttttaca acgtaagata tttttacaaa agcctagctc atctttttgtc atgcactatt    2940 ttactcacgc ttgaaattaa cggccagtcc actgcggagt catttcaaag tcatcctaat    3000
cgatctatcg ttttttgatag ctcattggcc tcgatggcc                          3039
```

<210> SEQ ID NO 4
<211> LENGTH: 2399
<212> TYPE: DNA
<213> ORGANISM: Artificial Sequence
<220> FEATURE:
<223> OTHER INFORMATION: Expression cassette

<400> SEQUENCE: 4

```
ggcctcgatg gcctcgtagg aacaatttcg ggcccctgcg tgttcttctg aggttcatct      60
tttacatttg cttctgctgg ataattttca gaggcaacaa ggaaaaatta gatggcaaaa     120
agtcgtcttt caaggaaaaa tccccaccat ctttcgagat cccctgtaac ttattggcaa     180
ctgaaagaat gaaaaggagg aaaatacaaa atatactaga actgaaaaaa aaaaagtata     240
aatagagacg atatatgcca atacttcaca atgttcgaat ctattcttca tttgcagcta     300
ttgtaaaata taaaacatc aagaacaaac aagctcaact tgtcttttct aagaacaaag     360
aataaacaca aaaacaaaaa gttttttttaa ttttaatcaa aaaatgccag acaaaaagta     420
ttatggtgcc gatgctatcg ttgactcctt ggttaatcat gatgtcaagt acgtttttcgg    480 tattccaggt gctaagatcg atagagtttt cgaaagattg gaacacccag ttaatccaaa     540
gtctccaaga ttgatcgtta ccagacatga acaaaacgct gcttttattg ctgctggtat     600
tggtagaatt actggtaaac caggtgttgt tatgactact tctggtccag gtgcatctaa     660
tttggctact ggtttggtta ctgctactgc tgaaggtgat ccagttttgg ctatttctgg     720
tcaagttcaa agagccgatt tgttgagatt gacccatcaa tctatgaaca atgctgcttt     780
gttcaagcca atcactaagt actctgctga agttcaagaa ccagaaaaca tctctgaagt     840
tttggccaat gcttaccaag aagctacagc tgctaaacaa ggtgcttctt ttgtttctgt     900
tccacaagat gttaccgact ctatagttag aactccagtt attaccccaa ttcaagctcc     960
aaaattgggt ccagcttctc cagttgaagc tactttgtta gctcaaaaga ttaaggctgc    1020
taagttgcca gttttgttgg ttggtatgag agcttcttca ccagaagtta ctaaggctat    1080
cagaaatttg gttgctgcag ctaatttgcc tgttgttgaa acttttcaag ctgccggtgt    1140
tattcccaga gatttggaag ctaatcactt cttcggtaga gttggtttgt tcagaaatca    1200
accaggtgac atgttattga agaagtccga tttggttatt gccgttggtt acgatccaat    1260
tgaatacgaa cctagaaatt ggacgccgaa ggtaaatct agaatcgttg ttattgatgc    1320
catgagagcc gaaatcgatc ataatttcca accagaaacc gaattgatcg gtgatattgc    1380
tcaaaccttg gatttcttgt tgccttacat gaagggttac gatatttccg attctgctag    1440
agcttatttg ggtgaattgc aagaaagatt gcaaaccaga gacttcgttc caaacatcga    1500
```

|          |          |          |          |          |      |
|----------|----------|----------|----------|----------|------|
| taagcaatcc | aagttgaacc | atccattgtc | tgttattgca | gccttgcaac | aaagagtttc | 1560 |
| tgatgatatg | actgttaccg | ttgatgttgg | ttcccattac | atttggatgg | ctagacattt | 1620 |
| cagatcctat | gaacctagac | acttgttgtt | ctctaacggt | atgcaaactt | tgggtgttgc | 1680 |
| tttaccatgg | gctattgcag | ctgctttggt | tagaccagat | actcaaatag | tttccgtttc | 1740 |
| tggtgatggt | ggtttttttgt | tttctgccca | agaattggaa | accgccgtta | gattgaaaca | 1800 |
| aaacatcgtt | catttgatct | ggaacgacgg | tacttacgat | atggttaagt | tccaagaaga | 1860 |
| aatgaagtac | ggtgaagatg | ctgctgttca | ttttggtcca | gttgattttg | ttaagtacgc | 1920 |
| cgaatctttt | ggtgctacag | gtttgagagt | taatcaacct | gctgatttgg | aaaaggtttt | 1980 |
| ggatcaagct | tttgctactg | atggtccagt | cgttgttgat | attccaatcg | attactctga | 2040 |
| caacaaggct | ttgggtaaaa | ctatgttgcc | agaccaattc | tactaatttg | cgaacacttt | 2100 |
| tattaattca | tgatcacgct | ctaatttgtg | catttgaaat | gtactctaat | tctaattta  | 2160 |
| tatttttaat | gatatcttga | aaagtaaata | cgttttttaat | atatacaaaa | taatacagtt | 2220 |
| taattttcaa | gttttttgatc | atttgttctc | agaaagttga | gtgggacgga | gacaaagaaa | 2280 |
| ctttaaagag | aaatgcaaag | tgggaagaag | tcagttgttt | accgaccgca | ctgttattca | 2340 |
| caaatattcc | aattttgcct | gcagacccac | gtctacaaat | tttggtggcc | ttgttggcc  | 2399 |

<210> SEQ ID NO 5
<211> LENGTH: 2623
<212> TYPE: DNA
<213> ORGANISM: Artificial Sequence
<220> FEATURE:
<223> OTHER INFORMATION: Expression cassette

<400> SEQUENCE: 5

|          |          |          |          |          |      |
|----------|----------|----------|----------|----------|------|
| ggccttgttg | gccttgagat | aagcacactg | cacccatacc | ttccttaaaa | acgtagcttc | 60 |
| cagtttttgg | tggttccggc | ttccttcccg | attccgcccg | ctaaacgcat | attttttgttg | 120 |
| cctggtggca | tttgcaaaat | gcataaccta | tgcatttaaa | agattatgta | tcctcttctg | 180 |
| acttttcgtg | tgatgaggct | cgtggaaaaa | atgaataatt | tatgaatttg | agaacaattt | 240 |
| tgtgttgtta | cggtatttta | ctatggaata | atcaatcaat | tgaggatttt | atgcaaatat | 300 |
| cgtttgaata | ttttttccgac | cctttgagta | cttttcttca | taattgcata | atattgtccg | 360 |
| ctgcccctttt | ttctgttaga | cggtgtcttg | atctacttgc | tatcgttcaa | caccaccttta | 420 |
| ttttctaact | attttttttttt | tagctcattt | gaatcagctt | atggtgatgg | cacattttttg | 480 |
| cataaaccta | gctgtcctcg | ttgaacatag | gaaaaaaaaa | tatataaaca | aggctctttc | 540 |
| actctccttg | caatcagatt | tgggtttgtt | ccctttatttt | tcatatttct | tgtcatattc | 600 |
| ctttctcaat | tattatttttc | tactcataac | ctcacgcaaa | ataacacagt | caaatcaatc | 660 |
| aaaatgtaca | ccgttggtga | ttacttgttg | gatagattgc | atgaattggg | tatcgaagaa | 720 |
| atctttggtg | ttccaggtga | ttacaacttg | caattcttgg | accaaatcat | ctcccacaaa | 780 |
| gatatgaagt | gggttggtaa | tgctaacgaa | ttgaacgctt | cttatatggc | tgatggttac | 840 |
| gctagaacaa | aaaaggctgc | tgcttttttttg | actactttcg | gtgttggtga | attgtctgct | 900 |
| gttaatggtt | tggctggttc | ttacgctgaa | aatttgccag | ttgttgaaat | cgttggttct | 960 |
| ccaacttcta | aggttcaaaa | cgaaggtaaa | ttcgttcatc | atactttggc | cgatggtgat | 1020 |
| tttaagcact | ttatgaagat | gcacgaacca | gttactgctg | ctagaacttt | gttgactgct | 1080 |
| gaaaatgcta | ccgtcgaaat | cgatagagtt | ttgtccgctt | tgttgaaaga | aagaagcca  | 1140 |
| gtctacatca | acttgcctgt | tgatgttgct | gctgctaaag | ctgaaaaacc | atctttgcca | 1200 |

```
ttgaagaaag aaaactccac ttccaacacc tccgaccaag aaattttgaa caagatccaa    1260
gaatccttga agaacgctaa gaagccaatc gttattactg gtcacgaaat catcagtttc    1320
ggtttggaaa agaccgtcac tcaattcatt tctaagacca agttgccaat caccactttg    1380
aacttcggta agtcatctgt tgatgaagct ttgccatctt tcttgggtat ctacaatggt    1440
actttgtccg aacctaactt gaaagaattc gttgaatccg ccgatttcat cttgatgttg    1500
ggtgttaagt tgaccgattc ttctactggt gctttcactc atcatttgaa cgaaaacaag    1560
atgatctcct tgaacatcga tgaaggtaag atcttcaacg aaagaatcca aaacttcgac    1620
ttcgaatctt tgatctcctc tttgttggac ttgtccgaaa ttgaatacaa gggtaaatac    1680
atcgacaaga agcaagaaga tttcgttcca tccaatgcct tgttgtctca agatagattg    1740
tggcaagctt tgaaaaactt gacccaatct aacgaaacta cgttgctga caaggtact     1800 tcttttttcg gtgcctcttc catttcttg aagtccaagt ctcatttcat tggtcaacca    1860
ttgtggggtt ctattggtta acttttcca gctgctttgg gttctcaaat tgctgacaaa    1920
gaatctagac acttgttgtt cattggtgac ggttcattgc aattgaccgt tcaagaattg    1980
ggtttggcca ttagagaaaa gattaaccca atctgcttca tcatcaacaa cgatggttac    2040
actgtcgaaa gagaaattca cggtccaaat caatcctaca cgatattcc aatgtggaac    2100 tactctaagt tgccagaatc ttttggtgct accgaagata gagttgtttc caagatagtt    2160
agaaccgaaa acgaatttgt ctccgttatg aaggaagctc aagctgatcc aaatagaatg    2220
tactggatcg aattgatctt ggctaaagaa ggtgctccaa aggttttgaa gaagatgggt    2280
aaattgttcg cagaacaaaa caagtcttaa gcgatttaat ctctaattat tagttaaagt    2340
tttataagca tttttatgta acgaaaaata aattggttca tattattact gcactgtcac    2400
ttaccatgga aagaccagac aagaagttgc cgacagtctg ttgaattggc ctggttaggc    2460
ttaagtctgg gtccgcttct ttacaaattt ggagaatttc tcttaaacga tatgtatatt    2520
cttttcgttg gaaaagatgt cttccaaaaa aaaaaccgat gaattagtgg aaccaaggaa    2580
aaaaaaagag gtatccttga ttaaggaaca ggcctgattg gcc                      2623
```

<210> SEQ ID NO 6
<211> LENGTH: 2729
<212> TYPE: DNA
<213> ORGANISM: Artificial Sequence
<220> FEATURE:
<223> OTHER INFORMATION: Expression cassette

<400> SEQUENCE: 6

```
ggcctgattg gccaaagatg ccgatttggg cgcgaatcct ttattttggc ttcaccctca      60
tactattatc agggccagaa aaaggaagtg tttccctcct tcttgaattg atgttaccct     120
cataaagcac gtggcctctt atcgagaaag aaattaccgt cgctcgtgat tgtttgcaa     180 aaagaacaaa actgaaaaaa cccagacacg ctcgacttcc tgtcttccta ttgattgcag     240
cttccaattt cgtcacacaa caaggtccta gcgacggctc acaggttttg taacaagcaa     300
tcgaaggttc tggaatggcg ggaaagggtt tagtaccaca tgctatgatg cccactgtga     360
tctccagagc aaagttcgtt cgatcgtact gttactctct ctctttcaaa cagaattgtc     420
cgaatcgtgt gacaacaaca gcctgttctc acacactctt ttcttctaac caaggggtg     480 gtttagttta gtagaacctc gtgaaactta catttacata tatataaact tgcataaatt     540
ggtcaatgca agaaatacat atttggtctt ttctaattcg tagtttttca agttcttaga     600
```

```
tgctttcttt ttctcttttt tacagatcat caaggaagta attatctact ttttacaaca    660
aatataaaac atgggtttgt tgactaaggt tgctacctct agacaattct ctactactag    720
atgtgttgcc aagaagttga acaagtactc ctacattatt accgaaccta aaggtcaagg    780
tgcttctcaa gctatgttgt atgctactgg tttcaagaaa gaagatttca aaaagccaca    840
agtcggtgtt ggttcttgtt ggtggtctgg taatccatgt aatatgcact tgttggactt    900
gaacaacaga tgctcccaat ctattgaaaa ggctggtttg aaagccatgc aattcaacac    960
tattggtgtt tccgatggta tctctatggg tacaaaaggt atgagatact ccttgcaatc   1020
cagagaaatt atcgccgatt ctttcgaaac cattatgatg ctcaacatt  acgatgccaa   1080 cattgctatt ccatcttgcg ataagaatat gccaggtgta atgatggcta tgggtagaca   1140
taatagacca tccattatgg tttacggtgg tactattttg ccaggtcatc caacttgtgg   1200
ttcctctaag atttccaaga acatcgatat cgtttccgcc tttcaatctt acggtgaata   1260
tatctctaag caattcaccg aagaagaaag agaagacgtt gttgaacatg cttgtccagg   1320
tccaggttca tgtggtggta tgtatactgc taataccatg gcttctgctg ctgaagtttt   1380
gggtttgact attccaaact cttcatcttt cccagccgtc agtaaagaaa aattggctga   1440
atgtgataac attggtgaat atatcaaaaa gaccatggaa ttgggtatct tgccaagaga   1500
tatcttgacc aaagaagctt tcgaaaacgc tatcacttac gttgttgcta caggtggttc   1560
taccaatgct gttttacatt tggttgctgt tgctcattct gctggtgtta agttgtctcc   1620
agatgatttc caaagaatct ctgataccac tccattgatc ggtgatttta accatctgg    1680 taagtacgtt atggccgatt tgattaacgt tggtggtact caatccgtca ttaagtactt   1740
gtacgaaaac aatatgttgc acggtaacac tatgactgtt actggtgata ctttggctga   1800
aagagctaaa aaagctccat ctttgccaga aggtcaagaa atcattaagc cattgtctca   1860
tccaatcaag gctaatggtc acttgcaaat cttgtatggt tctttggctc aggtggtgc    1920 tgttggtaaa attactggta agaaggtac ttacttcaag ggtagagcta gagtctttga    1980
agaagaaggt gctttcattg aagctttgga aagaggtgaa atcaagaagg gtgaaaagac   2040
cgttgttgtc attagatatg aaggtccaag aggtgctcca ggtatgccag aaatgttgaa   2100
accatcttct gctttgatgg gttacggttt gggtaaagat gttgctttgt taaccgatgg   2160
tagattctct ggtggttctc atggtttctt gattggtcat attgtccctg aagctgcaga   2220
aggtggtcca attggtttgg ttagagatgg tgacgaaatt atcattgatg ccgacaacaa   2280
caagattgat tgttggtca gtgacaaaga aatggcccaa agaaaacaat cttgggttgc    2340
tccaccacca agatatacaa gaggtacttt gtctaagtac gccaagttgg tttctaatgc   2400
ttctaacggt tgtgttttgg atgcctaaga aataaattga attgaattga atcgataga    2460 tcaattttt tcttttctct ttccccatcc tttacgctaa aataatagtt tattttattt    2520
tttgaatatt ttttatttat atacgtatat atagactatt atttatcttt taatgattat   2580
taagattttt attaaaaaaa aattcgctcc tcttttaatg cctttatgca gttttttttt   2640
cccattcgat atttctatgt tcgggttcag cgtatttaa gtttaataac tcgaaaattc    2700
tgcgttcgtt aaagctggcc tttgtggcc                                     2729
```

<210> SEQ ID NO 7
<211> LENGTH: 2514
<212> TYPE: DNA
<213> ORGANISM: Artificial Sequence
<220> FEATURE:
<223> OTHER INFORMATION: Expression cassette

<400> SEQUENCE: 7

```
ggcctttgtg gccaggattt taatctgttg gagttaaggt gaatacgttt ttccatattg      60
gggtatgcag ctcgaaccta aagtggtatg tacacatccc ctcaagcaca cccattaccc     120
ttataggatt aatgtaagca acagcttaca cggaattgga aatactattc aacgatccat     180
gcatctgcca gattcggaca tgcatattcc ccaattggat atagaaaatt aacgtaaggc     240
agtatctttt cacaatgtac ttgcaacgcg gcgacttaaa gttgaagtac aacctgcagc     300
agcggctttt tgtacggtac gccaaactgt caatggataa tattgcgtag accgaaaaag     360
gtaatcctca acactacccg tggtggatga cctaaagcag taatattggt tggaattatc     420
tcccagacgg caccgtctcc ccgagaaagc ttagccccga ggtctacctt ccatacacca     480
ctgattgctc cacgtcatgc ggccttcttt cgaggacaaa aaggcatata tcgctaaaat     540
tagccatcag aaccgttatt gttattatat tttcattacg aaagaggaga gggcccagcg     600
cgccagagca cacacggtca ttgattactt tatttggcta aagatccatc ccttctcgat     660
gtcatctctt tccattcttg tgtatttttg attgaaaatg attttttgtc cactaatttc     720
taaaaataag acaaaaagcc tttaagcagt ttttcatcca ttttactacg gtaaaatgaa     780
ttagtacggt atggctccca gtcgcattat ttttagattg gccgtagggg ctggggtaga     840
actagagtaa ggaacattgc tctgccctct tttgaactgt catataaata cctgacctat     900
tttattctcc attatcgtat tatctcacct ctcttttttct attctcttgt aattattgat     960
ttatagtcgt aactacaaag acaagcaaaa taaaatacgt tcgctctatt aagatgttga    1020
gaactcaagc tgctagattg atctgcaatt ccagagttat tactgccaag agaactttcg    1080
ctttggctac tagagctgct gcttattcta gaccagctgc aagatttgtt aagccaatga    1140
ttactaccag aggtttgaag caaatcaact tcggtggtac tgttgaaacc gtttacgaaa    1200
gagctgattg gcctagagaa aagttgttgg attacttcaa gaacgatacc ttcgccttga    1260
ttggttatgg ttctcaaggt tatggtcaag gtttgaattt gagagacaac ggtttgaacg    1320
ttatcatcgg tgttagaaaa gatggtgctt cttggaaagc tgctattgaa gatggttggg    1380
ttccaggtaa gaatttgttc actgttgaag atgccatcaa gagaggttct tacgttatga    1440
acttgttgtc tgatgctgct caatctgaaa cttggccagc tattaagcca ttattgacta    1500
agggtaagac cttgtacttc tcccatggtt tttcaccagt tttcaaggat ttgacccatg    1560
ttgaaccacc aaaggatttg gatgttattt tggttgctcc aaagggttct ggtagaactg    1620
ttagatcttt gttcaaagaa ggtagaggta tcaactcctc ttacgctgtt tggaatgatg    1680
ttactggtaa agctcacgaa aaagctcaag cttggctgt tgctattggt tctggttatg    1740
tttaccaaac caccttcgaa agagaagtca attctgactt gtatggtgaa agaggttgtt    1800
tgatgggtgg tattcatggt atgttttttgg cccaatacga tgtcttgaga gaaaatggtc    1860
attctccatc tgaagctttc aacgaaacag ttgaagaagc cacccaatca ttatacccat    1920
tgattggtaa atacggtatg gactacatgt acgatgcttg ttctactact gctagaagag    1980
gtgctttgga ttggtatcca atttttcaaga atgccttgaa gccagttttc caagacttgt    2040
acgaatctac taagaacggt actgaaacta agagatcctt ggaattcaac tcccaaccag    2100
attacagaga aaaattggaa aaagaattgg acaccatcag aaacatggaa atctggaagg    2160
ttggtaaaga agtcagaaag ttaagaccag aaaatcaata aacggtggtg tttgacacat    2220
ccgccttctt aatgctttct ttcagtatta tgttattttt ttgttattcg tttttcactt    2280
```

-continued

| | | |
|---|---|---|
| ctaggctttt tgacagacta gccccgttat accaccatct tgtgggaaa gcccctaaat | 2340 | |
| tgccctgagc agtatcgttt catgtctagt ctctttaaag atgtttctta cgcgttgcgt | 2400 | |
| gtaaaacatc ctctcattca agacagggtt ttctaaaagc aatagggggta gtttaataat | 2460 | |
| tcttatataa tcatcatata cactattttt agttcttaat tggcctgtct ggcc | 2514 | |

<210> SEQ ID NO 8
<211> LENGTH: 2409
<212> TYPE: DNA
<213> ORGANISM: Artificial Sequence
<220> FEATURE:
<223> OTHER INFORMATION: Expression cassette

<400> SEQUENCE: 8

| | | |
|---|---|---|
| ggcctgtctg gcccttccct tttacagtgc ttcggaaaag cacagcgttg tccaagggaa | 60 | |
| caatttttct tcaagttaat gcataagaaa tatctttttt tatgtttagc taagtaaaag | 120 | |
| cagcttggag taaaaaaaaa aatgagtaaa tttctcgatg gattagtttc tcacaggtaa | 180 | |
| cataacaaaa accaagaaaa gcccgcttct gaaaactaca gttgacttgt atgctaaagg | 240 | |
| gccagactaa tgggaggaga aaaagaaacg aatgtatatg ctcatttaca ctctatatca | 300 | |
| ccatatggag gataagttgg gctgagcttc tgatccaatt tattctatcc attagttgct | 360 | |
| gatatgtccc accagccaac acttgatagt atctactcgc cattcacttc agcagcgcc | 420 | |
| agtagggttg ttgagcttag taaaaatgtg cgcaccacaa gcctacatga ctccacgtca | 480 | |
| catgaaacca caccgtgggg ccttgttgcg ctaggaatag gatatgcgac gaagacgctt | 540 | |
| ctgcttagta accacaccac attttcaggg ggtcgatctg cttgcttcct ttactgtcac | 600 | |
| gagcggccca taatcgcgct tttttttttaa aaggcgcgag acagcaaaca ggaagctcgg | 660 | |
| gtttcaacct tcggagtggt cgcagatctg gagactggat cttttacaata cagtaaggca | 720 | |
| agccaccatc tgcttcttag gtgcatgcga cggtatccac gtgcagaaca acatagtctg | 780 | |
| aagaaggggg ggaggagcat gttcattctc tgtagcagta agagcttggt gataatgacc | 840 | |
| aaaactggag tctcgaaatc atataaatag acaatatatt ttcacacaat gagatttgta | 900 | |
| gtacagttct attctctctc ttgcataaat aagaaattca tcaagaactt ggtttgatat | 960 | |
| ttcaccaaca cacacaaaaa acagtacttc actaaaattta cacacaaaac aaaatgtcct | 1020 | |
| acccagaaaa gttcgaaggt attgccattc aatcacacga agattggaag aacccaaaaa | 1080 | |
| agactaagta cgatccaaag ccattctacg atcatgatat cgacattaag attgaagctt | 1140 | |
| gtggtgtttg cggttccgat attcattgtg ctgctggtca ttggggtaat atgaagatgc | 1200 | |
| cattggttgt tggtcacgaa atcgttggta agttgttaa gttgggtcca aagtctaact | 1260 | |
| ccggtttgaa agttggtcaa agagttggtg ttggtgctca agttttttct tgtttggaat | 1320 | |
| gcgatagatg caagaacgat aacgaaccat actgtactaa gttcgttacc acttactctc | 1380 | |
| aaccatacga agatggttat gtttctcaag gtggttacgc taactacgtt agagttcacg | 1440 | |
| aacatttcgt tgttccaatc ccagaaaaca tcccatctca tttggctgct ccattattgt | 1500 | |
| gtggtggttt gactgtttat tcccccattgg ttagaaatgg ttgtggtcca ggtaaaaagg | 1560 | |
| ttggtatagt tggtttgggt ggtattggtt ctatgggtac tttgatttct aaagctatgg | 1620 | |
| gtgctgaaac ctacgtcatt tctagatcct ctagaaaaag agaagatgca atgaagatgg | 1680 | |
| gtgccgatca ttatattgct actttggaag aaggtgactg gggtgaaaag tacttcgata | 1740 | |
| cttttgattt gatcgttgtc tgcgcttctt ccttgactga tattgatttc aacattatgc | 1800 | |
| caaaggccat gaaggttggt ggtagaatag tttccatttc cattccagaa caacacgaaa | 1860 | |

```
tgttgtcctt gaaaccatac ggtttgaagg ccgtttctat ttcttattct gctttgggtt    1920
ccatcaaaga attgaatcaa ttattgaagt tggtttccga aaaggacatc aagatttggg    1980
ttgaaacttt gccagttggt gaagctggtg ttcatgaagc ttttgaaaga atggaaaagg    2040
gtgacgtcag atacagattc actttggttg gttacgacaa agaattctcc gactaaataa    2100
agcaatcttg atgaggataa tgatttttt ttgaatatac ataaatacta ccgttttct    2160 gctagatttt gtgaagacgt aaataagtac atattacttt ttaagccaag acaagattaa    2220
gcattaactt taccctttc tcttctaagt ttcaatacta gttatcactg tttaaaagtt    2280
atggcgagaa cgtcggcggt taaaatatat taccctgaac gtggtgaatt gaagttctag    2340
gatggtttaa agattttcc ttttttgggaa ataagtaaac aatatattgc tgccttggcc    2400
tatgtggcc                                                            2409

<210> SEQ ID NO 9
<211> LENGTH: 4469
<212> TYPE: DNA
<213> ORGANISM: Artificial Sequence
<220> FEATURE:
<223> OTHER INFORMATION: Expression cassette

<400> SEQUENCE: 9
ggcctatgtg gcctccctgc gcggctaaag ttaaggatgc aaaaaacata agacaactga      60
agttaattta cgtcaattaa gttttccagg gtaatgatgt tttgggcttc cactaattca    120
ataagtatgt catgaaatac gttgtgaaga ggatccagaa ataatgaaaa gaaacaacga    180
aactgggtcg gcctgttgtt tctttcttt accacgtgat ctgcggcatt tacaggaagt    240
cgcgcgtttt gcgcagttgt tgcaacgcag ctacggctaa caaagcctag tggaactcga    300
ctgatgtgtt agggcctaaa actggtggtg acagctgaag tgaactattc aatccaatca    360
tgtcatggct gtcacaaaga ccttgcggac cgcacgtacg aacacatacg tatgctaata    420
tgtgttttga tagtacccag tgatcgcaga cctgcaattt ttttgtaggt ttggaagaat    480
atataaaggt tgcactcatt caagatagtt ttttcttgt gtgtctattc attttattat    540
tgtttgttta aatgttaaaa aaaccaagaa cttagtttca aattaaattc atcacacaaa    600
caaacaaaac aaaatgtcct cctccaaaaa attggctggt ttgagagata acttctcctt    660
gttgggtgaa aagaacaaga ttttggttgc aacagaggt gaaatcccaa tcagaatttt    720
tagatccgcc cacgaattgt ccatgagaac tattgctatc tactcccacg aagatagatt    780
gtctatgcac agattgaaag ctgatgaagc ctacgttatt ggtgaagaag gtcaatatac    840
tccagttggt gcttatttgg ctatggacga attattgaa atcgccaaga agcacaaggt    900
tgatttcatt catccaggtt acggtttctt gtccgaaaac tctgaatttg ctgataaggt    960
tgttaaggct ggtattactt ggattggtcc accagctgaa gttattgatt ctgttggtga   1020
caaagtttcc gctagacatt tggctgctag agctaatgtt ccaactgttc aggtactcc   1080 aggtccaatt gaaactgttc aagaagcttt ggatttcgtc aacgaatatg gttacccagt   1140
tattatcaag gctgctttcg gtggtggtgg tagaggtatg agagttgtta gagaaggtga   1200
tgatgttgct gatgctttc aaagagctac ttctgaagct agaactgctt ttggtaatgg   1260
tacttgcttc gtcgaaagat tcttggataa gccaaagcac atcgaagttc aattattggc   1320
tgataaccac ggtaacgttg ttcacttgtt tgaaagagat tgctccgttc aagaagaca   1380 ccaaaaggtt gttgaagttg ctccagctaa aactttgcca agaagagtta gagatgccat   1440
```

```
tttgactgat gctgttaagt tggctaaagt ctgtggttat agaaatgctg gtactgccga    1500
attcttggtc gataatcaaa acagacacta cttcatcgaa atcaatccta gaatccaagt    1560
cgaacatacc atcaccgaag aaattaccgg tatcgatata gtttccgccc aaattcaaat    1620
tgctgctggt gctactttga ctcaattggg tttgttgcaa gataagatta ccaccgagg     1680 tttctccatt caatgtagaa ttactaccga agatccatcc aagaacttcc aaccagatac    1740
tggtagattg gaagtttaca gatctgccgg tggtaacggt gttagattgg acggtggtaa    1800
tgcatatgct ggtgcaacta tttctccaca ctatgattct atgttggtca agtgttcttg    1860
ttccggttct acttacgaaa tcgttagaag aaagatgatc agagccttga tcgaattcag    1920
aatcagaggt gttaagacca catcccatt tttgttgacc ttgttgacta acccagtttt     1980
catcgaaggt acttactgga ctaccttcat tgatgatacc ccacaattat tccaaatggt    2040
ttcctcacaa aacagagcac aaaagttgtt gcattacttg gcagatttgg ctgttaacgg    2100
ttcttctatt aagggtcaaa ttggtttgcc aaagttgaag tctaatccat ctgttccaca    2160
cttgcatgat gctcaaggta atgttattaa cgttaccaaa tcagctccac catcaggttg    2220
gagacaagtt ttgttggaaa aaggtccttc cgaattcgct aagcaagtta gacaattcaa    2280
cggtactttg ttgatggata ccacttggag agatgctcat caatctttgt tggctactag    2340
agttagaacc catgatttgg ctacaattgc tccaactact gctcatgctt tagctggtgc    2400
ttttgctttg gaatgttggg gtggtgctac attcgatgtt gctatgagat tcttgcatga    2460
agatccttgg gaaagattga gaaagttgag atctttggtt ccaaacatcc ctttccaaat    2520
gttgttgaga ggtgctaatg tgttgctta ttcttcattg ccagataacg ccattgatca     2580
ctttgttaag caagctaagg ataacggtgt cgatatcttc agagtattcg atgctttgaa    2640
cgacttggaa caattgaagg ttggtgttaa cgctgttaag aaagctggtg gtgttgtaga    2700
agctactgtt tgttattctg gtgacatgtt gcaaccaggt aagaagtaca atttggacta    2760
ctacttggaa gtcgtcgaaa agatagttca aatgggtact catatcttgg gtatcaaaga    2820
tatggctggt actatgaagc cagctgctgc taagttgttg attggttctt tgagaactag    2880
atacccagat ttgccaatcc atgttcattc tcatgattct gctggtacag ctgttgcttc    2940
tatgactgct tgtgccttgg ctggtgctga tgttgtagat gttgcaatca attctatgtc    3000
cggtttgact tctcaaccat ccattaacgc tttgttagct tctttggaag gtaacattga    3060
caccggtatt aacgtcgaac acgttagaga attggatgct tactgggctg aaatgagatt    3120
gttgtactct tgttttgaag ccgatttgaa aggtccagat cctgaagttt atcaacacga    3180
aattccaggt ggtcaattga ctaacttgtt gttccaagct caacaattag gtttgggtga    3240
acaatgggca gaaactaaga gagccttatag agaagccaac tacttgttag gtgatatcgt    3300
taaggttacc ccaacttcta aagttgtagg tgatttggcc caattcatgg tcagtaacaa    3360
attgacctcc gatgacatta gaagattggc taattccttg gatttcccag attccgttat    3420
ggattttttc gaaggtttga tcggtcaacc atacggtggt tttccagaac cattgagatc    3480
tgatgttttg agaaacaaga gaagaaaatt gacttgcaga ccaggtttgg aattggaacc    3540
atttgatttg gaaagatca gagaagactt gcaaaacaga ttcggtgaca tcgatgaatg     3600
tgatgttgcc tcttacaata tgtacccaag agtctacgaa gatttccaaa agattagaga    3660
aacctacggt gacttgtcag ttttgccaac taagaatttc ttggctccag ctgaaccaga    3720
tgaagaaatt gaagttacca tcgaacaagg taagaccttg atcattaagt tgcaagcagt    3780
tggtgacttg aacaaaaaga ctggtcaaag agaagtctac ttcgaattga acggtgaatt    3840
```

```
gagaaaaatc agagttgccg acaagtccca aaacattcaa tcagttgcta agccaaaagc    3900
cgatgttcat gatactcatc aaataggtgc tccaatggcc ggtgttatta gaagttaa     3960 ggttcacaaa ggttccttgg tcaaaaaggg tgaatctatt gctgttttgt ccgccatgaa   4020 gatgaaatg gttgtttctt ctcctgctga tggtcaagtt aaggatgttt tcattaagga   4080
cggtgaatcc gttgatgctt ctgatttgtt ggttgtcttg gaagaagaaa ccttgccacc   4140
atctcaaaag aagtaaattt aactccttaa gttactttaa tgatttagtt tttattatta   4200
ataattcatg ctcatgacat ctcatataca cgtttataaa acttaaatag attgaaaatg   4260
tattaaagat tcctcaggga ttcgattttt ttggaagttt ttgtttttt ttccttgaga    4320 tgctgtagta tttgggaaca attatacaat cgaaagatat atgcttacat tcgaccgttt   4380
tagccgtgat cattatccta tagtaacata acctgaagca taactgacac tactatcatc   4440
aatacttgtc acatgaggcc ttggtggcc                                     4469

<210> SEQ ID NO 10
<211> LENGTH: 3090
<212> TYPE: DNA
<213> ORGANISM: Artificial Sequence
<220> FEATURE:
<223> OTHER INFORMATION: Expression cassette

<400> SEQUENCE: 10
ggccttggtg gccgaataaa aaacacgctt tttcagttcg agtttatcat tatcaatact    60
gccatttcaa agaatacgta aataattaat agtagtgatt ttcctaactt tatttagtca   120
aaaaattagc cttttaattc tgctgtaacc cgtacatgcc caaaataggg ggcgggttac   180
acagaatata taacatcgta ggtgtctggg tgaacagttt attcctggca tccactaaat   240
ataatggagc ccgctttta agctggcatc cagaaaaaaa aagaatccca gcaccaaaat    300
attgttttct tcaccaacca tcagttcata ggtccattct cttagcgcaa ctacagagaa   360
caggggcaca aacaggcaaa aaacgggcac aacctcaatg gagtgatgca acctgcctgg   420
agtaaatgat gacacaaggc aattgaccca cgcatgtatc tatctcatt tcttacacct    480 tctattacct tctgctctct ctgatttgga aaagctgaa aaaaaggtt gaaccagtt     540 ccctgaaatt attcccctac ttgactaata agtatataaa gacggtaggt attgattgta   600
attctgtaaa tctatttctt aaacttctta aattctactt ttatagttag tctttttttt   660
agttttaaaa caccaagaac ttagtttcga ataaacacac ataaacaaac aaaatgatca   720
gacaatccac cttgaagaac ttcgctatta agagatgctt ccaacatatc gcttacagaa   780
atactccagc catgagatct gttgctttgg ctcaaagatt ttactcctca tcctccagat   840
attactctgc ttctccattg ccagcttcta aagaccaga accagctcca tcttttaacg   900
ttgatccatt ggaacaacca gctgaaccat ctaaattggc taaaaagttg agagccgaac   960
cagatatgga tacttctttt gttggtttga ctggtggtca aatcttcaac gaatgatgt   1020 ccagacaaaa cgttgatacc gttttttggtt atccaggtgg tgctattttg ccagtttatg   1080
atgctattca caactccgac aagttcaact tcgttttgcc aaaacatgaa caaggtgctg   1140
gtcatatggc tgaaggttat gctagagctt ctggtaaacc aggtgttgtt ttggttactt   1200
ctggtccagg tgctactaat gttgttactc caatggctga tgctttcgct gatggtattc   1260
caatggttgt ttactctggt caagttccaa catccgctat ggtacagat gcttttcaag   1320 aagctgacgt tgttggtatt tctagatctt gtactaagtg gaacgtcatg gttaagtccg   1380
```

```
ttgaagaatt gccattgaga atcaacgaag ctttcgaaat tgctacatca ggtagaccag    1440
gtccagtttt ggttgatttg cctaaagatg ttactgccgc catttttgaga aatccaattc   1500 caactaagac taccttgcca tccaatgcct tgaatcaatt gacttctaga gcccaagatg    1560
aattcgtcat gcaatctatt aacaaggctg ccgatttgat caacttggca aaaaaaccag    1620
tcttgtatgt tggtgccggt attttgaatc atgctgatgg tccaagatta ttgaaagaat    1680
tgtccgacag agcccaaatt ccagttacta ctactttaca aggtttgggt tccttcgatc    1740
aagaagatcc aaaatccttg acatgttgg gtatgcatgg ttgtgctact gctaatttgg     1800
ctgttcaaaa cgccgacttg attattgctg ttggtgctag atttgatgat agagtcactg    1860
gtaacatttc caagtttgct ccagaagcta ggagagctgc tgctgaaggt agaggtggta    1920
ttattcattt tgaagtctcc ccaaagaata tcaacaaggt tgttcaaacc caaatcgccg    1980
ttgaaggtga tgcaactact aatttgggta agatgatgtc taagatcttc ccagtcaaag    2040
aaagatctga atggttcgct caaatcaaca agtggaagaa agaatacccca tacgcctaca   2100 tggaagaaac tccaggttct aaaatcaagc acaaaccgt tatcaagaag ttgtctaagg     2160
ttgctaacga taccggtaga catgttatcg ttactactgg tgttggtcaa catcaaatgt    2220
gggctgctca acattggact tggagaaatc ctcatacttt cattacatct ggtggtttgg    2280
gtactatggg ttatggtttg ccagctgcta ttggtgctca agttgctaaa ccagaatcct    2340
tggttattga tattgatggt gatgcctctt tcaacatgac cttgactgaa ttatcttccg    2400
ctgttcaagc tggtactcca gttaagattt tgatcttgaa caacgaagaa caaggtatgg    2460
tcacacaatg gcaaagtttg ttctacgaac atagatactc ccataccccat caattgaacc   2520 cagatttcat taagttggct gaagccatgg gttttaaaagg tttgagagtc aaaaagcaag    2580
aagaattgga cgctaagttg aaagaattcg tttctactaa gggtcctgtc ttgttggaag    2640
ttgaagttga taagaaggtt ccagtcttgc ctatggttgc tggtggttca ggtttggatg    2700
aattcattaa ctttgaccca gaagtcgaaa gacaacaaac tgaattgaga cataagagaa    2760
ctggtggtaa gcactaagtg aatttacttt aaatcttgca tttaaataaa ttttctttttt    2820 atagctttat gacttagttt caatttatat actatttaa tgacattttc gattcattga     2880
ttgaaagctt tgtgttttttt cttgatgcgc tattgcattg ttcttgtctt tttcgccaca    2940
tgtaatatct gtagtagata cctgatacat tgtggatgct gagtgaaatt ttagttaata    3000
atggaggcgc tcttaataat tttggggata ttggcttttt ttttaaagt ttacaaatga     3060 attttttccg ccaggatggc cttagtggcc                                     3090
```

<210> SEQ ID NO 11
<211> LENGTH: 1810
<212> TYPE: DNA
<213> ORGANISM: Artificial Sequence
<220> FEATURE:
<223> OTHER INFORMATION: Expression cassette

<400> SEQUENCE: 11

```
ggccttagtg gccgccgtac cacttcaaaa cacccaagca cagcatacta aatttcccct     60
ctttcttcct ctagggtgtc gttaattacc cgtactaaag gttggaaaa gaaaaaagag     120 accgcctcgt ttcttttttct tcgtcgaaaa aggcaataaa aattttatc acgtttcttt    180 ttcttgaaaa tttttttttt tgatttttttt ctctttcgat gacctcccat tgatatttaa    240
gttaataaac ggtcttcaat ttctcaagtt tcagttcat ttttcttgtt ctattacaac     300
tttttttact tcttgctcat tagaaagaaa gcatagcaat ctaatctaag ttttaattac    360
```

```
aaaatgccac attctgttac cccatccatt gaacaagatt ccttgaagat tgctattttg      420
ggtgctgctg gtggtattgg tcaatctttg tctttgttgt tgaaggccca attgcaatac      480
caattgaaag aatccaatag atccgtcacc catattcatt tggccttgta cgatgttaat      540
caagaagcca ttaacggtgt taccgctgat ttgtctcata ttgataccc aatctccgtt       600 tcttcacatt ctccagccgg tggtatagaa aattgcttgc ataatgcttc catcgttgtt      660
attccagctg gtgttccaag aaaaccaggt atgactagag atgatttgtt caacgttaac      720
gccggtatca tttctcaatt gggtgattct attgctgaat gctgcgattt gtctaaggtt      780
ttcgttttgg ttatctccaa cccagttaac tcttggttc cagttatggt cagtaacatc       840
ttgaagaacc atccacaatc tagaaactcc ggtatcgaaa aagaattat gggtgttacc       900 aagttggata tcgttagagc ttctaccttc ttgagagaaa tcaacatcga atctggtttg      960
actccaagag tcaattctat gccagatgtt cctgttattg gtggtcattc tggtgaaacc     1020
attatccctt tgttctccca atctaacttc ttgtccagat gaacgaaga tcaattgaag     1080 tacttgatcc acagagttca atacggtggt gatgaagttg ttaaggctaa aaatggtaag     1140
ggttctgcta ctttgtctat ggctcatgct ggttacaaat gcgttgttca attcgtttcc     1200 tgttgttgg gtaacatcga acaaatccat ggtacttact acgttccatt gaaggatgct      1260
aacaatttcc caattgctcc aggtgctgat caattattgc cattggttga tggtgctgat     1320
tacttcgcta ttccattgac tattactacc aagggtgttt cctacgttga ttacgatatt     1380
gtcaacagaa tgaacgatat ggaaagaaat caaatgttgc caatctgtgt ctcccaattg     1440
aagaagaaca ttgacaaggg tttggaattc gttgcttcta gatctgcttc ttcctaagga     1500
gattgataag acttttctag ttgcatatct tttatattta aatcttatct attagttaat     1560
tttttgtaat ttatccttat atatagtctg gttattctaa aatatcattt cagtatctaa     1620
aaattcccct cttttttcag ttatatctta acaggcgaca gtccaaatgt tgatttatcc     1680
cagtccgatt catcagggtt gtgaagcatt ttgtcaatgg tcgaaatcac atcagtaata     1740
gtgcctctta cttgcctcat agaatttctt tctcttaacg tcaccgtttg gtcttttggc     1800
ctacttggcc                                                            1810

<210> SEQ ID NO 12
<211> LENGTH: 3106
<212> TYPE: DNA
<213> ORGANISM: Artificial Sequence
<220> FEATURE:
<223> OTHER INFORMATION: Expression cassette

<400> SEQUENCE: 12
ggcctacttg gccgggcgcc ataaccaagg tatctataga ccgccaatca gcaaactacc        60
tccgtacatt catgttgcac ccacacattt atacacccag accgcgacaa attacccata       120
aggttgtttg tgacggcgtc gtacaagaga acgtgggaac ttttaggct caccaaaaaa        180 gaaagaaaaa atacgagttg ctgacagaag cctcaagaaa aaaaaattc ttcttcgact        240 atgctggagg cagagatgat cgagccggta gttaactata tatagctaaa ttggttccat       300
caccttcttt tctggtgtcg ctccttctag tgctattct ggcttttcct attttttttt       360
ttccattttt ctttctctct ttctaatata taaattctct tgcattttct attttttctct      420 ctatctattc tacttgttta ttcccttcaa ggtttttttt taaggagtac ttgttttag        480 aatatacggt caacgaacta taattaacta aacatggatg atcaattgaa gcaatctgcc       540
```

```
ttggatttcc atgaatttcc agttccaggt aagatccaag tttctccaac aaaaccattg    600
gctacccaaa gagatttggc tttggcttat tctccaggtg ttgctgctcc atgtttggaa    660
attgaaaaag atccattgaa ggcttacaag tacactgcta gaggtaattt ggttgccgtt    720
atttctaatg gtactgccgt tttgggtttg ggtaatattg gtgctttggc tggtaaacca    780
gttatggaag gtaaaggtgt tttgttcaaa agttcgccg gtatcgatgt tttcgacatc     840
gaagttgatg aattggatcc agacaagttc attgaagttg ttgctgcttt ggaacctact    900
ttcggtggta ttaacttgga agatattaag gctccagaat gcttctacat cgaacaaaag    960
ttgagagaaa gaatgaacat cccagttttc cacgatgatc aacatggtac tgctattatt   1020
tctaccgctg ctattttgaa cggtttgaga gttgttgaaa agaacatctc cgatgtcaga   1080
atggttgttt ctggtgctgg tgctgctgct attgcttgta tgaatttgtt ggttgccttg   1140
ggtttacaaa agcacaacat cgttgtttgc gattccaaag gtgttatcta ccaaggtaga   1200
gaacctaaca tggctgaaac aaaagctgct tatgctgttg ttgatgatgg taagagaacc   1260
ttggatgatg ttattgaagg tgccgatatt ttcttgggtt gttctggtcc aaaagtcttg   1320
actcaagaaa tggttaagaa aatggctaga gccccaatga ttttggcttt agctaatcca   1380
gaaccagaaa tcttgccacc attggctaaa gaagttagac cagacgctat tatctgtacc   1440
ggtagatctg attacccaaa tcaagttaac aacgtcttgt gcttcccatt cattttaga   1500 ggtgctttgg atgttggtgc taccgctatt aacgaagaaa tgaagttggc tgctgttaga   1560
gctattgctg aattggctca tgctgaacaa tcagaagttg ttgcatctgc ttatggtgat   1620
caagatttgt cttttggtcc agaatatatc atcccaaagc cattcgatcc aagattgatc   1680
gttaagattg ctccagctgt tgctaaagct gctatggaat ctggtgttgc tactagacca   1740
attgctgatt cgatgtttta catcgacaag ttgaccgaat cgttacaa gaccaacttg     1800 ttcatgaagc caattttctc acaagctaga aaggctccaa agagagttgt tttgccagaa   1860
ggtgaagaag ctagagtttt acacgctact caagaattag ttaccttggg tttggctaag   1920
ccaattttga ttggtagacc aaacgtcatc gaaatgagaa tccaaaagtt aggtttacaa   1980
atcaaggccg tgttgacttc gaaatcgtt aacaatgaat ctgacccaag attcaaagaa    2040
tactggaccg aatacttcca aatcatgaag agaagaggtg tcactcaaga caagctcaa    2100 agagctttga tttctaaccc aactgttatt ggtgccatca tggttcaaag aggtgaagct   2160
gacgctatga tttgtggtac tgttggtgat taccatgaac acttctctgt tgtcaagaac   2220
gttttcggtt atagagatgg tgttcatact gctggtgcta tgaatgcttt gttgttgcca   2280
tctggtaaca ccttcattgc tgatacttac gttaacgatg aaccagatgc tgaagaattg   2340
gctgaaatta ctttgatggc tgctgaaacc gttagaagat ttggtattga acctagagtt   2400
gccttgttgt cccattctaa ttttggttct tcagactgcc atcctcttc aaaaatgaga    2460 caagctttgg aattggtcag agaaagagca ccagaattga tgattgatgg tgaaatgcat   2520
ggtgatgctc ctttggttga agctattaga aatgatagaa tgccagactc ctcattgaaa   2580
ggttctgcta acattttggt catgccaaat atggaagctg ccagaatttc ttacaacttg   2640
ttgagagtct cttccagtga aggtgtaact gttggtccag ttttgatggg tgttgctaaa   2700
ccagttcatg ttttgactcc aattgcctcc gttagaagaa tcgttaatat ggttgctttg   2760
gccgttgttg aagctcaaac tcaaccattg taagagtaat aattattgct tccatataat   2820 attttttatat acctcttatt tttatgtatt agttaattaa gtattttat ctatctgctt    2880 atcattttct tttcatatag ggggggttgg tgttttcttg cccatcagat tgatgtcctc   2940
```

```
caactcggca ctattttaca aagggttttt ttgtaagaga aggagaagac agatactaaa    3000
ccatacgtta ctcgaaacaa aaaaaaaaaa aatggaaaaa gctgctatca acaaaagacg    3060
gcctcatcaa acctaaagaa accatgtcag cgtggcctgt atggcc                   3106
```

<210> SEQ ID NO 13
<211> LENGTH: 2699
<212> TYPE: DNA
<213> ORGANISM: Artificial Sequence
<220> FEATURE:
<223> OTHER INFORMATION: Expression cassette

<400> SEQUENCE: 13

```
ggcctgtatg gccctactta ttcccttcga gattatatct aggaacccat caggttggtg     60
gaagattacc cgttctaaga cttttcagct tcctctattg atgttacacc tggacacccc    120
ttttctggca tccagttttt aatcttcagt ggcatgtgag attctccgaa attaattaaa    180
gcaatcacac aattctctcg gataccacct cggttgaaac tgacaggtgg tttgttacgc    240
atgctaatgc aaaggagcct atataccttt ggctcggctg ctgtaacagg aatataaag    300 ggcagcataa tttaggagtt tagtgaactt gcaacattta ctattttccc ttcttacgta    360 aatattttc ttttaattc taaatcaatc ttttcaatt ttttgtttgt attctttct         420 tgcttaaatc tataactaca aaaaacacat acataaacta aaatgtggc caatccaaca      480 atccagatta tactcttcta acaccagatc tcataaggct actactacta gagaaaacac    540
cttccaaaag ccatactccg atgaagaagt tactaagact ccagttggtt ctagagccag    600
aaagattttt gaagctccac atccacatgc tactagattg actgttgaag gtgctattga    660
atgcccattg gaatccttcc aattattgaa ctcacctttg ttcaacaagg ttctgctttt    720
cactcaagaa gaaagagaag cttttcaactt ggaagctttg ttgccaccac aagttaacac    780
tttggatgaa caattggaaa gatcctacaa gcaattgtgc tacttgaaaa ctccattggc    840
caagaacgat ttcatgactt ctttgagagt tcaaaacaag gtcttgtact tcgccttgat    900
cagaagacac atcaaagaat tggttccaat catctacact ccaactgaag gtgatgctat    960
tgctgcttat tctcacagat tcagaaaaacc agaaggtgtc ttttggata tcaccgaacc   1020 agattccatt gaatgtagat tggctactta tggtggtgat aaggatgttg attacatcgt   1080
tgtttccgac tccgaaggta ttttgggtat tggtgatcaa ggtataggtg gtgtcagaat   1140
tgctatttct aagttggctt tgatgacctt gtgtggtggt attcatccag gtagagtttt   1200 gccagttgt ttggatgttg gtacaaacaa caaaaagttg gccagagatg aattgtacat    1260
gggtaacaag ttctccagaa tcagaggtaa gcaatacgac gatttcttgg aaaagttcat   1320
caaggccgtt aagaaggttt atccatccgc tgttttacac ttcgaagatt tcggtgttaa   1380
gaacgccaga agattattag aaaagtacag atacgaattg ccatccttca acgatgacat   1440
tcaaggtact ggtgctgttg ttatggcttc tttgattgct gcattgaagc acactaacag   1500
agatttgaaa gataccagag tcttgatcta tggtgctggt tctgctggtt taggtattgc   1560
agatcaaatc gttaaccaca tggttactca tggtgtcgac aaagaagaag ccagaaaaaa   1620
gatcttcttg atggacagaa gaggttttgat attgcaatcc tacgaagcta attctacccc   1680
agctcaacat gtttacgcta aatctgatgc tgaatgggct ggtattaaca ctagatcatt   1740
gcacgatgtt gtcgaaaacg ttaagcctac ttgtttggtt ggttgttcta ctcaagctgg   1800
tgcttttaca caagatgtcg ttgaagaaat gcataagcac aatccaagac ctatcatctt   1860
```

```
cccattgtct aacccaacta gattgcatga agctgttcca gctgatttga tgaagtggac   1920
taacaacaat gctttggttg ctactggttc tccatttcca ccagttgatg gttacagaat   1980
ctctgaaaac aacaactgct actcctttcc aggtattggt ttgggtgctg ttttgtctag   2040
agctactaca attaccgaca agatgatttc tgctgccgtt gatcaattgg ctgaattgtc   2100
tccattgaga gaaggtgatt ctagaccagg tttattgcca ggtttggata ccattactaa   2160
tacctctgct agattggcaa ctgccgttat tttacaagct ttggaagaag gtactgccag   2220
aatcgaacaa gaacaagttc aggtggtgc tccaggtgaa actgttaagg ttccaagaga   2280
ttttgacgaa tgcttgcaat gggttaaggc tcaaatgtgg gaaccagttt acagaccaat   2340
gattaaggtt caacacgatc catccgttca caccaatcaa ttgtaagatt aatataatta   2400
tataaaaata ttatcttctt ttctttatat ctagtgttat gtaaaataaa ttgatgacta   2460
cggaaagctt ttttatattg tttcttttc attctgagcc acttaaattt cgtgaatgtt   2520
cttgtaaggg acggtagatt tacaagtgat acaacaaaaa gcaaggcgct ttttctaata   2580
aaaagaagaa aagcatttaa caattgaaca cctctatatc aacgaagaat attactttgt   2640
ctctaaatcc ttgtaaaatg tgtacgatct ctatatgggt tactcaggcc tctttggcc   2699
```

<210> SEQ ID NO 14
<211> LENGTH: 1475
<212> TYPE: DNA
<213> ORGANISM: Artificial Sequence
<220> FEATURE:
<223> OTHER INFORMATION: Expression cassette

<400> SEQUENCE: 14

```
ggcctctttg gccagatctg tttagcttgc ctcgtcccg ccgggtcacc cggccagcga     60
catggaggcc agaataccc tccttgacag tcttgacgtg cgcagctcag ggcatgatg    120 tgactgtcgc ccgtacattt agcccataca tccccatgta taatcatttg catccataca    180
ttttgatggc cgcacggcgc gaagcaaaaa ttacggctcc tcgctgcaga cctgcgagca    240
gggaaacgct cccctcacag acgcgttgaa ttgtccccac gccgcgcccc tgtagagaaa    300
tataaaaggt taggatttgc cactgaggtt cttctttcat atacttcctt ttaaaatctt    360
gctaggatac agttctcaca tcacatccga acataaacaa ccatgggtaa ggaaaagact    420
cacgtttcga ggccgcgatt aaattccaac atggatgctg atttatatgg gtataaatgg    480
gctcgcgata atgtcgggca atcaggtgcg acaatctatc gattgtatgg gaagcccgat    540
gcgccagagt tgtttctgaa acatggcaaa ggtagcgttg ccaatgatgt tacagatgag    600
atggtcagac taaactggct gacggaattt atgcctcttc cgaccatcaa gcattttatc    660
cgtactcctg atgatgcatg gttactcacc actgcgatcc ccgcaaaac agcattccag    720 gtattagaag aatatcctga ttcaggtgaa aatattgttg atgcgctggc agtgttcctg    780
cgccggttgc attcgattcc tgtttgtaat tgtccttta acagcgatcg cgtatttcgt    840
ctcgctcagg cgcaatcacg aatgaataac ggtttggttg atgcgagtga ttttgatgac    900
gagcgtaatg gctggcctgt tgaacaagtc tggaagaaa tgcataagct tttgccattc    960
tcaccggatt cagtcgtcac tcatggtgat ttctcacttg ataacctat ttttgacgag   1020 gggaaattaa taggttgtat tgatgttgga cgagtcggaa tcgcagaccg ataccaggat   1080
cttgccatcc tatggaactg cctcggtgag ttttctcctt cattacagaa acggcttttt   1140
caaaaatatg gtattgataa tcctgatatg aataaattgc agtttcattt gatgctcgat   1200 gagttttttct aatcagtact gacaataaaa agattcttgt tttcaagaac ttgtcatttg   1260
```

```
tatagttttt ttatattgta gttgttctat tttaatcaaa tgttagcgtg atttatattt    1320
tttttcgcct cgacatcatc tgcccagatg cgaagttaag tgcgcagaaa gtaatatcat    1380
gcgtcaatcg tatgtgaatg ctggtcgcta tactgctgtc gattcgatac taacgccgcc    1440
atccagtgtc gaaaacgagc tcggccttct tggcc                              1475

<210> SEQ ID NO 15
<211> LENGTH: 2508
<212> TYPE: DNA
<213> ORGANISM: Artificial Sequence
<220> FEATURE:
<223> OTHER INFORMATION: Expression cassette

<400> SEQUENCE: 15
ggcctgtttg gccgggtgta caatatggac ttcctctttt ctggcaacca aacccataca      60
tcgggattcc tataatacct tcgttggtct ccctaacatg taggtggcgg aggggagata     120
tacaatagaa cagataccag acaagacata atgggctaaa caagactaca ccaattacac     180
tgcctcattg atggtggtac ataacgaact aatactgtag ccctagactt gatagccatc     240
atcatatcga agtttcacta cccttttttcc atttgccatc tattgaagta ataataggcg     300
catgcaactt cttttctttt ttttctcttt ctctctcccc cgttgttgtc tcaccatatc     360
cgcaatgaca aaaaatgat ggaagacact aaaggaaaaa attaacgaca aagacagcac     420
caacagatgt cgttgttcca gagctgatga ggggtatctc gaagcacacg aaactttttc     480
cttccttcat tcacgcacac tactctctaa tgagcaacgg tatacggcct tccttccagt     540
tacttgaatt tgaaataaaa aaagtttgc tgtcttgcta tcaagtataa atagacctgc     600
aattattaat cttttgtttc ctcgtcattg ttctcgttcc ctttcttcct tgtttcttttt     660 tctgcacaat atttcaagct ataccaagca tacaatcaac tatctcatat acaatgttaa     720
ccagcaacag ctattctctt catgtcggtc atgtaacctc tcaatttctt accaacttgt     780
tcaatggcat gggatctaat ggcttcgtta acatctctca attgaccatt atcaacagca     840
ccttcaggaa tagctttacc caaatcacct ggttgcaatt cagccataaa aggtttcaac     900
aaaggaacgc aagcgtaaga gaacaagtaa ttaccgtatt cagcagtatc ggagataacg     960
acgttcattt cgtataatct ttttctggcg atagtgttag caatcaatgg caattcgtgc    1020
aaggattcgt agtaagcaga ttcttcaatg ataccggagt caaccatagt ttcaaatgcc    1080
aattcaacac cagccttaac catagcgatc atcaaaacac ccttatcgaa gtattcttgt    1140
tcaccaatct taccttcgta ttgtggagca gtttcaaaag cagtcttacc agtttcttct    1200
ctccaagtca caacttctt atcatcatta gcccaatcag ccatcatacc agaagagaat    1260
tcaccggaga taatatcatc catgtgcttt tggaacaaag gggccataat ttctttcaat    1320
tgttcggaca atgcgtaagc tctcaactta gctggattag acaatctgtc catcatcaag    1380
gtaataccac cttgtttcaa agcttcggta atggtttccc aaccaaattg aatcaacttt    1440
tcagcgtaag ctggatcagt accttcttca accaacttat cgaaacacaa caaagaacca    1500
gcttgcaaca taccacacaa aatggtttgt tcacccatca aatcggactt aacttcggca    1560
acaaatgaag attccaaaac accagctcta tgaccaccag tagcagcagc ccaagcttta    1620
gcaatagcca taccttcacc ctttggatca ttttctggat gaacagcaat caaagttgga    1680
acaccgaaac ctctcttgta ttcttctcta acttcagtac ctggacattt tggagcaacc    1740
ataacaacgg tgatatcctt tctgatttgt tcaccgactt caacgatgtt aaaaccatga    1800
```

| | | |
|---|---|---|
| gaataaccca aagcagcacc atccttcatc aatggttgga cagttctaac aacatcagag | 1860 |
| tgttgcttat ctggggtcaa gttaatgacc aaatcagctt gtggaatcaa ttcttcgtaa | 1920 |
| gtaccgacct aaaaccgtt ttcagtagct tttctccaag aggctctttt ttcagcaatg | 1980 |
| gcttcttttc tcaaggcgta agaaatatcc aaaccggagt ctctcatgtt caaaccttga | 2040 |
| tttaaacctt gggcaccaca accaacgata caaccttttt accttgcaa gtaagaagca | 2100 |
| ccatcagcaa attcatctct acccatgaat ctgcatttac ccaattgagc caattgttgt | 2160 |
| ctcaaattca aggtgttgaa gtagttagcc attaagcgaa tttcttatga tttatgattt | 2220 |
| ttattattaa ataagttata aaaaaaataa gtgtatacaa attttaaagt gactcttagg | 2280 |
| ttttaaaacg aaaattctta ttcttgagta actctttcct gtaggtcagg ttgctttctc | 2340 |
| aggtatagca tgaggtcgct cttattgacc acacctctac cggcatgccg agcaaatgcc | 2400 |
| tgcaaatcgc tccccatttc acccaattgt agatatgcta actccagcaa tgagttgatg | 2460 |
| aatctcggtg tgtattttat gtcctcagag acaaggcct tgatggcc | 2508 |

<210> SEQ ID NO 16
<211> LENGTH: 3045
<212> TYPE: DNA
<213> ORGANISM: Artificial Sequence
<220> FEATURE:
<223> OTHER INFORMATION: Expression cassette

<400> SEQUENCE: 16

| | | |
|---|---|---|
| ggccttgatg gccactggta gagagcgact ttgtatgccc caattgcgaa acccgcgata | 60 |
| tccttctcga ttctttagta cccgaccagg acaaggaaaa ggaggtcgaa acgtttttga | 120 |
| agaaacaaga ggaactacac ggaagctcta agatggcaa ccagccagaa actaagaaaa | 180 |
| tgaagttgat ggatccaact ggcaccgctg gcttgaacaa caataccagc cttccaactt | 240 |
| ctgtaaataa cggcggtacg ccagtgccac cagtaccgtt accttcggt atacctcctt | 300 |
| tccccatgtt tccaatgccc ttcatgcctc aacggctac tatcacaaat cctcatcaag | 360 |
| ctgacgcaag ccctaagaaa tgaataacaa tactgacagt actaaataat tgcctacttg | 420 |
| gcttcacata cgttgcatac gtcgatatag ataataatga taatgacagc aggattatcg | 480 |
| taatacgtaa tagttgaaaa tctcaaaaat gtgtgggtca ttacgtaaat aatgatagga | 540 |
| atgggattct tctattttc cttttttccat tctagcagcc gtcggaaaa cgtggcatcc | 600 |
| tctctttcgg gctcaattgg agtcacgctg ccgtgagcat cctctctttc catatctaac | 660 |
| aactgagcac gtaaccaatg gaaaagcatg agcttagcgt tgctccaaaa aagtattgga | 720 |
| tggttaatac catttgtctg ttctcttctg actttgactc ctcaaaaaaa aaaaatctac | 780 |
| aatcaacaga tcgcttcaat tacgccctca caaaaacttt tttccttctt cttcgcccac | 840 |
| gttaaatttt atccctcatg ttgtctaacg gatttctgca cttgatttat tataaaaaga | 900 |
| caaagacata atacttctct atcaattca gttattgttc ttccttgcgt tattcttctg | 960 |
| ttcttcttttt tcttttgtca tatataacca taaccaagta atacatattc aaaatgttac | 1020 |
| aaatcagtaa cacaaccttc agaagctggt ctagtcaatt tagcaaactt agccaaaaca | 1080 |
| cctcttgtag cttttggagt aggttttggg tagttggctc tcctcttagc aatttcttca | 1140 |
| tctgaaacct tcaaggagat ggagttgtta acggcatcaa tttcgatgat gtcgtcatct | 1200 |
| tcaaccaaac ctattaaacc accttcaaca gcttcaggga caatatgacc aacaacaaaa | 1260 |
| ccatgagtac caccagagaa tctaccatca gtaatcaagg cacaagattt acccaaacca | 1320 |
| gcaccaatca aagcagaagt aggtttcaac atttctggca tacctggacc accaactgga | 1380 |

```
ccaatgtttc taataacagc aacatcacca gcatgcaatc taccagattc gataccgtcg    1440
atgaaatgtt gttcaccatc aaaaactcta gcagtaccct tgaagaattc accttcttta    1500
ccagagattt tagcaacgga accaccttga gccaaattac catacaagat ttgcaagtga    1560
ccagtagcct tgattggatt cttcaatggt ctcataatat cttgggagtc gaaatccaaa    1620
tccaaagcag tttcaacgtt ttcggccaat gttttacctg taacagtcaa gcaatcaccg    1680
tgcaatttac cttcttttcaa caagtatttc aaaacagctg gcaaaccacc aatcttatgc    1740
aagtcttcca tcatgtactt accggatggt ttaaaatcac ccaagactgg agtaatatcg    1800
gagattcttt ggaagtcatc ttgagtaatt caacaccga tagcgttagc cattgcaata    1860
atatgcaaga cggcatttgt agaaccaccc aaaaccataa cgatggtgat ggcgttttca    1920
aaagcttctt tggtcatgat gtcggatggc ttgatatcct tttccaacaa gttcttaatg    1980
gccaaaccaa tttcgtcgca ttcttcttgc ttttcttgag aaacggctgg attagatgaa    2040
gagtatggca agacatacc caaggtttca atagcagcag ccaaagtatt agcagtatac    2100
ataccaccac aagcaccttg acctggaatg gcattgcata taacaccatg gtaatcttca    2160
tcggagatgt taccagtaat cttttgaccc aaagattcaa aggcggaaac gatgttcaac    2220
ttttcacctt tgtattcacc gtgttcaata gtaccaccgt aaaccataat ggatggtcta    2280
ttcaatctgg ccataccaat aatggaacct ggcatattct tatcgcaacc tggaatagca    2340
actatagcat cgtaatattc ggcaccagca ttagtttcaa tggaatcggc aataacttct    2400
ctactgacca aggagtatct catacccaat ttaccattag caataccatc agaaacaccg    2460
atggtatgga attgtaaacc gatcaaacca tcagtttgat taacagagga cttgatcttg    2520
gaacccaaag tacccaaatg catattgcat ggattaccat cccaatccat agaaacgata    2580
ccaacttggg ctttcttgaa atcttcgtcc ttgaaaccaa taccgtaata catagcttgt    2640
gtagctggtt gagttggatc ttgagtcaag gtcttagagt acttgttcaa ttcaacggat    2700
tcgaccttac cgttgtactt gaattccatt aagttaattc aaattaattg atatagtttt    2760
ttaatgagta ttgaatctgt ttagaaataa tggaatatta tttttatta tttatttata    2820 ttattggtcg gctcttttct tctgaaggtc aatgacaaaa tgatatgaag gaaataatga    2880
tttctaaaat tttacaacgt aagatatttt tacaaaagcc tagctcatct tttgtcatgc    2940
actattttac tcacgcttga aattaacggc cagtccactg cggagtcatt tcaaagtcat    3000
cctaatcgat ctatcgtttt tgatagctca ttggcctcga tggcc    3045
```

<210> SEQ ID NO 17
<211> LENGTH: 2405
<212> TYPE: DNA
<213> ORGANISM: Artificial Sequence
<220> FEATURE:
<223> OTHER INFORMATION: Expression cassette

<400> SEQUENCE: 17

```
ggcctcgatg gcctcgtagg aacaatttcg ggccctgcg tgttcttctg aggttcatct    60
tttacatttg cttctgctgg ataatttca gaggcaacaa ggaaaaatta gatggcaaaa    120
agtcgtcttt caaggaaaaa tccccaccat ctttcgagat cccctgtaac ttattggcaa    180
ctgaaagaat gaaaggagg aaatacaaa atatactaga actgaaaaaa aaaagtata    240 aatagagacg atatatgcca atacttcaca atgttcgaat ctattcttca tttgcagcta    300
ttgtaaaata ataaaacatc aagaacaaac aagctcaact tgtctttct aagaacaaag    360
```

```
aataaacaca aaaacaaaaa gttttttttaa ttttaatcaa aaaatgttag tagaattggt      420
ctggcaacat agttttaccc aaagccttgt tgtcagagta atcgattgga atatcaacaa      480
cgactggacc atcagtagca aaagcttgat ccaaaacctt ttccaaatca gcaggttgat      540
taactctcaa acctgtagca ccaaaagatt cggcgtactt aacaaaatca actggaccaa      600
aatgaacagc agcatcttca ccgtacttca tttcttcttg aacttaacc atatcgtaag      660 taccgtcgtt ccagatcaaa tgaacgatgt tttgtttcaa tctaacggcg gtttccaatt      720
cttgggcaga aaacaaaaaa ccaccatcac cagaaacgga aactatttga gtatctggtc      780
taaccaaagc agctgcaata gcccatggta aagcaacacc caaagtttgc ataccgttag      840
agaacaacaa gtgtctaggt tcataggatc tgaaatgtct agccatccaa atgtaatggg      900
aaccaacatc aacggtaaca gtcatatcat cagaaactct tgttgcaag gctgcaataa      960 cagacaatgg atggttcaac ttggattgct tatcgatgtt tggaacgaag tctctggttt     1020
gcaatctttc ttgcaattca cccaaataag ctctagcaga atcggaaata tcgtaaccct     1080
tcatgtaagg caacaagaaa tccaaggttt gagcaatatc accgatcaat tcggtttctg     1140
gttgaaaatt atgatcgatt tcggctctca tggcatcaat aacaacgatt ctagatttac     1200
cttcggcgtt ccaatttcta ggttcgtatt caattggatc gtaaccaacg gcaataacca     1260
aatcggactt cttcaataac atgtcacctg gttgatttct gaacaaacca actctaccga     1320
agaagtgatt agcttccaaa tctctggaaa taacaccggc agcttgaaaa gtttcaacaa     1380
caggcaaatt agctgcagca accaaatttc tgatagcctt agtaacttct ggtgaagaag     1440
ctctcatacc aaccaacaaa actggcaact agcagcctt aatcttttga gctaacaaag     1500
tagcttcaac tggagaagct ggacccaatt ttggagcttg aattggggta ataactggag     1560
ttctaactat agagtcggta acatcttgtg gaacagaaac aaaagaagca ccttgtttag     1620
cagctgtagc ttcttggtaa gcattggcca aaacttcaga gatgttttct ggttcttgaa     1680
cttcagcaga gtacttagtg attggcttga acaaagcagc attgttcata gattgatggg     1740
tcaatctcaa caaatcggct ctttgaactt gaccagaaat agccaaaact ggatcacctt     1800
cagcagtagc agtaaccaaa ccagtagcca aattagatgc acctggacca gaagtagtca     1860
taacaacacc tggtttacca gtaattctac caataccagc agcaataaaa gcagcgtttt     1920
gttcatgtct ggtaacgatc aatcttggag acttcggatt aactgggtgt tccaatcttt     1980
cgaaaactct atcgatctta gcacctggaa taccgaaaac gtacttgaca tcatgattaa     2040
ccaaggagtc aacgatagca tcggcaccat aatactttt gtctggcatt aatttgcgaa     2100
cacttttatt aattcatgat cacgctctaa tttgtgcatt tgaaatgtac tctaattcta     2160
attttatatt tttaatgata tcttgaaaag taaatacgtt tttaatatat acaaaataat     2220
acagtttaat tttcaagttt ttgatcattt gttctcagaa agttgagtgg gacggagaca     2280
aagaaacttt aaagagaaat gcaaagtggg aagaagtcag ttgtttaccg accgcactgt     2340
tattcacaaa tattccaatt ttgcctgcag acccacgtct acaaatttg gtggccttgt     2400 tggcc                                                                 2405
```

<210> SEQ ID NO 18
<211> LENGTH: 2629
<212> TYPE: DNA
<213> ORGANISM: Artificial Sequence
<220> FEATURE:
<223> OTHER INFORMATION: Expression cassette

<400> SEQUENCE: 18

```
ggccttgttg gccttgagat aagcacactg cacccatacc ttccttaaaa acgtagcttc      60 cagttttgg tggttccggc ttccttcccg attccgcccg ctaaacgcat attttgttg       120 cctggtggca tttgcaaaat gcataaccta tgcatttaaa agattatgta tcctcttctg     180
acttttcgtg tgatgaggct cgtggaaaaa atgaataatt tatgaatttg agaacaattt    240
tgtgttgtta cggtatttta ctatggaata atcaatcaat tgaggatttt atgcaaatat    300
cgtttgaata ttttccgac cctttgagta cttttcttca taattgcata atattgtccg     360
ctgccccttt ttctgttaga cggtgtcttg atctacttgc tatcgttcaa caccaccta     420 ttttctaact attttttttt tagctcattt gaatcagctt atggtgatgg cacatttttg   480 cataaccta gctgtcctcg ttgaacatag gaaaaaaaa tatataaaca aggctctttc     540
actctccttg caatcagatt tgggtttgtt ccctttattt tcatatttct tgtcatattc   600
ctttctcaat tattattttc tactcataac ctcacgcaaa ataacacagt caaatcaatc   660
aaaatgttaa gacttgtttt gttctgcgaa caatttaccc atcttcttca aaaccttgg   720 agcaccttct ttagccaaga tcaattcgat ccagtacatt ctatttggat cagcttgagc   780
ttccttcata acggagacaa attcgttttc ggttctaact atcttggaaa caactctatc   840
ttcggtagca ccaaaagatt ctggcaactt agagtagttc cacattggaa tatcgttgta   900
ggattgattt ggaccgtgaa tttctctttc gacagtgtaa ccatcgttgt tgatgatgaa   960
gcagattggg ttaatctttt ctctaatggc caaacccaat tcttgaacgg tcaattgcaa  1020
tgaaccgtca ccaatgaaca acaagtgtct agattctttg tcagcaattt gagaacccaa  1080
agcagctgga aaagtataac aatagaacc ccacaatggt tgaccaatga atgagactt    1140 ggacttcaag aaaatggaag aggcaccgaa aaagaagta ccttgttcag caacgatagt    1200
ttcgttagat tgggtcaagt tttcaacagc ttgccacaat ctatcttgag acaacaaggc   1260
attggatgga acgaaatctt cttgcttctt gtcgatgtat ttacccttgt attcaatttc   1320
ggacaagtcc aacaaagagg agatcaaaga ttcgaagtcg aagttttgga ttctttcgtt   1380
gaagatctta ccttcatcga tgttcaagga gatcatcttg ttttcgttca aatgatgagt   1440
gaaagcacca gtagaagaat cggtcaactt aacacccaac atcaagatga aatcggcgga   1500
ttcaacgaat tctttcaagt taggttcgga caaagtacca ttgtagatac ccaagaaaga   1560
tggcaaagct tcatcaacag atgacttacc gaagttcaa gtggtgattg gcaacttggt    1620
cttagaaatg aattgagtga cggtcttttc caaaccgaaa ctgatgattt cgtgaccagt   1680
aataacgatt ggcttcttag cgttcttcaa ggattcttgg atcttgttca aaatttcttg   1740
gtcggaggtg ttggaagtgg agttttcttt cttcaatggc aaagatggtt tttcagcttt   1800
agcagcagca acatcaacag gcaagttgat gtagactggt tttctttctt tcaacaaagc   1860
ggacaaaact ctatcgattt cgacggtagc attttcagca gtcaacaaag ttctagcagc   1920
agtaactggt tcgtgcatct tcataaagtg cttaaaatca ccatcggcca agtatgatg    1980 aacgaattta ccttcgtttt gaaccttaga agttggagaa ccaacgattt caacaactgg   2040
caaattttca gcgtaagaac cagccaaacc attaacagca gacaattcac caacaccgaa   2100
agtagtcaaa aaagcagcag cctttttgt tctagcgtaa ccatcagcca tataagaagc   2160
gttcaattcg ttagcattac caacccactt catatctttg tgggagatga tttggtccaa   2220
gaattgcaag ttgtaatcac ctggaacacc aaagatttct tcgatacccca attcatgcaa   2280 tctatccaac aagtaatcac caacggtgta cattaagcga tttaatctct aattattagt   2340
```

-continued

```
taaagttttta taagcatttt tatgtaacga aaaataaatt ggttcatatt attactgcac    2400
tgtcacttac catggaaaga ccagacaaga agttgccgac agtctgttga attggcctgg    2460
ttaggcttaa gtctgggtcc gcttctttac aaatttggag aatttctctt aaacgatatg    2520
tatattcttt tcgttggaaa agatgtcttc caaaaaaaaa accgatgaat tagtggaacc    2580
aaggaaaaaa aaagaggtat ccttgattaa ggaacaggcc tgattggcc               2629
```

<210> SEQ ID NO 19
<211> LENGTH: 2735
<212> TYPE: DNA
<213> ORGANISM: Artificial Sequence
<220> FEATURE:
<223> OTHER INFORMATION: Expression cassette

<400> SEQUENCE: 19

```
ggcctgattg gccaaagatg ccgatttggg cgcgaatcct ttattttggc ttcaccctca      60
tactattatc agggccagaa aaaggaagtg tttccctcct tcttgaattg atgttaccct     120
cataaagcac gtggcctctt atcgagaaag aaattaccgt cgctcgtgat ttgtttgcaa     180
aaagaacaaa actgaaaaaa cccagacacg ctcgacttcc tgtcttccta ttgattgcag     240
cttccaattt cgtcacacaa caaggtccta gcgacggctc acaggttttg taacaagcaa     300
tcgaaggttc tggaatggcg ggaaagggtt tagtaccaca tgctatgatg cccactgtga     360
tctccagagc aaagttcgtt cgatcgtact gttactctct ctcttcaaa cagaattgtc      420 cgaatcgtgt gacaacaaca gcctgttctc acacactctt ttcttctaac caaggggtg      480 gtttagttta gtagaacctc gtgaaactta catttacata tatataaact tgcataaatt     540
ggtcaatgca agaaatacat atttggtctt ttctaattcg tagttttttca agttcttaga    600 tgctttcttt ttctcttttt tacagatcat caaggaagta attatctact ttttacaaca     660
aatataaaac atgttaggca tccaaaacac aaccgttaga agcattagaa accaacttgg     720
cgtacttaga caaagtaccct cttgtatatc ttggtggtgg agcaacccaa gattgttttc    780
tttgggccat ttctttgtca ctgaccaaca aatcaatctt gttgttgtcg gcatcaatga     840
taatttcgtc accatctcta accaaaccaa ttggaccacc ttctgcagct tcagggacaa     900
tatgaccaat caagaaacca tgagaaccac cagagaatct accatcggtt aacaaagcaa     960
catctttacc caaaccgtaa cccatcaaag cagaagatgg tttcaacatt tctggcatac    1020
ctggagcacc tcttggacct tcatatctaa tgacaacaac ggtcttttca cccttcttga    1080
tttcacctct ttccaaagct tcaatgaaag caccttcttc ttcaaagact ctagctctac    1140
ccttgaagta agtaccttct ttaccagtaa ttttaccaac agcaccacct ggagccaaag    1200
aaccatacaa gatttgcaag tgaccattag ccttgattgg atgagacaat ggcttaatga    1260
tttcttgacc ttctggcaaa gatggagctt ttttagctct ttcagccaaa gtatcaccag    1320
taacagtcat agtgttaccg tgcaacatat tgttttcgta caagtactta atgacggatt    1380
gagtaccacc aacgttaatc aaatcggcca taacgtactt accagatggt ttaaaatcac    1440
cgatcaatgg agtggtatca gagattcttt ggaaatcatc tggagacaac ttaacaccag    1500
cagaatgagc aacagcaacc aaatgtaaaa cagcattggt agaaccacct gtagcaacaa    1560
cgtaagtgat agcgttttcg aaagcttctt tggtcaagat atctcttggc aagataccca    1620
attccatggt cttttttgata tattcaccaa tgttatcaca ttcagccaat tttctctttac   1680 tgacggctgg gaaagatgaa gagtttggaa tagtcaaacc caaaacttca gcagcagaag    1740
ccatggtatt agcagtatac ataccaccac atgaacctgg acctggacaa gcatgttcaa    1800
```

```
caacgtcttc tctttcttct tcggtgaatt gcttagagat atattcaccg taagattgaa    1860
aggcggaaac gatatcgatg ttcttggaaa tcttagagga accacaagtt ggatgacctg    1920
gcaaaatagt accaccgtaa accataatgg atggtctatt atgtctaccc atagccatca    1980
ttacacctgg catattctta tcgcaagatg gaatagcaat gttggcatcg taatgttgag    2040
ccatcataat ggtttcgaaa gaatcggcga taatttctct ggattgcaag gagtatctca    2100
taccttttgt acccatagag ataccatcgg aaacaccaat agtgttgaat tgcatggctt    2160
tcaaaccagc cttttcaata gattgggagc atctgttgtt caagtccaac aagtgcatat    2220
tacatggatt accagaccac caacaagaac caacaccgac ttgtggcttt ttgaaatctt    2280
ctttcttgaa accagtagca tacaacatag cttgagaagc accttgacct ttaggttcgg    2340
taataatgta ggagtacttg ttcaacttct tggcaacaca tctagtagta gagaattgtc    2400
tagaggtagc aaccttagtc aacaaaccca ttaagaaata aattgaattg aattgaaatc    2460
gatagatcaa tttttttctt ttctctttcc ccatccttta cgctaaaata atagtttatt    2520
ttattttttg aatatttttt atttatatac gtatatatag actattattt atcttttaat    2580
gattattaag attttttatta aaaaaaaatt cgctcctctt ttaatgcctt tatgcagttt    2640 tttttttccca ttcgatattt ctatgttcgg gttcagcgta ttttaagttt aataactcga    2700
aaattctgcg ttcgttaaag ctggcctttg tggcc                               2735

<210> SEQ ID NO 20
<211> LENGTH: 2520
<212> TYPE: DNA
<213> ORGANISM: Artificial Sequence
<220> FEATURE:
<223> OTHER INFORMATION: Expression cassette

<400> SEQUENCE: 20
ggcctttgtg gccaggattt taatctgttg gagttaaggt gaatacgttt ttccatattg      60
gggtatgcag ctcgaaccta agtggtatg tacacatccc ctcaagcaca cccattaccc     120
ttataggatt aatgtaagca acagcttaca cggaattgga atactattc aacgatccat     180 gcatctgcca gattcggaca tgcatattcc ccaattggat atagaaaatt aacgtaaggc     240
agtatctttt cacaatgtac ttgcaacgcg gcgacttaaa gttgaagtac aacctgcagc     300
agcggctttt tgtacggtac gccaaactgt caatggataa tattgcgtag accgaaaaag     360
gtaatcctca cactacccg tggtggatga cctaaagcag taatattggt tggaattatc     420
tcccagacgg caccgtctcc ccgagaaagc ttagccccga ggtctaccct ccatacacca    480
ctgattgctc cacgtcatgc ggccttcttt cgaggacaaa aaggcatata tcgctaaaat     540
tagccatcag aaccgttatt gttattatat tttcattacg aaagaggaga gggcccagcg     600
cgccagagca cacacggtca ttgattactt tatttggcta agatccatc ccttctcgat    660 gtcatctctt tccattcttg tgtatttttg attgaaaatg attttttgtc cactaatttc     720
taaaaataag acaaaaagcc tttaagcagt ttttcatcca ttttactacg gtaaaatgaa     780
ttagtacggt atggctccca gtcgcattat ttttagattg gccgtagggg ctggggtaga    840
actagagtaa ggaacattgc tctgccctct tttgaactgt catataaata cctgacctat     900
tttattctcc attatcgtat tatctcacct ctctttttct attctcttgt aattattgat     960
ttatagtcgt aactacaaag acaagcaaaa taaaatacgt tcgctctatt aagatgttat    1020
tgatttcttg gtcttaactt tctgacttct ttaccaacct tccagatttc catgtttctg    1080
```

```
atggtgtcca attctttttc caattttttct ctgtaatctg gttgggagtt gaattccaag    1140
gatctcttag tttcagtacc gttcttagta gattcgtaca agtcttggaa aactggcttc    1200
aaggcattct tgaaaattgg ataccaatcc aaagcacctc ttctagcagt agtagaacaa    1260
gcatcgtaca tgtagtccat accgtattta ccaatcaatg ggtataatga ttgggtggct    1320
tcttcaactg tttcgttgaa agcttcagat ggagaatgac cattttctct caagacatcg    1380
tattgggcca aaacatacc atgaatacca cccatcaaac aacctctttc accatacaag    1440
tcagaattga cttctctttc gaaggtggtt tggtaaacat aaccagaacc aatagcaaca    1500
gccaaagctt gagcttttc gtgagcttta ccagtaacat cattccaaac agcgtaagag    1560
gagttgatac ctctaccttc tttgaacaaa gatctaacag ttctaccaga acccttggaa    1620
gcaaccaaaa taacatccaa atcctttggt ggttcaacat gggtcaaatc cttgaaaact    1680
ggtgaaaaac catgggagaa gtacaaggtc ttacccttag tcaataatgg cttaatagct    1740
ggccaagttt cagattgagc agcatcagac aacaagttca taacgtaaga acctctcttg    1800
atggcatctt caacagtgaa caaattctta cctggaaccc aaccatcttc aatagcagct    1860
ttccaagaag caccatcttt tctaacaccg atgataacgt tcaaaccgtt gtctctcaaa    1920
ttcaaacctt gaccataacc ttgagaacca taaccaatca aggcgaaggt atcgttcttg    1980
aagtaatcca acaactttc tctaggccaa tcagctcttt cgtaaacggt ttcaacagta    2040
ccaccgaagt tgatttgctt caaacctctg gtagtaatca ttggcttaac aaatcttgca    2100
gctggtctag aataagcagc agctctagta gccaaagcga agttctctct ggcagtaata    2160
actctggaat tgcagatcaa tctagcagct tgagttctca acattaaacg gtggtgtttg    2220
acacatccgc cttcttaatg ctttctttca gtattatgtt atttttttgt tattcgtttt    2280
tcacttctag gcttttttgac agactagccc cgttatacca ccatctttgt gggaaagccc    2340
ctaaattgcc ctgagcagta tcgtttcatg tctagtctct ttaaagatgt ttcttacgcg    2400
ttgcgtgtaa aacatcctct cattcaagac agggttttct aaaagcaata ggggtagttt    2460
aataattctt atataatcat catatacact attttttagtt cttaattggc ctgtctggcc    2520
```

<210> SEQ ID NO 21
<211> LENGTH: 2415
<212> TYPE: DNA
<213> ORGANISM: Artificial Sequence
<220> FEATURE:
<223> OTHER INFORMATION: Expression cassette

<400> SEQUENCE: 21

```
ggcctgtctg gcccttccct tttacagtgc ttcggaaaag cacagcgttg tccaagggaa      60
caatttttct tcaagttaat gcataagaaa tatcttttttt tatgtttagc taagtaaaag    120
cagcttggag taaaaaaaaa aatgagtaaa tttctcgatg gattagtttc tcacaggtaa    180
cataacaaaa accaagaaaa gcccgcttct gaaaactaca gttgacttgt atgctaaagg    240
gccagactaa tgggaggaga aaagaaacg aatgtatatg ctcatttaca ctctatatca    300
ccatatggag gataagttgg gctgagcttc tgatccaatt tattctatcc attagttgct    360
gatatgtccc accagccaac acttgatagt atctactcgc cattcacttc cagcagcgcc    420
agtagggttg ttgagcttag taaaaatgtg cgcaccacaa gcctacatga ctccacgtca    480
catgaaacca caccgtgggg ccttgttgcg ctaggaatag gatatgcgac gaagacgctt    540
ctgcttagta accacaccac attttcaggg ggtcgatctg cttgcttcct ttactgtcac    600
gagcggccca taatcgcgct tttttttttaa aaggcgcgag acagcaaaca ggaagctcgg    660
```

```
gtttcaacct tcggagtggt cgcagatctg gagactggat ctttacaata cagtaaggca      720
agccaccatc tgcttcttag gtgcatgcga cggtatccac gtgcagaaca acatagtctg      780
aagaaggggg ggaggagcat gttcattctc tgtagcagta agagcttggt gataatgacc      840
aaaactggag tctcgaaatc atataaatag acaatatatt ttcacacaat gagatttgta      900
gtacagttct attctctctc ttgcataaat aagaaattca tcaagaactt ggtttgatat      960
ttcaccaaca cacacaaaaa acagtacttc actaaattta cacacaaaac aaaatgttag     1020
tcggagaatt ctttgtcgta accaaccaaa gtgaatctgt atctgacgtc ccctttcc       1080 attctttcaa aagcttcatg aacaccagct tcaccaactg gcaaagtttc aacccaaatc     1140
ttgatgtcct tttcggaaac caacttcaat aattgattca attctttgat ggaacccaaa     1200
gcagaataag aaatagaaac ggccttcaaa ccgtatggtt tcaaggacaa catttcgtgt     1260
tgttctggaa tggaaatgga aactattcta ccaccaacct tcatggcctt tggcataatg     1320
ttgaaatcaa tatcagtcaa ggaagaagcg cagacaacga tcaaatcaaa agtatcgaag     1380
tacttttcac cccagtcacc ttcttccaaa gtagcaatat aatgatcggc acccatcttc     1440
attgcatctt ctcttttttct agaggatcta gaaatgacgt aggtttcagc acccatagct     1500
ttagaaatca aagtacccat agaaccaata ccacccaaac caactatacc aacctttta     1560 cctggaccac aaccatttct aaccaatggg aataaacag tcaaaccacc acacaataat     1620
ggagcagcca aatgagatgg gatgttttct gggattggaa caacgaaatg ttcgtgaact     1680
ctaacgtagt tagcgtaacc accttgagaa acataaccat cttcgtatgg ttgagagtaa     1740
gtggtaacga acttagtaca gtatggttcg ttatcgttct tgcatctatc gcattccaaa     1800
caagaaaaaa cttgagcacc aacaccaact ctttgaccaa ctttcaaacc ggagttagac     1860
tttggaccca acttaacaac tttaccaacg atttcgtgac caacaaccaa tggcatcttc     1920
atattccccc aatgaccagc agcacaatga atatcggaac cgcaaacacc acaagcttca     1980
atcttaatgt cgatatcatg atcgtagaat ggctttggat cgtacttagt ctttttggg     2040 ttcttccaat cttcgtgtga ttgaatggca ataccttcga acttttctgg gtaggacatt     2100
aaataaagca atcttgatga ggataatgat ttttttttga atatacataa atactaccgt     2160
ttttctgcta gattttgtga agacgtaaat aagtacatat tactttttaa gccaagacaa     2220
gattaagcat taactttacc cttttctctt ctaagtttca atactagtta tcactgttta     2280
aaagttatgg cgagaacgtc ggcggttaaa atatattacc ctgaacgtgg tgaattgaag     2340
ttctaggatg gtttaaagat ttttcctttt tgggaaataa gtaaacaata tattgctgcc     2400
ttggcctatg tggcc                                                      2415
```

<210> SEQ ID NO 22
<211> LENGTH: 4475
<212> TYPE: DNA
<213> ORGANISM: Artificial Sequence
<220> FEATURE:
<223> OTHER INFORMATION: Expression cassette

<400> SEQUENCE: 22

```
ggcctatgtg gcctccctgc gcggctaaag ttaaggatgc aaaaaacata agacaactga       60
agttaattta cgtcaattaa gttttccagg gtaatgatgt tttgggcttc cactaattca      120
ataagtatgt catgaaatac gttgtgaaga ggatccagaa ataatgaaaa gaaacaacga      180
aactgggtcg gcctgttgtt tcttttcttt accacgtgat ctgcggcatt tacaggaagt      240
```

```
cgcgcgtttt gcgcagttgt tgcaacgcag ctacggctaa caaagcctag tggaactcga    300
ctgatgtgtt agggcctaaa actggtggtg acagctgaag tgaactattc aatccaatca    360
tgtcatggct gtcacaaaga ccttgcggac cgcacgtacg aacacatacg tatgctaata    420
tgtgttttga tagtacccag tgatcgcaga cctgcaattt ttttgtaggt ttggaagaat    480
atataaaggt tgcactcatt caagatagtt ttttcttgt gtgtctattc attttattat     540
tgtttgttta aatgttaaaa aaccaagaa cttagtttca aattaaattc atcacacaaa     600
caaacaaaac aaaatgttac ttcttttgag atggtggcaa ggtttcttct tccaagacaa    660
ccaacaaatc agaagcatca acggattcac cgtccttaat gaaaacatcc ttaacttgac    720
catcagcagg agaagaaaca accatttcca tcttcatggc ggacaaaaca gcaatagatt    780
cacccttttt gaccaaggaa cctttgtgaa ccttaacttc tataataaca ccggccattg    840
gagcacctat ttgatgagta tcatgaacat cggcttttgg cttagcaact gattgaatgt    900
tttgggactt gtcggcaact ctgatttttc tcaattcacc gttcaattcg aagtagactt    960
ctctttgacc agtcttttg ttcaagtcac caactgcttg caacttaatg atcaaggtct    1020
taccttgttc gatggtaact tcaatttctt catctggttc agctggagcc aagaaattct    1080
tagttggcaa aactgacaag tcaccgtagg tttctctaat cttttggaaa tcttcgtaga    1140
ctcttgggta catattgtaa gaggcaacat cacattcatc gatgtcaccg aatctgtttt    1200
gcaagtcttc tctgatcttt tccaaatcaa atggttccaa ttccaaacct ggtctgcaag    1260
tcaattttct tctcttgttt ctcaaaacat cagatctcaa tggttctgga aaaccaccgt    1320
atggttgacc gatcaaacct tcgaaaaaat ccataacgga atctgggaaa tccaaggaat    1380
tagccaatct tctaatgtca tcggaggtca atttgttact gaccatgaat tgggccaaat    1440
cacctacaac tttagaagtt ggggtaacct taacgatatc acctaacaag tagttggctt    1500
ctctataagc tctcttagtt tctgcccatt gttcacccaa acctaattgt tgagcttgga    1560
acaacaagtt agtcaattga ccacctggaa tttcgtgttg ataaacttca ggatctggac    1620
ctttcaaatc ggcttcaaaa caagagtaca acaatctcat ttcagcccag taagcatcca    1680
attctctaac gtgttcgacg ttaataccgg tgtcaatgtt accttccaaa gaagctaaca    1740
aagcgttaat ggatggttga gaagtcaaac cggacataga attgattgca acatctacaa    1800
catcagcacc agccaaggca caagcagtca tagaagcaac agctgtacca gcagaatcat    1860
gagaatgaac atggattggc aaatctgggt atctagttct caaagaacca atcaacaact    1920
tagcagcagc tggcttcata gtaccagcca tatctttgat acccaagata tgagtaccca    1980
tttgaactat cttttcgacg acttccaagt agtagtccaa attgtacttc ttacctggtt    2040
gcaacatgtc accagaataa caaacagtag cttctacaac accaccagct ttcttaacag    2100
cgttaacacc aaccttcaat tgttccaagt cgttcaaagc atcgaatact ctgaagatat    2160
cgacaccgtt atccttagct tgcttaacaa agtgatcaat ggcgttatct ggcaatgaag    2220
aataagcaac accattagca cctctcaaca acatttggaa agggatgttt ggaaccaaag    2280
atctcaactt tctcaatctt tcccaaggat cttcatgcaa gaatctcata gcaacatcga    2340
atgtagcacc accccaacat tccaaagcaa aagcaccagc taaagcatga gcagtagttg    2400
gagcaattgt agccaaatca tgggttctaa ctctagtagc caacaaagat tgatgagcat    2460
ctctccaagt ggtatccatc aacaaagtac cgttgaattg tctaacttgc ttagcgaatt    2520
cggaaggacc tttttccaac aaaacttgtc tccaacctga tggtgagct gatttggtaa     2580 cgttaataac attaccttga gcatcatgca agtgtggaac agatggatta gacttcaact    2640
```

```
ttggcaaacc aatttgaccc ttaatagaag aaccgttaac agccaaatct gccaagtaat    2700
gcaacaactt ttgtgctctg ttttgtgagg aaaccatttg gaataattgt ggggtatcat    2760
caatgaaggt agtccagtaa gtaccttcga tgaaaactgg gttagtcaac aaggtcaaca    2820
aaaatgggat gttggtctta acacctctga ttctgaattc gatcaaggct ctgatcatct    2880
ttcttctaac gatttcgtaa gtagaaccgg aacaagaaca cttgaccaac atagaatcat    2940
agtgtggaga aatagttgca ccagcatatg cattaccacc gtccaatcta acaccgttac    3000
caccggcaga tctgtaaact tccaatctac cagtatctgg ttggaagttc ttggatggat    3060
cttcggtagt aattctacat tgaatggaga acctctggt ggtaatctta tcttgcaaca    3120
aacccaattg agtcaaagta gcaccagcag caatttgaat ttgggcggaa actatatcga    3180
taccggtaat ttcttcggtg atggtatgtt cgacttggat tctaggattg atttcgatga    3240
agtagtgtct gttttgatta tcgaccaaga attcggcagt accagcattt ctataaccac    3300
agactttagc caacttaaca gcatcagtca aatggcatc tctaacttct cttggcaaag    3360
ttttagctgg agcaacttca acacctttt ggtgtcttct ttgaacggag caatctcttt    3420
caaacaagtg aacaacgtta ccgtggttat cagccaataa ttgaacttcg atgtgctttg    3480
gcttatccaa gaatctttcg acgaagcaag taccattacc aaaagcagtt ctagcttcag    3540
aagtagctct ttgaaaagca tcagcaacat catcaccttc tctaacaact ctcatacctc    3600
taccaccacc accgaaagca gccttgataa taactgggta accatattcg ttgacgaaat    3660
ccaaagcttc ttgaacagtt tcaattggac ctggagtacc tggaacagtt ggaacattag    3720
ctctagcagc caaatgtcta gcggaaactt tgtcaccaac agaatcaata acttcagctg    3780
gtggaccaat ccaagtaata ccagccttaa caaccttatc agcaaattca gagttttcgg    3840
acaagaaacc gtaacctgga tgaatgaaat caaccttgtg cttcttggcg atttcaataa    3900
tttcgtccat agccaaataa gcaccaactg gagtatattg accttcttca ccaataacgt    3960
aggcttcatc agctttcaat ctgtgcatag acaatctatc ttcgtgggag tagatagcaa    4020
tagttctcat ggacaattcg tgggcggatc taaaaattct gattgggatt tcacctctgt    4080
tggcaaccaa aatcttgttc ttttcaccca acaaggagaa gttatctctc aaaccagcca    4140
attttttgga ggaggacatt aaatttaact ccttaagtta ctttaatgat ttagtttta    4200 ttattaataa ttcatgctca tgacatctca tatacacgtt tataaaactt aaatagattg    4260
aaaatgtatt aaagattcct cagggattcg atttttttgg aagttttgt tttttttcc    4320 ttgagatgct gtagtatttg ggaacaatta taatcgaa agatatatgc ttacattcga    4380
ccgttttagc cgtgatcatt atcctatagt aacataacct gaagcataac tgacactact    4440
atcatcaata cttgtcacat gaggccttgg tggcc                              4475
```

<210> SEQ ID NO 23
<211> LENGTH: 3096
<212> TYPE: DNA
<213> ORGANISM: Artificial Sequence
<220> FEATURE:
<223> OTHER INFORMATION: Expression cassette

<400> SEQUENCE: 23

```
ggccttggtg gccgaataaa aaacacgctt tttcagttcg agtttatcat tatcaatact     60
gccatttcaa agaatacgta aataattaat agtagtgatt ttcctaactt tatttagtca    120
aaaaattagc cttttaattc tgctgtaacc cgtacatgcc caaaataggg ggcgggttac    180
```

```
acagaatata taacatcgta ggtgtctggg tgaacagttt attcctggca tccactaaat    240
ataatggagc ccgcttttta agctggcatc cagaaaaaaa aagaatccca gcaccaaaat    300
attgttttct tcaccaacca tcagttcata ggtccattct cttagcgcaa ctacagagaa    360
caggggcaca aacaggcaaa aaacgggcac aacctcaatg gagtgatgca acctgcctgg    420
agtaaatgat gacacaaggc aattgaccca cgcatgtatc tatctcattt tcttacacct    480
tctattacct tctgctctct ctgatttgga aaaagctgaa aaaaaaggtt gaaaccagtt    540
ccctgaaatt attcccctac ttgactaata agtatataaa gacggtaggt attgattgta    600
attctgtaaa tctatttctt aaacttctta aattctactt ttatagttag tcttttttt    660 agttttaaaa caccaagaac ttagtttcga ataaacacac ataaacaaac aaaatgttag    720
tgcttaccac cagttctctt atgtctcaat tcagtttgtt gtctttcgac ttctgggtca    780
aagttaatga attcatccaa acctgaacca ccagcaacca taggcaagac tggaaccttc    840
ttatcaactt caacttccaa caagacagga cccttagtag aaacgaattc tttcaactta    900
gcgtccaatt cttcttgctt tttgactctc aaaccttttta aacccatggc ttcagccaac    960
ttaatgaaat ctgggttcaa ttgatgggta tgggagtatc tatgttcgta gaacaaactt    1020
tgccattgtg tgaccatacc ttgttcttcg ttgttcaaga tcaaatcttt aactggagta   1080
ccagcttgaa cagcggaaga taattcagtc aaggtcatgt tgaaagaggc atcaccatca   1140
atatcaataa ccaaggattc tggtttagca acttgagcac caatagcagc tggcaaacca   1200
taccccatag tacccaaacc accagatgta atgaaagtat gaggatttct ccaagtccaa   1260
tgttgagcag cccacatttg atgttgacca acaccagtag taacgataac atgtctaccg   1320
gtatcgttag caaccttaga caacttcttg ataacggttt gtggcttgat tttagaacct   1380
ggagtttctt ccatgtaggc gtatgggtat tctttcttcc acttgttgat ttgagcgaac   1440
cattcagatc tttctttgac tgggaagatc ttagacatca tcttacccaa attagtagtt   1500
gcatcacctt caacggcgat ttgggtttga acaaccttgt tgatattctt tggggagact   1560
tcaaaatgaa taataccacc tctaccttca gcagcagctc tcctagcttc tggagcaaac   1620
ttggaaatgt taccagtgac tctatcatca aatctagcac caacagcaat aatcaagtcg   1680
gcgttttgaa cagccaaatt agcagtagca caaccatgca tacccaacat gtccaaggat   1740
tttggatctt cttgatcgaa ggaacccaaa ccttgtaaag tagtagtaac tggaatttgg   1800
gctctgtcgg acaattcttt caataatctt ggaccatcag catgattcaa ataccggca   1860 ccaacataca agactggttt ttttgccaag ttgatcaaat cggcagcctt gttaatagat   1920
tgcatgacga attcatcttg ggctctagaa gtcaattgat tcaaggcatt ggatggcaag   1980
gtagtcttag ttggaattgg atttctcaaa atggcggcag taacatcttt aggcaaatca   2040
accaaaactg gacctggtct acctgatgta gcaatttcga aagcttcgtt gattctcaat   2100
ggcaattctt caacggactt aaccatgacg ttccacttag tacaagatct agaaatacca   2160
acaacgtcag cttcttgaaa agcatctgta ccaatagcgg atgttggaac ttgaccagta   2220
aaaacaacca ttggaatacc atcagcgaaa gcatcagcca ttggagtaac aacattagta   2280
gcacctggac cagaagtaac caaaacaaca cctggtttac cagaagctct agcataacct   2340
tcagccatat gaccagcacc ttgttcatgt tttggcaaaa cgaagttgaa cttgtcggag   2400
ttgtgaatag catcataaac tggcaaaata gcaccacctg gataaccaaa aacggtatca   2460
acgttttgtc tggacatcat ttcgttgaag atttgaccac cagtcaaacc aacaaaagaa   2520
gtatccatat ctggttcggc tctcaacttt ttagccaatt tagatggttc agctggttgt   2580
```

```
tccaatggat caacgttaaa agatggagct ggttctggtc ttttagaagc tggcaatgga    2640
gaagcagagt aatatctgga ggatgaggag taaaatcttt gagccaaagc aacgatctc    2700 atggctggag tatttctgta agcgatatgt tggaagcatc tcttaatagc gaagttcttc    2760
aaggtggatt gtctgatcat taagtgaatt tactttaaat cttgcattta aataaatttt    2820 cttttatag ctttatgact tagtttcaat ttatatacta ttttaatgac attttcgatt     2880
cattgattga aagctttgtg ttttttcttg atgcgctatt gcattgttct tgtctttttc    2940
gccacatgta atatctgtag tagataccctg atacattgtg gatgctgagt gaaattttag   3000
ttaataatgg aggcgctctt aataattttg gggatattgg cttttttttt taaagtttac    3060
aaatgaattt tttccgccag gatggcctta gtggcc                              3096
```

<210> SEQ ID NO 24
<211> LENGTH: 1816
<212> TYPE: DNA
<213> ORGANISM: Artificial Sequence
<220> FEATURE:
<223> OTHER INFORMATION: Expression cassette

<400> SEQUENCE: 24

```
ggccttagtg gccgccgtac cacttcaaaa cacccaagca cagcatacta aatttcccct      60
ctttcttcct ctagggtgtc gttaattacc cgtactaaag gtttggaaaa gaaaaaagag     120
accgcctcgt ttcttttttct tcgtcgaaaa aggcaataaa aattttttatc acgtttcttt   180 ttcttgaaaa tttttttttt tgatttttttt ctctttcgat gacctcccat tgatatttaa    240
gttaataaac ggtcttcaat ttctcaagtt tcagtttcat ttttcttgtt ctattacaac     300
tttttttact tcttgctcat tagaaagaaa gcatagcaat ctaatctaag ttttaattac    360
aaaatgttag gaagaagcag atctagaagc aacgaattcc aaaccttgt caatgttctt    420 cttcaattgg gagacacaga ttggcaacat ttgatttctt tccatatcgt tcattctgtt    480
gacaatatcg taatcaacgt aggaaacacc cttggtagta atagtcaatg aatagcgaa     540 gtaatcagca ccatcaacca atggcaataa ttgatcagca cctggagcaa ttgggaaatt    600
gttagcatcc ttcaatggaa cgtagtaagt accatggatt tgttcgatgt acccaacaa     660 caaggaaacg aattgaacaa cgcatttgta accagcatga gccatagaca agtagcaga    720 accccttacca ttttagcct taacaacttc atcaccaccg tattgaactc tgtggatcaa    780
gtacttcaat tgatcttcgt tcaatctgga caagaagtta gattgggaga acaaagggat    840 aatggttttca ccagaatgac caccaataac aggaacatct ggcatagaat tgactcttgg    900
agtcaaacca gattcgatgt tgatttctct caagaaggta gaagctctaa cgatatccaa    960
cttggtaaca cccataattc ttctttcgat accggagttt ctagattgtg atggttctt   1020 caagatgtta ctgaccataa ctggaaccaa agagttaact gggttggaga taaccaaaac  1080 gaaaaccttac gacaaatcgc agcattcagc aatagaatca cccaattgag aaatgatacc  1140
ggcgttaacg ttgaacaaat catctctagt catacctggt tttcttggaa caccagctgg  1200
aataacaacg atggaagcat tatgcaagca attttctata ccaccggctg gagaatgtga    1260
agaaacggag attggggtat caatatgaga caatcagcg gtaacaccgt taatggcttc    1320
ttgattaaca tcgtacaagg ccaaatgaat atgggtgacg gatctattgg attctttcaa    1380
ttggtattgc aattgggcct tcaacaacaa agacaaagat tgaccaatac caccagcagc    1440
acccaaaata gcaatcttca aggaatcttg ttcaatggat ggggtaacag aatgtggcat    1500
```

| | | |
|---|---|---|
| taaggagatt gataagactt ttctagttgc atatcttttta tatttaaatc ttatctatta | 1560 | |
| gttaatttt tgtaatttat ccttatatat agtctggtta ttctaaaata tcatttcagt | 1620 | |
| atctaaaaat tcccctcttt tttcagttat atcttaacag gcgacagtcc aaatgttgat | 1680 | |
| ttatcccagt ccgattcatc agggttgtga agcattttgt caatggtcga atcacatca | 1740 | |
| gtaatagtgc ctcttacttg cctcatagaa tttctttctc ttaacgtcac cgtttggtct | 1800 | |
| tttggcctac ttggcc | 1816 | |

```
<210> SEQ ID NO 25
<211> LENGTH: 3112
<212> TYPE: DNA
<213> ORGANISM: Artificial Sequence
<220> FEATURE:
<223> OTHER INFORMATION: Expression cassette

<400> SEQUENCE: 25
```

| | | |
|---|---|---|
| ggcctacttg gccgggcgcc ataaccaagg tatctataga ccgccaatca gcaaactacc | 60 | |
| tccgtacatt catgttgcac ccacacattt atacacccag accgcgacaa attacccata | 120 | |
| aggttgtttg tgacggcgtc gtacaagaga acgtgggaac tttttaggct caccaaaaaa | 180 | |
| gaaagaaaaa atacgagttg ctgacagaag cctcaagaaa aaaaaattc ttcttcgact | 240 | |
| atgctggagg cagagatgat cgagccggta gttaactata tatagctaaa ttggttccat | 300 | |
| caccttcttt tctggtgtcg ctccttctag tgctatttct ggcttttcct atttttttt | 360 | |
| ttccattttt ctttctctct ttctaatata taaattctct tgcattttct attttttctct | 420 | |
| ctatctattc tacttgttta ttcccttcaa ggttttttt taaggagtac ttgttttag | 480 | |
| aatatacggt caacgaacta taattaacta acatgttac aatggttgag tttgagcttc | 540 | |
| aacaacggcc aaagcaacca tattaacgat tcttctaacg gaggcaattg gagtcaaaac | 600 | |
| atgaactggt ttagcaacac ccatcaaaac tggaccaaca gttacacctt cactggaaga | 660 | |
| gactctcaac aagttgtaag aaattctggc agcttccata tttggcatga ccaaaatgtt | 720 | |
| agcagaacct ttcaatgagg agtctggcat tctatcattt ctaatagctt caaccaaagc | 780 | |
| agcatcacca tgcatttcac catcaatcat caattctggt gctcttttctc tgaccaattc | 840 | |
| caaagcttgt ctcatttttg aagaggatgg gcagtctgaa gaaccaaaat tagaatggga | 900 | |
| caacaaggca actctaggtt caataccaaa tcttctaacg gtttcagcag ccatcaaagt | 960 | |
| aatttcagcc aattcttcag catctggttc atcgttaacg taagtatcag caatgaaggt | 1020 | |
| gttaccagat ggcaacaaca aagcattcat agcaccagca gtatgaacac catctctata | 1080 | |
| accgaaaacg ttcttgacaa cagagaagtg ttcatggtaa tcaccaacag taccacaaat | 1140 | |
| catagcgtca gcttcacctc tttgaaccat gatggcacca ataacagttg ggttagaaat | 1200 | |
| caaagctctt tgagcttgtt cttgagtgac acctcttctc ttcatgattt ggaagtattc | 1260 | |
| ggtccagtat tctttgaatc ttgggtcaga ttcattgtta acgatttcga agtcaacacc | 1320 | |
| ggccttgatt tgtaaaccta acttttggat tctcatttcg atgacgtttg gtctaccaat | 1380 | |
| caaaattggc ttagccaaac ccaaggtaac taattcttga gtagcgtgta aaactctagc | 1440 | |
| ttcttcacct tctggcaaaa caactctctt tggagccttt ctagcttgtg agaaaattgg | 1500 | |
| cttcatgaac aagttggtct tgtaaacgaa ttcggtcaac ttgtcgatgt aaacatcgaa | 1560 | |
| atcagcaatt ggtctagtag caacaccaga ttccatagca gctttagcaa cagctggagc | 1620 | |
| aatcttaacg atcaatcttg gatcgaatgg ctttgggatg atatattctg gaccaaaaga | 1680 | |
| caaatcttga tcaccataag cagatgcaac aacttctgat tgttcagcat gagccaattc | 1740 | |

```
agcaatagct ctaacagcag ccaacttcat ttcttcgtta atagcggtag caccaacatc    1800
caaagcacct ctaaaaatga atgggaagca caagacgttg ttaacttgat ttgggtaatc    1860
agatctaccg gtacagataa tagcgtctgg tctaacttct ttagccaatg gtggcaagat    1920
ttctggttct ggattagcta aagccaaaat cattggggct ctagccattt tcttaaccat    1980
ttcttgagtc aagacttttg gaccagaaca acccaagaaa atatcggcac cttcaataac    2040
atcatccaag gttctcttac catcatcaac aacagcataa gcagcttttg tttcagccat    2100
gttaggttct ctaccttggt agataacacc tttggaatcg caaacaacga tgttgtgctt    2160
ttgtaaaccc aaggcaacca acaaattcat acaagcaata gcagcagcac cagcaccaga    2220
aacaaccatt ctgacatcgg agatgttctt ttcaacaact ctcaaaccgt tcaaaatagc    2280
agcggtagaa ataatagcag taccatgttg atcatcgtgg aaaactggga tgttcattct    2340
ttctctcaac ttttgttcga tgtagaagca ttctggagcc ttaatatctt ccaagttaat    2400
accaccgaaa gtaggttcca aagcagcaac aacttcaatg aacttgtctg gatccaattc    2460
atcaacttcg atgtcgaaaa catcgatacc ggcgaacttt ttgaacaaaa caccttacc    2520 ttccataact ggtttaccag ccaaagcacc aatattaccc aaacccaaaa cggcagtacc    2580
attagaaata acggcaacca aattacctct agcagtgtac ttgtaagcct tcaatggatc    2640
tttttcaatt tccaaacatg gagcagcaac acctggagaa taagccaaag ccaaatctct    2700
ttgggtagcc aatggttttg ttggagaaac ttggatctta cctggaactg gaaattcatg    2760
gaaatccaag gcagattgct tcaattgatc atccattaag agtaataatt attgcttcca    2820
tataatattt ttatatacct cttatttta tgtattagtt aattaagtat ttttatctat    2880
ctgcttatca ttttctttc atataggggg ggttggtgtt ttcttgccca tcagattgat    2940
gtcctccaac tcggcactat tttacaaagg gtttttttgt aagagaagga gaagacagat    3000
actaaaccat acgttactcg aaacaaaaaa aaaaaaaatg gaaaaagctg ctatcaacaa    3060
aagacggcct catcaaacct aaagaaacca tgtcagcgtg gcctgtatgg cc            3112
```

<210> SEQ ID NO 26
<211> LENGTH: 2705
<212> TYPE: DNA
<213> ORGANISM: Artificial Sequence
<220> FEATURE:
<223> OTHER INFORMATION: Expression cassette

<400> SEQUENCE: 26

```
ggcctgtatg gccctactta ttcccttcga gattatatct aggaacccat caggttggtg     60
gaagattacc cgttctaaga cttttcagct tcctctattg atgttacacc tggacacccc    120
ttttctggca tccagttttt aatcttcagt ggcatgtgag attctccgaa attaattaaa    180
gcaatcacac aattctctcg gataccacct cggttgaaac tgacaggtgg tttgttacgc    240
atgctaatgc aaaggagcct atatacccttt ggctcggctg ctgtaacagg gaatataaag    300
ggcagcataa tttaggagtt tagtgaactt gcaacattta ctattttccc ttcttacgta    360
aatatttttc tttttaattc taaatcaatc ttttcaatt ttttgtttgt attctttct    420 tgcttaaatc tataactaca aaaaacacat acataaaacta aaaatgttac aattgattgg    480
tgtgaacgga tggatcgtgt tgaaccttaa tcattggtct gtaaactggt tcccacattt    540
gagccttaac ccattgcaag cattcgtcaa aatctcttgg aaccttaaca gtttcacctg    600
gagcaccacc tggaacttgt tcttgttcga ttctggcagt accttcttcc aaagcttgta    660
```

```
aaataacggc agttgccaat ctagcagagg tattagtaat ggtatccaaa cctggcaata    720
aacctggtct agaatcacct tctctcaatg gagacaattc agccaattga tcaacggcag    780
cagaaatcat cttgtcggta attgtagtag ctctagacaa acagcaccc  aaaccaatac    840
ctggaaagga gtagcagttg ttgttttcag agattctgta accatcaact ggtggaaatg    900
gagaaccagt agcaaccaaa gcattgttgt tagtccactt catcaaatca gctggaacag    960
cttcatgcaa tctagttggg ttagacaatg gaagatgat  aggtcttgga ttgtgcttat   1020
gcatttcttc aacgacatct tgtgtaaaag caccagcttg agtagaacaa ccaaccaaac   1080
aagtaggctt aacgttttcg acaacatcgt gcaatgatct agtgttaata ccagcccatt   1140
cagcatcaga tttagcgtaa acatgttgag ctggggtaga attagcttcg taggattgca   1200
atatcaaacc tcttctgtcc atcaagaaga tcttttttct ggcttcttct ttgtcgacac   1260
catgagtaac catgtggtta acgatttgat ctgcaatacc taaaccagca gaaccagcac   1320
catagatcaa gactctggta tctttcaaat ctctgttagt gtgcttcaat gcagcaatca   1380
aagaagccat aacaacagca ccagtacctt gaatgtcatc gttgaaggat ggcaattcgt   1440
atctgtactt ttctaataat cttctggcgt tcttaacacc gaaatcttcg aagtgtaaaa   1500
cagcggatgg ataaaccttc ttaacggcct tgatgaactt ttccaagaaa tcgtcgtatt   1560
gcttacctct gattctggag aacttgttac ccatgtacaa ttcatctctg ccaacttttt   1620
tgttgttttgt accaacatcc aaacaaactg gcaaaactct acctggatga ataccaccac   1680
acaaggtcat caaagccaac ttagaaatag caattctgac accacctata ccttgatcac   1740
caatacccaa aataccttcg gagtcggaaa caacgatgta atcaacatcc ttatcaccac   1800
cataagtagc caatctacat tcaatggaat ctggttcggt gatatccaaa aagacacctt   1860
ctggttttct gaatctgtga gaataagcag caatagcatc accttcagtt ggagtgtaga   1920
tgattggaac caattctttg atgtgtcttc tgatcaaggc gaagtacaag accttgtttt   1980
gaactctcaa agaagtcatg aaatcgttct tggccaatgg agttttcaag tagcacaatt   2040
gcttgtagga tctttccaat tgttcatcca agtgttaaac ttgtggtggc aacaaagctt   2100
ccaagttgaa agcttctctt tcttcttgag tgaaagcaga acccttgttg aacaaaggtg   2160
agttcaataa ttggaaggat tccaatgggc attcaatagc accttcaaca gtcaatctag   2220
tagcatgtgg atgtggagct tcaaaaatct ttctggctct agaaccaact ggagtcttag   2280
taacttcttc atcggagtat ggcttttgga aggtgttttc tctagtagta gtagccttat   2340
gagatctggt gttagaagag tataatctgg attgttggat tggccacatt aagattaata   2400
taattatata aaaatattat cttctttttct ttatatctag tgttatgtaa aataaattga   2460
tgactacgga aagctttttt atattgtttc tttttcattc tgagccactt aaatttcgtg   2520
aatgttcttg taagggacgg tagatttaca agtgatacaa caaaaagcaa ggcgcttttt   2580
ctaataaaaa gaagaaaagc atttaacaat tgaacacctc tatatcaacg aagaatatta   2640
ctttgtctct aaatccttgt aaaatgtgta cgatctctat atgggttact caggcctctt   2700
tggcc                                                               2705
```

<210> SEQ ID NO 27
<211> LENGTH: 31
<212> TYPE: DNA
<213> ORGANISM: Artificial Sequence
<220> FEATURE:
<223> OTHER INFORMATION: primer

<400> SEQUENCE: 27
gtttgctgtc ttgctatcaa gtataaatag a    31

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
gatttaaacc ttgggcacca ca    22

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
gatgatcgct atggttaagg ct    22

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
ctaacggatt tctgcacttg at    22

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
cgataccaac ttgggctttc t    21

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gcatgctggt gatgttgct    19

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
gccaatactt cacaatgttc gaatct    26

<210> SEQ ID NO 34
<211> LENGTH: 23
<212> TYPE: DNA

```
<213> ORGANISM: Artificial Sequence
<220> FEATURE:
<223> OTHER INFORMATION: primer

<400> SEQUENCE: 34
cgatcaatct tggagacttt gga                                          23

<210> SEQ ID NO 35
<211> LENGTH: 17
<212> TYPE: DNA
<213> ORGANISM: Artificial Sequence
<220> FEATURE:
<223> OTHER INFORMATION: primer

<400> SEQUENCE: 35
gggctattgc agctgct                                                 17

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
caaggctctt tcactctcct                                              20

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
gcgttcaatt cgttagcatt acca                                         24

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
gctgacaaag aatctagaca cttgt                                        25

<210> SEQ ID NO 39
<211> LENGTH: 31
<212> TYPE: DNA
<213> ORGANISM: Artificial Sequence
<220> FEATURE:
<223> OTHER INFORMATION: primer

<400> SEQUENCE: 39
cttgcataaa ttggtcaatg caagaaatac a                                 31

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
cttctttctt gaaaccagta gcataca                                      27
```

```
<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
gttgttgtca ttagatatga aggtcca                                              27

<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
gccctctttt gaactgtcat ataaatac                                             28

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
gatttgcttc aaacctctgg tagt                                                 24

<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
gatgggtggt attcatggta tgt                                                  23

<210> SEQ ID NO 45
<211> LENGTH: 33
<212> TYPE: DNA
<213> ORGANISM: Artificial Sequence
<220> FEATURE:
<223> OTHER INFORMATION: primer

<400> SEQUENCE: 45
gacaatatat tttcacacaa tgagatttgt agt                                       33

<210> SEQ ID NO 46
<211> LENGTH: 24
<212> TYPE: DNA
<213> ORGANISM: Artificial Sequence
<220> FEATURE:
<223> OTHER INFORMATION: primer

<400> SEQUENCE: 46
caatgaatat cggaaccgca aaca                                                 24

<210> SEQ ID NO 47
<211> LENGTH: 22
<212> TYPE: DNA
<213> ORGANISM: Artificial Sequence
<220> FEATURE:
```

<223> OTHER INFORMATION: primer

<400> SEQUENCE: 47
gctactttgg aagaaggtga ct                                    22

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
gtaggtttgg aagaatatat aaaggttgca                            30

<210> SEQ ID NO 49
<211> LENGTH: 24
<212> TYPE: DNA
<213> ORGANISM: Artificial Sequence
<220> FEATURE:
<223> OTHER INFORMATION: primer

<400> SEQUENCE: 49
gggagtagat agcaatagtt ctca                                  24

<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50
gatcattaag ttgcaagcag ttggt                                 25

<210> SEQ ID NO 51
<211> LENGTH: 35
<212> TYPE: DNA
<213> ORGANISM: Artificial Sequence
<220> FEATURE:
<223> OTHER INFORMATION: primer

<400> SEQUENCE: 51
ctaataagta tataaagacg gtaggtattg attgt                      35

<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52
gctggcaatg gagaagca                                         18

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
cgctgttcaa gctggtact                                        19

```
<210> SEQ ID NO 54
<211> LENGTH: 26
<212> TYPE: DNA
<213> ORGANISM: Artificial Sequence
<220> FEATURE:
<223> OTHER INFORMATION: primer

<400> SEQUENCE: 54
cgatgacctc ccattgatat ttaagt                                           26

<210> SEQ ID NO 55
<211> LENGTH: 27
<212> TYPE: DNA
<213> ORGANISM: Artificial Sequence
<220> FEATURE:
<223> OTHER INFORMATION: primer

<400> SEQUENCE: 55
cggatctatt ggattctttc aattggt                                          27

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
gtgatgaagt tgttaaggct aaaaatggt                                        29

<210> SEQ ID NO 57
<211> LENGTH: 40
<212> TYPE: DNA
<213> ORGANISM: Artificial Sequence
<220> FEATURE:
<223> OTHER INFORMATION: primer

<400> SEQUENCE: 57
catttttctt tctctctttc taatatataa attctcttgc                            40

<210> SEQ ID NO 58
<211> LENGTH: 17
<212> TYPE: DNA
<213> ORGANISM: Artificial Sequence
<220> FEATURE:
<223> OTHER INFORMATION: primer

<400> SEQUENCE: 58
gcagcaacac ctggaga                                                     17

<210> SEQ ID NO 59
<211> LENGTH: 28
<212> TYPE: DNA
<213> ORGANISM: Artificial
<220> FEATURE:
<223> OTHER INFORMATION: primer

<400> SEQUENCE: 59
gttgtcccat tctaattttg gttcttca                                         28

<210> SEQ ID NO 60
<211> LENGTH: 28
<212> TYPE: DNA
<213> ORGANISM: Artificial Sequence
<220> FEATURE:
<223> OTHER INFORMATION: primer
```

```
<400> SEQUENCE: 60
ggagtttagt gaacttgcaa catttact                                        28

<210> SEQ ID NO 61
<211> LENGTH: 24
<212> TYPE: DNA
<213> ORGANISM: Artificial Sequence
<220> FEATURE:
<223> OTHER INFORMATION: primer

<400> SEQUENCE: 61
ggagcttcaa aaatctttct ggct                                            24

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
ctttccaggt attggtttgg gt                                              22
```